US011564963B2

(12) United States Patent
Scharp et al.

(10) Patent No.: US 11,564,963 B2
(45) Date of Patent: Jan. 31, 2023

(54) TOPICAL COMPOSITIONS, PROCESS OF LARGE-SCALE MANUFACTURE, AND METHOD OF USE

(71) Applicant: Progeneron, LLC, Aliso Viejo, CA (US)

(72) Inventors: David Scharp, Aliso Viejo, CA (US); Mukhtar Siddiqui, San Ramon, CA (US); Jennifer Aguas Hurtikant, Downey, CA (US); David Bondurant, San Clemente, CA (US); Brian Haight, Yorba Linda, CA (US)

(73) Assignee: Progeneron, LLC, Aliso Viejo, CA (US)

( * ) Notice: Subject to any disclaimer, the term of this patent is extended or adjusted under 35 U.S.C. 154(b) by 0 days.

(21) Appl. No.: 16/882,429

(22) Filed: May 22, 2020

(65) Prior Publication Data
US 2020/0281998 A1 Sep. 10, 2020

Related U.S. Application Data

(63) Continuation-in-part of application No. 16/198,793, filed on Nov. 22, 2018, now abandoned.

(60) Provisional application No. 62/590,251, filed on Nov. 22, 2017.

(51) Int. Cl.
| | | |
|---|---|---|
| *A61K 36/23* | (2006.01) |
| *A61Q 19/08* | (2006.01) |
| *A61K 9/107* | (2006.01) |
| *A61K 31/015* | (2006.01) |
| *A61K 47/42* | (2017.01) |
| *A61K 36/28* | (2006.01) |
| *A61K 31/25* | (2006.01) |
| *A61K 36/185* | (2006.01) |
| *A61K 31/201* | (2006.01) |
| *A61K 31/05* | (2006.01) |
| *A61K 31/455* | (2006.01) |
| *A61K 47/14* | (2017.01) |
| *A61K 36/886* | (2006.01) |
| *A61K 47/26* | (2006.01) |
| *A61K 33/06* | (2006.01) |
| *A61K 8/9794* | (2017.01) |
| *A61K 8/9789* | (2017.01) |
| *A61K 8/31* | (2006.01) |
| *A61K 9/00* | (2006.01) |

(52) U.S. Cl.
CPC .............. *A61K 36/23* (2013.01); *A61K 8/31* (2013.01); *A61K 8/9789* (2017.08); *A61K 8/9794* (2017.08); *A61K 9/0014* (2013.01); *A61K 9/107* (2013.01); *A61K 31/015* (2013.01); *A61K 31/05* (2013.01); *A61K 31/201* (2013.01); *A61K 31/25* (2013.01); *A61K 31/455* (2013.01); *A61K 33/06* (2013.01); *A61K 36/185* (2013.01); *A61K 36/28* (2013.01); *A61K 36/886* (2013.01); *A61K 47/14* (2013.01); *A61K 47/26* (2013.01); *A61K 47/42* (2013.01); *A61Q 19/08* (2013.01)

(58) Field of Classification Search
CPC ........ A61Q 19/08; A61K 36/23; A61K 9/107; A61K 31/015; A61K 47/42; A61K 36/28; A61K 31/25; A61K 36/185; A61K 31/201; A61K 31/05; A61K 31/455; A61K 47/14; A61K 36/886; A61K 47/26; A61K 33/06; A61K 8/9794; A61K 8/9789; A61K 8/31; A61K 9/0014
See application file for complete search history.

(56) References Cited

U.S. PATENT DOCUMENTS

| | | | |
|---|---|---|---|
| 4,784,842 A | 11/1988 | London et al. | |
| 6,190,704 B1 * | 2/2001 | Murrell ............... | A61K 31/145 424/718 |
| 6,660,280 B1 | 12/2003 | Allard et al. | |

(Continued)

FOREIGN PATENT DOCUMENTS

| | | |
|---|---|---|
| AU | 2009222500 A1 | 4/2011 |
| EP | 3090780 A1 | 11/2016 |

(Continued)

OTHER PUBLICATIONS

Dae-Sung Kim, et al, Alpha-Pinene Exhibits Anti-inflammatory Activity Through the Suppression of MAPKs and the NF-κB Pathway in Mouse Peritoneal Macrophages, 43 Am. J Chinese Med. 731 (Year: 2015).*

International Search Report and Written Opinion for corresponding International Application No. PCT/US2018/62360, dated Jan. 16, 2019, 7 pages.

(Continued)

*Primary Examiner* — Sean M Basquill
(74) *Attorney, Agent, or Firm* — Austin LLP

(57) ABSTRACT

Compositions for the treatment of some orphan diseases and oral mucosal ulcers, many with similarities in terms of their anti-inflammatory and anti-oxidative activities, but also multiple differences in their observed abilities that can be combined to challenge the current, underlying pathophysiology. The orphan diseases of interest are Dupuytren's Contracture, Peyronie's Disease, Scleroderma, Raynaud's (or Renaud's) Phenomenon, chemotherapy/radiation induced oral mucosal ulceration, and aphthous ulcers; and more frequent skin issues of skin damage from cuts, abrasions, and burns; aging skin changes, and toe nail fungus. These can be treated with the disclosed compositions with the proper combination and alteration of ingredients inclusive of alpha-pinene, an aloe vera preparation, and a shea butter preparation. A process for preparation of such ingredients in a water-in-oil emulsion is described herein.

14 Claims, 7 Drawing Sheets

(56) References Cited

U.S. PATENT DOCUMENTS

| | | | |
|---|---|---|---|
| 10,471,131 | B2 | 11/2019 | Twidwell et al. |
| 2005/0281762 | A1 | 12/2005 | Modak et al. |
| 2008/0038219 | A1* | 2/2008 | Mosbaugh .............. A61K 8/466 |
| | | | 424/74 |
| 2008/0241079 | A1 | 10/2008 | Neubourg |
| 2011/0091572 | A1 | 4/2011 | Davidson |
| 2011/0136210 | A1 | 6/2011 | Benjamin et al. |
| 2013/0287708 | A1 | 10/2013 | Silberstein et al. |
| 2015/0182578 | A1 | 7/2015 | Cavallaro |
| 2016/0045412 | A1 | 2/2016 | Davies |
| 2016/0089325 | A1 | 3/2016 | Perkins |
| 2017/0087199 | A1 | 3/2017 | Patron |
| 2019/0151232 | A1 | 5/2019 | Scharp |

FOREIGN PATENT DOCUMENTS

| | | |
|---|---|---|
| KR | 10-0873946 | 12/2008 |
| WO | 2012056044 A1 | 5/2012 |
| WO | 2012/177986 A2 | 12/2012 |
| WO | 2013149323 A1 | 10/2013 |
| WO | 2016141219 A1 | 9/2016 |

OTHER PUBLICATIONS

International Search Report and Written Opinion for corresponding International Application No. PCT/US20/34422, dated Oct. 30, 2020, 15 pages.

Farhoudi, R., "Chemical Constituents and Antioxidant Properties of Matricaria recutita and Chamaemelum nobile Essential Oil Growing Wild in the South West of Iran", Journal of Essential Oil Bearing Plants; abstract, 1 page, Oct. 25, 2013.

Bourgou, S et al., "Bioactivities of black cumin essential oil and its main terpenes from Tunisia", South African Journal of Botany 76 (2010) pp. 210-216; table 1, 7 pages.

Schleehauf, "Croda Inc's Cithrol PGTL" Cosmetics & Toiletries, Jul. 1, 2019, https://www.cosmeticsandtoiletries.com/formulating/category/natural/Croda-Incs-Cithrol-PGTL-512114081.html, 2 page.

"Making Shea Butter in Ghana" (Cof, K, Apr. 17, 2016; available at: https://safarijunkie.com/ghana/making-shea-butter-in-ghana, p. 18, 3$^{rd}$ paragraph) (Year: 2016), 26 pages.

Allenspach, M.; Steuer, C. α-Pinene: A Never-Ending Story. Phytochemistry. Elsevier Ltd Oct. 1, 2021. https://doi.org/10.1016/j.phytochem.2021.112857.

Aloecream.biz. Hawaiian Moon Aloe Vera Cream Ingredients. 2021 (https://aloecream.biz/ingredients/).

Aragona, C. O.; Versace, A. G.; Ioppolo, C.; La Rosa, D.; Lauro, R.; Tringali, M. C.; Tomeo, S.; Ferlazzo, G.; Roberts, W. N.; Bitto, A.; Irrera, N.; Bagnato, G. Emerging Evidence and Treatment Perspectives from Randomized Clinical Trials in Systemic Sclerosis: Focus on Interstitial Lung Disease. Biomedicines. MDPI Feb. 1, 2022. https://doi.org/10.3390/biomedicines10020504.

Bae, G. S.; Park, K. C.; Choi, S. B.; Jo, I. J.; Choi, M. O.; Hong, S. H.; Song, K.; Song, H. J.; Park, S. J. Protective Effects of Alpha-Pinene in Mice with Cerulein-Induced Acute Pancreatitis. Life Sci. 2012, 91 (17-18), 866-871. https://doi.org/10.1016/j.lfs.2012.08.035.

Ball C, Izadi D, Verjee LS, Chan J, Nanchahal J. Systematic review of non-surgical treatments for early dupuytren's disease. BMC Musculoskelet Disord. 2016;17(1):345. Published Aug. 15, 2016. doi:10.1186/s12891-016-1200-y.

Ballester, B.; Milara, J.; Cortijo, J. Pirfenidone Anti-Fibrotic Effects Are Partially Mediated by the Inhibition of MUC1 Bioactivation; 2020; vol. 11.

Bochaton-Piallat, M. L.; Gabbiani, G.; Hinz, B. The Myofibroblast in Wound Healing and Fibrosis: Answered and Unanswered Questions. F1000Research. Faculty of 1000 Ltd 2016. https://doi.org/10.12688/f1000research.8190.1.

Chen, Weiqiang, et al., Anti tumor effect of α-pinene on human hepatoma cell lines through inducing G2/M cell cycle arrest, Journal of Pharmacological Sciences, vol. 127, Issue 3, 2015, pp. 332-338, ISSN 1347-8613, https://doi.org/10.1016/j.jphs.2015.01.008.

Cokol-Cakmak, M.; Bakan, F.; Cetiner, S.; Cokol, M. Diagonal Method to Measure Synergy among Any Number of Drugs. J. Vis. Exp. 2018, 2018 (136). https://doi.org/10.3791/57713.

Dagne, E.; Bisrat, D.; Viljoen, A.; Van Wyk, B.-E. Chemistry of Aloe Species; 2000; vol. 4.

Darby, I.A., Zakuan, N., Billet, F. et al. The myofibroblast, a key cell in normal and pathological tissue repair. Cell. Mol. Life Sci. 73, 1145-1157 (2016). https://doi.org/10.1007/s00018-015-2110-0.

Degreef, I. Collagenase Treatment in Dupuytren Contractures: A Review of the Current State Versus Future Needs. Rheumatol Ther3, 43-51 (2016). https://doi.org/10.1007/s40744-016-0027-1.

Demidenko, E.; Miller, T. W. Statistical Determination of Synergy Based on Bliss Definition of Drugs Independence. PLoS One 2019, 14 (11). https://doi.org/10.1371/journal.pone.0224137.

Denkler, K. A.; Park, K. M.; Alser, O. Treatment Options for Dupuytren's Disease: Tips and Tricks. Plastic and Reconstructive Surgery—Global Open. Lippincott Williams and Wilkins Jan. 27, 2022, p. E4046. https://doi.org/10.1097/GOX.0000000000004046.

Di Veroli, G. Y.; Fomari, C.; Wang, D.; Mollard, S.; Bramhall, J. L.; Richards, F. M.; Jodrell, D. I. Combenefit: An Interactive Platform for the Analysis and Visualization of Drug Combinations. Bioinformatics 2016, 32 (18), 2866-2868. https://doi.org/10.1093/bioinformatics/btw230.

DiBenedetti, D. B.; Nguyen, D.; Zografos, L.; Ziemiecki, R.; Zhou, X. Prevalence, Incidence, and Treatments of Dupuytren's Disease in the United States: Results from a Population-Based Study. Hand 2011, 6 (2), 149-158. https://doi.org/10.1007/s11552-010-9306-4.

Dolmans, G. H.; Werker, P. M.; Hennies, H. C.; Furniss, D.; Festen, E. A.; Franke, L.; Becker, K.; van der Vlies, P.; Wolffenbuttel, B. H.; Tinschert, S.; Toliat, M. R.; Nothnagel, M.; Franke, A.; Klopp, N.; Wichmann, H.-E.; Nürnberg, P.; Giele, H.; Ophoff, R. A.; Wijmenga, C. Wnt Signaling and Dupuytren's Disease. N. Engl. J. Med. 2011, 365 (4), 307-317. https://doi.org/10.1056/nejmoa1101029.

Faustman, D. L.; Davis, M. TNF Receptor 2 and Disease: Autoimmunity and Regenerative Medicine. Front. Immunol. 2013, Dec. 4, https://doi.org/10.3389/fimmu.2013.00478.

Fortier, S. M.; Penke, L. R.; King, D.; Pham, T. X.; Ligresti, G.; Peters-Golden, M. Myofibroblast Dedifferentiation Proceeds via Distinct Transcriptomic and Phenotypic Transitions. JCI Insight 2021, 6 (6). https://doi.org/10.1172/jci.insight.144799.

Gelbard MK, Rosenbloom J. Fibroproliferative disorders and diabetes: Understanding the pathophysiologic relationship between Peyronie's disease, Dupuytren disease and diabetes. Endocrinol Diabetes Metab. 2020;4(2):e00195. Published Oct. 31, 2020. doi:10.1002/edm2.195.

Gerarduzzi, C.; Di Battista, J. A. Myofibroblast Repair Mechanisms Post-Inflammatory Response: A Fibrotic Perspective. Inflammation Research. Birkhauser Verlag AG Jun. 1, 2017, pp. 451-465. https://doi.org/10.1007/s00011-016-1019-x.

Gibb, A. A.; Lazaropoulos, M. P.; Elrod, J. W. Myofibroblasts and Fibrosis: Mitochondrial and Metabolic Control of Cellular Differentiation. Circulation Research. Lippincott Williams and Wilkins Jul. 17, 2020, pp. 427-447. https://doi.org/10.1161/CIRCRESAHA.120.316958.

Graziani, F.; Lillo, R.; Crea, F. Rationale for the Use of Pirfenidone in Heart Failure With Preserved Ejection Fraction. Front. Cardiovasc. Med. 2021, 0, 337. https://doi.org/10.3389/FCVM 2021.678530.

Greco, W. R.; Faessel, H.; Levasseur, L. The Search for Cytotoxic Synergy Between Anticancer Agents: A Case of Dorothy and the Ruby Slippers?; 1996.

Gupta SC, Sundaram C, Reuter S, Aggarwal BB. Inhibiting NF-κB activation by small molecules as a therapeutic strategy. Biochim Biophys Acta. 2010;1799(10-12):775-787. doi:10.1016/j.bbagrm.2010.05.004.

Haghdoost, F.; Baradaran Mahdavi, M. M.; Zandifar, A.; Sanei, M. H.; Zolfaghari, B.; Javanmard, S. H. Pistacia Atlantica Resin Has a Dose-Dependent Effect on Angiogenesis and Skin Burn Wound Healing in Rat. Evidence-based Complement. Altern. Med. 2013, 2013. https://doi.org/10.1155/2013/893425.

(56) References Cited

OTHER PUBLICATIONS

Hamman, J. H. Composition and Applications of Aloe Vera Leaf Gel. Molecules. Aug. 2008, pp. 1599-1616. https://doi.org/10.3390/molecules13081599.

Hinz, B.; Lagares, D. Evasion of Apoptosis by Myofibroblasts: A Hallmark of Fibrotic Diseases. Nature Reviews Rheumatology Nature Research Jan. 1, 2020, pp. 11-31. https://doi.org/10.1038/s41584-019-0324-5.

Holzer, L. A.; Cör, A.; Pfandlsteiner, G.; Holzer, G. Acta Orthopaedica Expression of VEGF, Its Receptors, and HIF-1α in Dupuytren's Disease Expression of VEGF, Its Receptors, and HIF-1α in Dupuytren's Disease. Acta Orthop. 2013, 84 (4), 420-425. https://doi.org/10.3109/17453674.2013.814011.

Hou, J.; Zhang, Y.; Zhu, Y.; Zhou, B.; Ren, C.; Liang, S.; Guo, Y. A-Pinene Induces Apoptotic Cell Death via Caspase Activation in Human Ovarian Cancer Cells. Med. Sci. Monit. 2019, 25, 6631-6638. https://doi.org/10.12659/MSM.916419.

Ianevski, A.; Giri, A. K.; Aittokallio, T. SynergyFinder 2.0: Visual Analytics of Multi-Drug Combination Synergies. Nucleic Acids Res. 2021, 48 (1), W488-W493. https://doi.org/10.1093/NAR/GKAA216.

Ianevski, A.; Giri, A. K.; Aittokallio, T. SynergyFinder 3.0: An Interactive Analysis and Consensus Interpretation of Multi-Drug Synergies across Multiple Samples. Nucleic Acids Res. 2022. https://doi.org/10.1093/nar/gkac382.

Izadi, D.; Layton, T. B.; Williams, L.; Mccann, F.; Cabrita, M.; Santo, A. I. E.; Xie, W.; Frilzsche, M.; Colin-York, H.; Feldmann, M.; Midwood, K. S.; Nanchahal, J. Identification of TNFR2 and IL-33 as Therapeutic Targets in Localized Fibrosis; 2019; vol. 5.

Jung, J., Kim, G.W., Lee, B. et al. Integrative genomic and transcriptomic analysis of genetic markers in Dupuytren's disease. BMC Med Genomics 12, 98 (2019). https://doi.org/10.1186/s12920-019-0518-3.

Kafle, S.; Thapa Magar, M.; Patel, P.; Poudel, A.; Cancarevic, I. Systemic Sclerosis Associated Interstitial Lung Disease and Nintedanib: A Rare Disease and a Promising Drug. Cureus 2021. https://doi.org/10.7759/cureus.16404.

Kalliolias, G., Ivashkiv, L. TNF biology, pathogenic mechanisms and emerging therapeutic strategies. Nat Rev Rheumatol 12,49-62 (2016). https://doi.org/10.1038/nrrheum.2015.169.

Kang, E.; Lee, D. H.; Jung, Y. J.; Shin, S. Y.; Koh, D.; Lee, Y. H. α-Pinene Inhibits Tumor Invasion through Downregulation of Nuclear Factor (NF)-KB-Regulated Matrix Metalloproteinase-9 Gene Expression in MDA-MB-231 Human Breast Cancer Cells. Appl. Biol. Chem. 2016, 59 (4), 511-516. https://doi.org/10.1007/s13765-016-0175-6.

Kanta, J. Collagen Matrix as a Tool in Studying Fibroblastic Cell Behavior. Cell Adhes. Migr. 2015, 9 (4), 308-316. https://doi.org/10.1080/19336918.2015.1005469.

Kato, K.; Logsdon, N. J.; Shin, Y. J.; Palumbo, S.; Knox, A.; Irish, J. D.; Rounseville, S. P.; Rummel, S. R.; Mohamed, M.; Ahmad, K.; Trinh, J. M.; Kurundkar, D.; Knox, K. S.; Thannickal, V. J.; Hecker, L. Impaired Myofibroblast Dedifferentiation Contributes to Nonresolving Fibrosis in Aging. Am. J. Respir. Cell Mol. Biol. 2020, 62 (5), 633-644. https://doi.org/10.1165/RCMB.2019-0092OC.

Katsumoto, T. R.; Whitfield, M. L.; Connolly, M. K. The Pathogenesis of Systemic Sclerosis. Annu. Rev. Pathol. Mech. Dis. 2011, 6, 509-537. https://doi.org/10.1146/annurev-pathol-011110-130312.

Khinkis, L. A.; Levasseur, L.; Faessel, H.; Greco, W. R. Optimal Design for Estimating Parameters of the 4-Parameter Hill Model. Nonlinearity Biol. Toxicol. Med. 2003, 363-377.

Layton T, Nanchahal J. Recent advances in the understanding of Dupuytren's disease. F1000Res. Feb. 28, 2019;8: F1000 Faculty Rev-231, doi: 10.12688/f1000research.17779.1. PMID: 30854193; PMCID: PMC6396840.

Lipman, M. D.; Carstensen, S. E.; Deal, D. N. Trends in the Treatment of Dupuytren Disease in the United States Between 2007 and 2014. Hand. SAGE Publications Inc. Jan. 1, 2017, pp. 13-20. https://doi.org/10.1177/1558944716647101.

Liu, H.; Liang, F.; Wong, J.; Fujiwara, T.; Ye, W.; Tsubota, K. iti; Sugawara, M. Multi-Scale Modeling of Hemodynamics in the Cardiovascular System. Acta Mech. Sin. Xuebao 2015, 31 (4), 446-464. https://doi.org/10.1007/s10409-015-0416-7.

Liu, S.; Rong, L.; Deng, J.; Zhao, X.; Liu, X.; Xu, X.; Qin, Z. TNFR2 Expression on Non-Bone Marrow-Derived Cells Is Crucial for Lipopolysaccharide-Induced Septic Shock and Downregulation of Soluble TNFR2 Level in Serum. Cell. Mol. Immunol. 2011, 8 (2), 164-171. https://doi.org/10.1038/cmi.2010.79.

Lopez-de la Mora, D. A.; Sanchez-Roque, C.; Montoya-Buelna, M.; Sanchez-Enriquez, S.; Lucano-Landeros, S.; Macias-Barragan, J.; Armendariz-Borunda, J. Role and New Insights of Pirfenidone in Fibrotic Diseases. International journal of medical sciences. 2015, pp. 840-847. https://doi.org/10.7150/ijms.11579.

Ma, J.; Motsinger-Reif, A. Current Methods for Quantifying Drug Synergism. Proteomics Bioinforma. PB 2019, 1 (2), 43-48.

Masur, S. K.; Dewait, H. S.; Dinht, T. T.; Erenburgt, I.; Petridout, S. Myofibroblasts Differentiate from Fibroblasts When Plated at Low Density (Transforming Growth Factor Fp/Cornea/lntegrins/Fibroblasts/Smooth Muscle a-Actin); 1996 vol. 93.

Meldstad, Fataneh, Hydrolysis of Marine Cod (Gadus Morhua) Head, NTNU-Trondheim (available at https://ntnuopen.ntnu.no/ntnu-xmlui/bitstream/handle/11250/2351655/14064_FU LL TEXT.pdf?sequence=1) (Year: 2015).

Meyer, C. T.; Wooten, D. J.; Lopez, C. F.; Quaranta, V. Charting the Fragmented Landscape of Drug Synergy. Trends in Pharmacological Sciences. Elsevier Ltd Apr. 1, 2020, pp. 266-280. https://doi.org/10.1016/j.tips.2020.01.011.

Meyer, C. T.; Wooten, D. J.; Paudel, B. B.; Bauer, J.; Hardeman, K. N.; Westover, D.; Lovly, C. M.; Harris, L. A.; Tyson, D. R.; Quaranta, V. Quantifying Drug Combination Synergy along Potency and Efficacy Axes. Cell Syst. 2019, 8 (2), 97-108.e16. https://doi.org/10.1016/j.cels.2019.01.003.

Michalik, M.; Wójcik-Pszczola, K.; Paw, M.; Wnuk, D.; Koczurkiewicz, P.; Sanak, M.; Pękala, E.; Madeja, Z. Fibroblast-to-Myofibroblast Transition in Bronchial Asthma. Cellular and Molecular Life Sciences. Birkhauser Verlag AG Nov. 1, 2018, pp. 3943-3961. https://doi.org/10.1007/s00018-018-2899-4.

Milani, B. Y.; Milani, F. Y.; Park, D.-W.; Namavari, A.; Shah, J.; Amirjamshidi, H.; Ying, H.; Djalilian, A. R. Rapamycin Inhibits the Production of Myofibroblasts and Reduces Corneal Scarring After Photorefractive Keratectomy; 2013.

Monaco, C.; Nanchahal, J.; Taylor, P.; Feldmann, M. Anti-TNF Therapy: Past, Present and Future. Int. Immunol. 2015, 27 (1), 55-62. https://doi.org/10.1093/intimm/dxu102.

Nanchahal, J.; Ball, C.; Davidson, D.; Williams, L.; Sones, W.; McCann, F. E.; Cabrita, M.; Swettenham, J.; Cahoon, N. J.; Copsey, B.; Anne Francis, E.; Taylor, P. C.; Black, J.; Barber, V. S.; Dutton, S.; Feldmann, M.; Lamb, S. E. Anti-Tumour Necrosis Factor Therapy for Dupuytren's Disease: A Randomised Dose Response Proof of Concept Phase 2a Clinical Trial. EBioMedicine 2018, 33, 282-288. https://doi.org/10.1016/j.ebiom.2018.06.022.

Nanchahal, J.; Ball, C.; Rombach, I.; Williams, L.; Kenealy, N.; Dakin, H.; O'Connor, H.; Davidson, D.; Werker, P. Dutton, S. J.; Feldmann, M.; Lamb, S. E. Anti-Tumour Necrosis Factor Therapy for Early-Stage Dupuytren's Disease (RIDD): A Phase 2b, Randomised, Double-Blind, Placebo-Controlled Trial Lancet Rheumatol. 2022. https://doi.org/10.1016/S2665-9913(22)00093-5.

Nanchahal, J.; Ball, C.; Swettenham, J.; Dutton, S.; Barber, V.; Black, J.; Copsey, B.; Dritsaki, M.; Taylor, P.; Gray, A.; Feldmann, M.; Lamb, S. Study Protocol: A Multi-Centre, Double Blind, Randomised, Placebo-Controlled, Parallel Group, Phase II Trial (RIDD) to Determine the Efficacy of Intra-Nodular Injection of Anti-TNF to Control Disease Progression in Early Dupuytren's Disease, with an Embedded Dose Response Study. Wellcome Open Res. 2017, 2, 37. https://doi.org/10.1288/wellcomeopenres. 11466. 1.

Ng, M.; Thakkar, D.; Southam, L.; Werker, P.; Ophoff, R.; Becker, K.; Nothnagel, M.; Franke, A.; Nürnberg, P.; Espirito-Santo, A. I.; Izadi, D.; Hennies, H. C.; Nanchahal, J.; Zeggini, E.; Furniss, D. A Genome-Wide Association Study of Dupuytren Disease Reveals 17 Additional Variants Implicated in Fibrosis. Am. J. Hum. Genet. 2017, 101 (3), 417-427. https://doi.org/10.1016/j.ajhg.2017.08.006.

(56) References Cited

OTHER PUBLICATIONS

Ortí-Casañ, N.; Wu, Y.; Naudé, P. J. W.; De Deyn, P. P.; Zuhorn, I. S.; Eisel, U. L. M. Targeting TNFR2 as a Novel Therapeutic Strategy for Alzheimer's Disease. Frontiers in Neuroscience. Frontiers Media S.A. 2019. https://doi.org/10.3389/fnins.2019.00049.

Pavelic, S. K.; Sedic, M.; Hock, K.; Vucinic, S.; Jurisic, D.; Gehrig, P.; Scott, M.; Schlapbach, R.; Cacev, T.; Kapitanovic, S.; Pavelic, K. An Integrated Proteomics Approach for Studying the Molecular Pathogenesis of Dupuytren's Disease. J. Pathol. 2009, 217 (4), 524-533. https://doi.org/10.1002/path.2483.

Quispe, C.; Villalobos, M.; Bórquez, J.; Simirgiotis, M. Chemical Composition and Antioxidant Activity of Aloe Vera from the Pica Oasis (Tarapacá, Chile) by UHPLC-Q/Orbitrap/MS/MS. J. Chem. 2018, 2018. https://doi.org/10.1155/2018/6123850.

Ratajczak-Wielgomas, K.; Gosk, J.; Rabczyński, J.; Augoff, K.; Podhorska-Okolów, M.; Gamian, A.; Rutowski, R. Expression of MMP-2, TIMP-2, TGF-B1, and Decorin in Dupuytren's Contracture. Connect. Tissue Res. 2012, 53 (6), 469-477. https://doi.org/10.3109/03008207.2012.686542.

Ratkaj, I.; Bujak, M.; Jurišić, D.; Loncar, M. B.; Bendelja, K.; Pavelić, K.; Pavelić, S. K. Microarray Analysis of Dupuytren's Disease Cells: The Profibrogenic Role of the TGF-β Inducible P38 MAPK Pathway. Cell. Physiol. Biochem. 2012, 30 (4), 927-942. https://doi.org/10.1159/000341470.

Repurposing Anti-TNF for Treating Dupuytren's Disease—Oxford Univeristy—ClinicalTrials.gov (https://clinicaltrials.gov/ct2/show/NCT03180957) downloaded Dec. 26, 2021.

Roach, K. M.; Feghali-Bostwick, C. A.; Amrani, Y.; Bradding, P. Lipoxin A 4 Attenuates Constitutive and TGF-B1—Dependent Profibrotic Activity in Human Lung Myofibroblasts. J. Immunol. 2015, 195 (6), 2852-2860. https://doi.org/10.4049/jimmunol.1500936.

Roell, K. R.; Reif, D. M.; Motsinger-Reif, A. A. An Introduction to Terminology and Methodology of Chemical Synergy-Perspectives from across Disciplines. Frontiers in Pharmacology. Frontiers Research Foundation Apr. 20, 2017. https://doi.org/10.3389/fphar.2017.00158.

Russo, B.; Brambilla, N. C.; Chizzolini, C. Interplay between Keratinocytes and Fibroblasts: A Systematic Review Providing a New Angle for Understanding Skin Fibrotic Disorders. Frontiers in Immunology. Frontiers Media S.A. 2020. https://doi.org/10.3389/fimmu.2020.00648.

Russo, E. B. Taming THC: Potential Cannabis Synergy and Phytocannabinoid-Terpenoid Entourage Effects Linked Articles. Br. J Pharmacol. 2011, 163, 1344-1364. https://doi.org/10.1111/bph.2011.163.issue-7.

Sakkou, M.; Chouvardas, P.; Ntari, L.; Prados, A.; Moreth, K.; Fuchs, H.; Gailus-Dumer, V.; Hrabe de Angelis, M.; Denis, M. C.; Karagianni, N.; Kollias, G. Mesenchymal TNFR2 Promotes the Development of Polyarthritis and Comorbid Heart Valve Stenosis. JCI insight 2018, 3 (7). https://doi.org/10.1172/jci.insight.98864.

Salari, N.; Heydari, M.; Hassanabadi, M.; Kazeminia, M.; Farshchian, N.; Niaparast, M.; Solaymaninasab, Y.; Mohammadi, M.; Shohaimi, S.; Daneshkhah, A. The Worldwide Prevalence of the Dupuytren Disease: A Comprehensive Systematic Review and Meta-Analysis. J. Orthop. Surg. Res. 2020, 15 (1). https://doi.org/10.1186/s13018-020-01999-7.

Salas-Oropeza, J.; Jimenez-Estrada, M.; Perez-Torres, A.; Castell-Rodriguez, A. E.; Becerril-Millan, R.; Rodriguez-Monroy, M. A.; Jarquin-Yañez, K.; Canales-Martinez, M. M. Wound Healing Activity of α-Pinene and α-Phellandrene. Molecules 2021, 26 (9). https://doi.org/10.3390/molecules26092488.

Sánchez, M.; González-Burgos, E.; Iglesias, I.; Gó-Serranillos, M. P. Pharmacological Update Properties of Aloe Vera and Its Major Active Constituents. Molecules. MDPI AG Mar. 2, 2020. https://doi.org/10.3390/molecules25061324.

Satish, L.; Gallo, P. H.; Baratz, M. E.; Johnson, S.; Kathju, S. Reversal of TGF-1 stimulation of-Smooth Muscle Actin and Extracellular Matrix Components by Cyclic AMP in Dupuytren's—Derived Fibroblasts. BMC Musculoskelet. Disord. 2011, 12. https://doi.org/10.1186/1471-2474-12-113.

Sieber, P.; Schäfer, A.; Lieberherr, R.; Le Goff, F.; Stritt, M.; Welford, R. W. D.; Gatfield, J.; Peter, O.; Nayler, O.; Lüthi, U. Novel High-Throughput Myofibroblast Assays Identify Agonists with Therapeutic Potential in Pulmonary Fibrosis That Act via EP2 and EP 4 Receptors. PLoS One 2018, 13 (11). https://doi.org/10.1371/journal.pone.0207872.

Srinivas, S.; Sironmani, T. A.; Shanmugam, G. Dimethyl Sulfoxide Inhibits the Expression of Early Growth-Response Genes and Arrests Fibroblasts at Quiescence. Exp. Cell Res. 1991, 196 (2), 279-286. https://doi.org/10.1016/0014-4827(91)90262-S [Abstract Only].

Tai, Y.; Woods, E. L.; Dally, J.; Kong, D.; Steadman, R.; Moseley, R.; Midgley, A. C. Myofibroblasts: Function, Formation, and Scope of Molecular Therapies for Skin Fibrosis. Biomolecules. MDPI Aug. 1, 2021. https://doi.org/10.3390/biom11081095.

Theiss, A. L.; Simmons, J. G.; Jobin, C.; Lund, P. K. Tumor Necrosis Factor (TNF) αIncreases Collagen Accumulation and Proliferation in Intestinal Myofibroblasts via TNF Receptor 2. J. Biol. Chem. 2005, 280 (43), 36099-36109. https://doi.org/10.1074/jbc.M505291200.

Tomasek, J. J.; Gabbiani, G.; Hinz, B.; Chaponnier, C.; Brown, R. A. Myofibroblasts and Mechano: Regulation of Connective Tissue Remodelling. Nature Reviews Molecular Cell Biology. 2002, pp. 349-363. https://doi.org/10.1038/nrm809.

Tripoli, M.; Cordova, A.; Moschella, F. Update on the Role of Molecular Factors and Fibroblasts in the Pathogenesis of Dupuytren's Disease. J. Cell Commun. Signal. 2016, 10 (4), 315-330. https://doi.org/10.1007/s12079-016-0331-0.

Udalova, I.; Monaco, C.; Nanchahal, J.; Feldmann, M. Anti-TNF Therapy. Microbiol. Spectr. 2016, 4 (4). https://doi.org/10.1128/microbiolspec.mchd-0022-2015.

Verjee, L. S.; Verhoekx, J. S. N.; Chan, J. K. K.; Krausgruber, T.; Nicolaidou, V.; Izadi, D.; Davidson, D.; Feldmann, M.; Midwood, K. S.; Nanchahal, J. Unraveling the Signaling Pathways Promoting Fibrosis in Dupuytren's Disease Reveals TNF as a Therapeutic Target. Proc. Natl. Acad. Sci. U. S. A. 2013, 110 (10). https://doi.org/10.1073/pnas.1301100110.

Wajant, H.; Siegmund, D. TNFR1 and TNFR2 in the Control of the Life and Death Balance of Macrophages. Frontiers in Cell and Developmental Biology. Frontiers Media S.A. 2019. https://doi.org/10.3389/fcell.2019.00091.

Wallach-Dayan, S. B.; Rojas, M. Senescence, the Janus of Lung Injury and Repair. American Journal of Respiratory Cell and Molecular Biology. American Thoracic Society May 1, 2020, pp. 548-549. https://doi.org/10.1165/rcmb.2020-0022ED.

Wooten, D. J.; Meyer, C. T.; Lubbock, A. L. R.; Quaranta, V.; Lopez, C. F. MuSyC Is a Consensus Framework That Unifies Multi-Drug Synergy Metrics for Combinatorial Drug Discovery. Nat. Commun. 2021, 12(1). https://doi.org/10.1038/S41467-021-24789-z.

Wynn, T., Ramalingam, T. Mechanisms of fibrosis: therapeutic translation for fibrotic disease. Nat Med 18, 1028-1040 (2012). https://doi.org/10.1038/nm.2807.

Xu, Q.; Li, M.; Yang, M.; Yang, J.; Xie, J.; Lu, X.; Wang, F.; Chen, W. α-Pinene Regulates MiR-221 and Induces G2/M Phase Cell Cycle Arrest in Human Hepatocellular Carcinoma Cells. Biosci. Rep. 2018, 38 (6). https://doi.org/10.1042/BSR20180980.

Yadav, B.; Wennerberg, K.; Aittokallio, T.; Tang, J. Searching for Drug Synergy in Complex Dose-Response Landscapes Using an Interaction Potency Model. Comput. Struct. Biotechnol. J. 2015, 13, 504-513. https://doi.org/10.1016/j.csbj.2015.09.001.

Yang, H.; Woo, J.; Pae, A. N.; Um, M. Y.; Cho, N. C.; Park, K. D.; Yoon, M.; Kim, J.; Lee, C. J.; Cho, S. α-Pinene, a Major Constituent of Pine Tree Oils, Enhances Non-Rapid Eye Movement Sleep in Mice through GABAA-Benzodiazepine Receptors. Mol. Pharmacol. 2016, 90 (5), 530-539. https://doi.org/10.1124/mol.116.105080.

Yang, S.; Wang, J.; Brand, D. D.; Zheng, S. G. Role of TNF-TNF Receptor 2 Signal in Regulatory T Cells and Its Therapeutic Implications. Frontiers in Immunology. Frontiers Media S.A. Apr. 19, 2018. https://doi.org/10.3389/fimmu.2018.00784.

(56) References Cited

OTHER PUBLICATIONS

Zebib, B.; Beyrouthy, M. E. L.; Sarfi, C.; Merah, O. Chemical Composition of the Essential Oil of Satureja Myrtifolia (Boiss. & Hohen.) from Lebanon. J. Essent. Oil-Bearing Plants 2015, 18 (1), 248-254. https://doi.org/10.1080/0972060X.2014.890075.

Zhang F, Qin F, Yuan J. Molecular Mechanisms and Current Pharmacotherapy of Peyronie's Disease: A Review. Front Pharmacol. 2021; 12:643641 Published May 20, 2021 doi:10.3389/fphar.2021 643641.

* cited by examiner

TOPICAL COMPOSITIONS, PROCESS OF LARGE-SCALE MANUFACTURE, AND METHOD OF USE

CROSS-REFERENCE TO RELATED APPLICATIONS

This is a Continuation-In-Part patent application, which claims the benefit of U.S. application Ser. No. 16/198,793, filed Nov. 22, 2018, which claims the benefit of U.S. Provisional Application No. 62/590,251, which was filed on Nov. 22, 2017. Each of these applications is incorporated by reference herein in its entirety.

BACKGROUND OF INVENTION

Field of the Invention

The application discloses compositions for treatment of topical orphan diseases and related syndromes, and methods of treatment and process of manufacture of disclosed compositions.

Description of the Related Art

Treatments for orphan diseases poses problems not associated with more frequent diseases. First, since few people are inflected, there is little awareness of their problems, so few treatments are investigated. Additionally the low frequency of occurrence hinders the development of these treatments due to the feeling that it will be difficult for a company to recover the high costs of development.

An orphan disease is defined as a condition that affects fewer than 200,000 people nationwide. Collectively, however, they affect as many as 25 million Americans, according to the National Institutes of Health (NIH), and that makes the diseases—and finding treatments for them—a serious public health concern.

Orphan diseases include several well-known diseases, like cystic fibrosis and Tourette's syndrome, but most are unknown to the general public. The orphan diseases of interest in this application are Dupuytren's Contracture, Peyronie's Disease, Scleroderma, Raynaud's (or Renaud's) Phenomenon, Chemotherapy/Radiation Induced Oral Mucosal Ulceration, and Aphthous Ulcers; and more frequent skin issues of Skin Damage from Cuts, Abrasions, and Burns; Aging Skin Changes, and Toe Nail Fungus.

Patients diagnosed with a rare disease are often denied access to effective medicines because prescription drug manufacturers rarely could make a profit from marketing drugs to such small groups. Consequently, the prescription drug industry has not adequately funded research for orphan product development. Despite the urgent health need for these medicines, they came to be known as orphans because companies were not interested in adopting them.

Dupuytren's Contracture is one of the diseases with few people but who suffer great pain and difficulty with life. About 15 million Americans age 35 and older have Dupuytren disease, which is about 5% of the US population. 3 million in the US have bent fingers from Dupuytren disease and 750,000 Americans have severe Dupuytren biology and the risk of being crippled even with available treatment. After age 55, the percent of people with Dupuytren disease increases steadily in both men and women. By age 70, one-quarter of men have signs of Dupuytren, increasing to one-third by age 80. Dupuytren is more common in women than men in those 85 and older.

The total number of US Dupuytren cases increased from 14.2 million in 2000 to 16.2 million people in 2010. The percent of the US population 35 and older affected with Dupuytren disease increased from 8.7% in 2000 to 9.3% in 2010.

Dupuytren's Contracture is a rare connective tissue disorder characterized by fixation of the joints of certain fingers in a permanently flexed position. Due to abnormal thickening and shortening of the bands of fibrous tissue beneath the skin of the palm, a hardened nodule may develop, eventually forming an abnormal band of hardened fibrotic tissue. This causes the fingers of the affected area to begin to be drawn in toward the palm over several months or years and cannot be pulled back. The skin of the affected area may pucker. The ring and pinky fingers are most affected and usually both hands are affected.

Peyronie disease is similar to Dupuytren's Contracture as both involve a connective tissue disorder. Peyronie disease is characterized by the development of fibrous plaques in the soft tissue of the penis of adult males which results in penile deformity. It is estimated to affect 0.5% adult males in the United States, although it is difficult to know the actual extent due to the hesitancy of disclosing the problem. Affected individuals may experience pain, have cord-like lesions on the penis, and exhibit abnormal curvature of the penis when erect. The abnormal curvature of the penis may make it impossible for affected individuals to have normal sexual intercourse.

Scleroderma is a rare, chronic disease of the immune system, blood vessels and connective tissue. 2.5 million people worldwide have scleroderma with an estimated 300,000 people in the United States. The disease is three to four times more common in females than in males. Scleroderma may occur at any age but the symptoms most frequently begin during midlife. The symptoms of scleroderma are similar to those of other autoimmune diseases so diagnosis is difficult.

Scleroderma is an autoimmune connective tissue disorder characterized by abnormal thickening of the skin. Connective tissue is composed of collagen, which supports and binds other body tissues. Some types of scleroderma affect certain, specific parts of the body, while other types can affect the whole body and internal organs. The exact cause of scleroderma is unknown.

The early symptoms of scleroderma vary considerably but distinctive abnormalities on the skin usually appear later in the course of the disease. Common symptoms include painful joints, morning stiffness, fatigue, and weight loss. People with scleroderma have areas of skin that become hard and leathery. These areas of hardness are widespread and typically appear on both sides of the body. Eventually, tissue loss occurs and the skin becomes more highly colored. The skin can become thin, shiny, and bright which results in decreased function of the fingers and toes.

Treatment of scleroderma is usually just symptomatic and supportive. Medications can be given to control the hardening of the skin, although not very effective, and skin care may include lubricating creams or antibiotic ointments for infected ulcerations.

Another orphan disease, Raynaud's phenomenon, can be associated with scleroderma, although it can occur in people without scleroderma. Raynaud's phenomenon is a vascular disorder characterized by the intermittent loss of blood to various parts of the body, particularly the fingers, toes, nose, and ears causing them to turn white. This typically occurs after exposure to cold and causes tingling sensations, numbness, and pain. Raynaud's phenomenon is an early complaint of people with scleroderma. Drug therapy with Vasodilators may help widen the blood vessels.

An estimated 28 million people in the US have Raynaud's phenomenon. The major symptom is a dramatic stark white pallor of the affected areas when exposed to cold, although a blue or red color may also be present from time to time. Other symptoms include a feeling of numbness, severe aching or pain, tingling or throbbing, a sensation of tightness, "pins and needles," and a profound loss of sensation.

Another condition that causes severe pain and difficulty is oral mucosa! ulceration induced chemotherapy/radiation. Although it is not a disease itself, oral mucosa! ulceration is a result of treatments for cancer. Radiation-induced oral mucosa! ulceration occurs in up to 80% of head and neck cancer irradiated patients and reaches up to 100% in patients with altered fractionation head and neck cancer.

Radiation-induced oral mucosa! ulceration is a major dose-limiting toxicity in head and neck cancer patients. It is a normal tissue injury caused by radiation, which has marked adverse effects on patient quality of life and cancer therapy continuity. It is a challenge for proper treatment since it leads to cancer therapy interruption, poor local tumor control, and changes in dose fractionation. Its economic cost is estimated to be about 17,000 dollars per patient with head and neck cancers.

Aphthous Ulcers (also called canker sores) are similar to the oral mucosa! ulceration caused by cancer treatments, but occur in people without a known cause. Aphthous ulcers are small, shallow lesions that develop on the soft tissues in the mouth or at the base of the gums. Aphthous ulcers do not occur on the surface of the lips and they are not contagious. However, they are painful and can make eating difficult. Most sores disappear on their own in a week or two, but some can last longer.

The aphthous ulcers are round or oval with a white or yellow center and a red border. They form inside the mouth; on or under the tongue; inside the cheeks or lips, at the base of the gums; or on the soft palate. There is also a tingling or burning sensation a day or two before the sores appear.

Another problem with treating these orphan diseases was the inability to furnish compositions with sufficient concentrations of active ingredients. Additionally, some of the active ingredients were hydrophilic and other active ingredients were hydrophobic. It is difficult to apply hydrophilic and hydrophobic ingredients at the same time in sufficient concentrations as to be effective against the disease.

Previously, the hydrophilic and hydrophobic ingredients would separate before application, which prevented their combined use. The investigator of this application was able to solve this formulation problem that had plagued other researchers. Additionally, the disclosed process of manufacture presented unexpected results in both ingredient concentration and compatibility.

Additionally, it was discovered during the development of the disclosed compositions and treatments that the compositions were additionally effective against more common skin and oral problems. Variations of the compositions for the orphan diseases were able to treat skin damage from cuts, abrasions, and burns; aging skin changes; and toe nail fungus. This discovery increased the population who could be helped by these compositions.

The disclosed compositions and methods relate to treating medical conditions that are known to have few, if any, effective treatments currently available. There are many medical conditions that exist today without currently demonstrated effective medical treatments that are the subject of extensive research by major pharmaceutical companies throughout the world. The goal is to develop potentially beneficial, skin care compositions that demonstrate new effectiveness following composition component alteration and manufacturing in multiple medical conditions without known and effective treatments.

BRIEF SUMMARY OF THE INVENTION

Tables 1 and 2 provide the percentage of hydrophobic and hydrophilic components in a disclosed composition.

TABLE 1

| Hydrophobic Components | Function | Component % of Composition |
|---|---|---|
| a-Pinene (APN) | anti-inflammatory, anti-microbial | 0.00% to 50.00% |
| Acai Berry | anti-inflammatory | 0.00% to 50.00% |
| Anethole Anise Camphor | anti-microbial | 0.00% to 50.00% |
| Apricot Kernal Oil (AKO) | functional oil | 0.00% to 50.00% |
| Argan Nut Oil (AGN) | skin disorders | 0.00% to 50.00% |
| Baobab Oil (BAB) | moisturizer | 0.00% to 50.00% |
| Bees Wax (BW) | phase change emulsion | 0.00% to 50.00% |
| Benzoin (BZN) | thickener | 0.00% to 50.00% |
| Benzyl Alcohol (BA) | solvent, low toxicity | 0.00% to 50.00% |
| Black Cumin Seed (*Nigella sativa*) | oil | 0.00% to 50.00% |
| Cabreuva Oil | anti-microbial | 0.00% to 50.00% |
| Caffeic acid | anti-oxidant | 0.00% to 50.00% |
| *Calendula* Oil (CDA) | anti-inflammatory | 0.00% to 50.00% |
| *Camellia* Oil (CMA) | anti-oxidant | 0.00% to 50.00% |
| Capaiba Oil (CPO) | anti-inflammatory | 0.00% to 50.00% |
| Caprylic, Capric Triglyceride (CCT) | soft skin | 0.00% to 50.00% |
| Carvacrol (CVC) | anti-microbial | 0.00% to 50.00% |
| Carvone Oil (CRV) | fragrance | 0.00% to 50.00% |
| Caryophyllene (CAP) | anti-oxidant | 0.00% to 50.00% |
| Cedarwood essential Oil | flavor | 0.00% to 50.00% |
| Cetyl Alcohol (CTA) | alcohol | 0.00% to 50.00% |
| Chamomile German Oil (CGB) | fragrance | 0.00% to 50.00% |
| Elemi Oil (EMO) | functional oil | 0.00% to 50.00% |
| Geranium Oil (GER) | essential oil | 0.00% to 50.00% |
| Ghana Shea Butter (GSB) | salve, moisturize | 0.00% to 50.00% |
| Glycerol (GYO) | moisturizer, solvent | 0.00% to 50.00% |
| Ho Wood Oil (HWO) | fragrance | 0.00% to 50.00% |
| Jasmine Oil (JAS) | essential oil | 0.00% to 50.00% |
| Kaempferol | anti-oxidant | 0.00% to 50.00% |
| Kanuka Oil (KNO) | functional oil | 0.00% to 50.00% |
| Lavandin Oil (LVO) | fragrance | 0.00% to 50.00% |
| Limonene Oil (LMN) | fragrance | 0.00% to 50.00% |
| *Litsea Cubeba* Oil (LCO) | functional oil | 0.00% to 50.00% |
| Marula Oil (MRL) | moisture, anti-oxidant | 0.00% to 50.00% |
| Myrrh | anti-inflammatory | 0.00% to 50.00% |
| Nerolina Oil (NRL) | fragrance | 0.00% to 50.00% |
| Niaouli Oil | anti-microbial | 0.00% to 50.00% |
| Palmarosa Oil (PLO) | traditional, anti-microbial | 0.00% to 50.00% |
| Palo Santo | functional oil | 0.00% to 50.00% |
| Panthenol (PNT) | alcohol | 0.00% to 50.00% |
| Peppermint | fragrance | 0.00% to 50.00% |
| Rose Hip Oil (RHO) | healing, anti-inflammatory | 0.00% to 50.00% |
| Rosemary Oil (RMO) | floral | 0.00% to 50.00% |
| Sacha Inchi Oil (SIO) | supportive skin care | 0.00% to 50.00% |
| Sea Buckthorn Oil (SBO) | repair, anti-oxidant | 0.00% to 50.00% |
| Tamanu Oil (TMU) | skin care | 0.00% to 50.00% |
| Terpineol | fragrance | 0.00% to 50.00% |
| Thyme Red, White | anti-microbial | 0.00% to 50.00% |
| Vetiver | fragrance | 0.00% to 50.00% |
| Vitamin E (VTE) | cell reactions, anti-oxidant | 0.00% to 50.00% |
| Winter Savory | anti-microbial | 0.00% to 50.00% |

TABLE 2

| Hydrophilic Components | Function | Component % of Composition |
|---|---|---|
| 1-Tetradecanol | moisturizer | 0.00% to 50.00% |
| *Agave* (AGV) | cell nutrients, fructose, sucrose | 0.00% to 50.00% |
| Alanine (ALA) | amino acid for collagen | 0.00% to 50.00% |
| *Aloe Vera* Gel (AVG) | skin healing, anti-inflammatory | 0.00% to 50.00% |
| Arginine (ARG) | amino acid | 0.00% to 50.00% |
| Artie Fish Collagen (AFC) | critical soluble protein | 0.00% to 50.00% |
| Benzocaine (BZC) | topical analgesic | 0.00% to 50.00% |
| Distilled water | solvent | 0.00% to 50.00% |
| Ferulic Acid (FRA) | anti-oxidant | 0.00% to 50.00% |
| Glutamine (GLU) | amino acid | 0.00% to 50.00% |
| Glycine (GLY) | amino acid for collagen | 0.00% to 50.00% |
| Histidine (HST) | amino acid | 0.00% to 50.00% |
| Hydroxyproline (HDP) | amino acid | 0.00% to 50.00% |
| Isoleucine (ISL) | amino acid | 0.00% to 50.00% |
| Lecithin (LCT) | skin soft and smooth | 0.00% to 50.00% |
| Leucine (LUC) | amino acid | 0.00% to 50.00% |
| Linoleic Acid (LOA) | anti-inflammatory | 0.00% to 50.00% |
| Lysine (LYS) | amino acid | 0.00% to 50.00% |
| Methyl sulfonyl methane (MSM) | transport | 0.00% to 50.00% |
| Niacinamide (NCM) | vitamin b3, no flush | 0.00% to 50.00% |
| Oleic Acid (OLA) | anti-inflammatory | 0.00% to 50.00% |
| Praline (PRL) | amino acid for collagen | 0.00% to 50.00% |
| Protocatechuic Acid (PCT) | anti-oxidant | 0.00% to 50.00% |
| Sericin | gel | 0.00% to 50.00% |
| Sodium Polyacrylate | moisturizer | 0.00% to 50.00% |
| Vitamin A (VTA) | vitamin | 0.00% to 50.00% |
| Vitamin B3 (VTB3) or Niacin | vitamin b3 skin health, vasodilate | 0.00% to 50.00% |
| Vitamin C (VTC) | tissue repair, anti-oxidant | 0.00% to 50.00% |

The meaning of the stated range of 0.00% to 50.00% is that every value from 0.00 to 50.00 to the 0.01 place is disclosed and any range combining any two values in the range is possible. Thus, each whole number 0, 1, 2, 3 . . . 46, 47, 48, 49, 50 is disclosed. Additionally, every 0.1 unit between each whole number is disclosed. Therefore, between each whole number the values of 0.1, 0.2, 0.3 . . . 0.6, 0.7, 0.8, and 0.9 are disclosed. Additionally, every 0.01 unit between each 0.1 is disclosed. Therefore, between each 0.1 unit the values of 0.01, 0.02, 0.03 . . . 0.06, 0.07, 0.08, 0.09 are disclosed.

The stated range of 0.00% to 50.00% includes any range within this range. This range includes 5,000 values—0.00, 0.001 . . . 49.98, 49.99, 50.00. Therefore, the 12,502,500 different ranges possible by stating a minimum value and maximum value are disclosed by the stated range of 0.00% to 50.00%.

The temperatures in the method can be modified depending on the component being combined and the final format of the composition. The temperature can be given as less than or equal to a value. The temperature can be given as greater than or equal to a value. The temperatures can be given as a range between any two disclosed values.

In one embodiment the composition can be a lotion, solution, balm, cream, spray or other consistency used for topical application.

In embodiment the composition can be applied topically or oral mucosa! application.

In one embodiment the composition can be a pharmaceutical, medicinal, cosmetic, or over-the-counter.

In one embodiment the amount of a component is in milliliters.

In one embodiment the amount of a component is in grams.

In one embodiment the amount of a component is in percent of total.

In one embodiment the amount of a-Pinene is from 30 ml to 90 ml per batch of composition. In another embodiment the amount of a-Pinene is from 50 ml to 70 ml per batch of composition. In another embodiment the amount of a-Pinene is 60 ml per batch of composition.

In one embodiment the amount of 1-Tetradecanol is from 1.0 g to 5.0 g per batch of composition. In another embodiment the amount of 1-Tetradecanol is from 1.5 g to 3.5 g per batch of composition. In another embodiment the amount of 1-Tetradecanol is 2.5 g per batch of composition.

In one embodiment the amount of Acai Berry is from 1 ml to 20 ml per batch of composition. In another embodiment the amount of Acai Berry is from 5 ml to 15 ml per batch of composition. In another embodiment the amount of Acai Berry is 10 ml per batch of composition.

In one embodiment the amount of Artie Fish Collagen is from 10 g to 70 g per batch of composition. In another embodiment the amount of Artie Fish Collagen is from 30 g to 50 g per batch of composition. In another embodiment the amount of Artie Fish Collagen is 40 g per batch of composition.

In one embodiment the amount of Agave nectar is from 1 ml to 20 ml per batch of composition. In another embodiment the amount of Agave nectar is from 5 ml to 15 ml per batch of composition. In another embodiment the amount of Agave nectar is 10 ml per batch of composition.

In one embodiment the amount of Alanine is from 1 g to 10 g per batch of composition. In another embodiment the amount of Alanine is from 2.5 g to 7.5 g per batch of composition. In another embodiment the amount of Alanine is 5 g per batch of composition.

In one embodiment the amount of Aloe Vera Leaf Gel is from 100 g to 500 g per batch of composition. In another embodiment the amount of Aloe Vera Leaf Gel is from 200 g to 350 g per batch of composition. In another embodiment the amount of Aloe Vera Leaf Gel is 275 g per batch of composition.

In one embodiment the amount of Anethole Anise Camphor is from 1 ml to 10 ml per batch of composition. In another embodiment the amount of Anethole Anise Camphor is from 2.5 ml to 7.5 ml per batch of composition. In another embodiment the amount of Anethole Anise Camphor is 5 ml per batch of composition.

In one embodiment the amount of Apricot Kernal Oil is from 1 ml to 10 ml per batch of composition. In another embodiment the amount of Apricot Kernal Oil is from 2.5 ml to 7.5 ml per batch of composition. In another embodiment the amount of Apricot Kernal Oil is 5 ml per batch of composition.

In one embodiment the amount of Argan Nut Oil is from 0.5 ml to 10 ml per batch of composition. In another embodiment the amount of Argan Nut Oil is from 1.0 ml to 7.5 ml per batch of composition. In another embodiment the amount of Argan Nut Oil is 2.5-5.0 ml per batch of composition.

In one embodiment the amount of Arginine is from 1 g to 10 g per batch of composition. In another embodiment the amount of Arginine is from 2.5 g to 7.5 g per batch of composition. In another embodiment the amount of Arginine is 5 g per batch of composition.

In one embodiment the amount of Baobab Oil is from 0.5 ml to 10 ml per batch of composition. In another embodiment the amount of Baobab Oil is from 1.0 ml to 7.5 ml per batch of composition. In another embodiment the amount of Baobab Oil is 2.5-5.0 ml per batch of composition.

In one embodiment the amount of Bees Wax is from 10 g to 70 g per batch of composition. In another embodiment the amount of Bees Wax is from 30 g to 50 g per batch of composition. In another embodiment the amount of Bees Wax is 40 g per batch of composition.

In one embodiment the amount of Benzocaine is from 1 g to 7 g per batch of composition. In another embodiment the amount of Benzocaine is from 3 g to 5 g per batch of composition. In another embodiment the amount of Benzocaine is 4 g per batch of composition.

In one embodiment the amount of Benzoin is from 1 ml to 7 ml per batch of composition. In another embodiment the amount of Benzoin is from 3 ml to 5 ml per batch of composition. In another embodiment the amount of Benzoin is 4 ml per batch of composition.

In one embodiment the amount of Benzyl Alcohol is from 1 ml to 100 ml per batch of composition. In another embodiment the amount of Benzyl Alcohol is from 25 ml to 75 ml per batch of composition. In another embodiment the amount of Benzyl Alcohol is 50 ml per batch of composition.

In one embodiment the amount of Cabreuva Oil is from 1 ml to 10 ml per batch of composition. In another embodiment the amount of Cabreuva Oil is from 2.5 ml to 7.5 ml per batch of composition. In another embodiment the amount of Cabreuva Oil is 5 ml per batch of composition.

In one embodiment the amount of Caffeic acid is from 1 g to 10 g per batch of composition. In another embodiment the amount of Caffeic acid is from 2.5 g to 7.5 g per batch of composition. In another embodiment the amount of Caffeic acid is 5 g per batch of composition.

In one embodiment the amount of Calendula Oil is from 1 ml to 10 ml per batch of composition. In another embodiment the amount of Calendula Oil is from 2.5 ml to 7.5 ml per batch of composition. In another embodiment the amount of Calendula Oil is 5 ml per batch of composition.

In one embodiment the amount of *Camellia* Oil is from 1 ml to 20 ml per batch of composition. In another embodiment the amount of *Camellia* Oil is from 5 ml to 15 ml per batch of composition. In another embodiment the amount of *Camellia* Oil is 10 ml per batch of composition.

In one embodiment the amount of Capaiba Oil is from 1 ml to 20 ml per batch of composition. In another embodiment the amount of Capaiba Oil is from 5 ml to 15 ml per batch of composition. In another embodiment the amount of Capaiba Oil is 10 ml per batch of composition.

In one embodiment the amount of Caprylic, Capric Triglyceride is from 1 ml to 20 ml per batch of composition. In another embodiment the amount of Caprylic, Capric Triglyceride is from 5 ml to 15 ml per batch of composition. In another embodiment the amount of Caprylic, Capric Triglyceride is 10 ml per batch of composition.

In one embodiment the amount of Carvacrol is from 1 ml to 10 ml per batch of composition. In another embodiment the amount of Carvacrol is from 2.5 ml to 7.5 ml per batch of composition. In another embodiment the amount of Carvacrol is 5 ml per batch of composition.

In one embodiment the amount of Carvone Oil is from 1.0 ml to 5.0 ml per batch of composition. In another embodiment the amount of Carvone Oil is from 1.5 ml to 3.5 ml per batch of composition. In another embodiment the amount of Carvone Oil is 2.5 ml per batch of composition.

In one embodiment the amount of Caryophyllene is from 1 ml to 20 ml per batch of composition. In another embodiment the amount of Caryophyllene is from 5 ml to 15 ml per batch of composition. In another embodiment the amount of Caryophyllene is 10 ml per batch of composition.

In one embodiment the amount of Cedarwood Oil is from 1.0 ml to 5.0 ml per batch of composition. In another embodiment the amount of Cedarwood Oil is from 1.5 ml to 3.5 ml per batch of composition. In another embodiment the amount of Cedarwood Oil is 2.5 ml per batch of composition.

In one embodiment the amount of Cetyl Alcohol is from 10 g to 70 g per batch of composition. In another embodiment the amount of Cetyl Alcohol is from 30 g to 50 g per batch of composition. In another embodiment the amount of Cetyl Alcohol is 40 g per batch of composition.

In one embodiment the amount of Chamomile German Oil is from 1 ml to 20 ml per batch of composition. In another embodiment the amount of Chamomile German Oil is from 5 ml to 15 ml per batch of composition. In another embodiment the amount of Chamomile German Oil is 10 ml per batch of composition.

In one embodiment the amount of Distilled water is from 100 ml to 1,000 ml per batch of composition. In another embodiment the amount of Distilled water is from 250 ml to 750 ml per batch of composition. In another embodiment the amount of Distilled water is 500 ml per batch of composition.

In one embodiment the amount of Elemi Oil is from 1 ml to 10 ml per batch of composition. In another embodiment the amount of Elemi Oil is from 2.5 ml to 7.5 ml per batch of composition. In another embodiment the amount of Elemi Oil is 5 ml per batch of composition.

In one embodiment the amount of Ferulic Acid is from 1 g to 20 g per batch of composition. In another embodiment the amount of Ferulic Acid is from 5 g to 15 g per batch of composition. In another embodiment the amount of Ferulic Acid is 10 g per batch of composition.

In one embodiment the amount of Geranium Oil is from 1.0 ml to 5.0 ml per batch of composition. In another embodiment the amount of Geranium Oil is from 1.5 ml to 3.5 ml per batch of composition. In another embodiment the amount of Geranium Oil is 2.5 ml per batch of composition.

In one embodiment the amount of Ghana Shea Butter is from 100 g to 500 g per batch of composition. In another embodiment the amount of Ghana Shea Butter is from 200 g to 350 g per batch of composition. In another embodiment the amount of Ghana Shea Butter is 275 g per batch of composition.

In one embodiment the amount of Glutamine is from 1 g to 10 g per batch of composition. In another embodiment the amount of Glutamine is from 2.5 g to 7.5 g per batch of composition. In another embodiment the amount of Glutamine is 5 g per batch of composition.

In one embodiment the amount of Glycerol is from 1 ml to 20 ml per batch of composition. In another embodiment the amount of Glycerol is from 5 ml to 15 ml per batch of composition. In another embodiment the amount of Glycerol is 10 ml per batch of composition.

In one embodiment the amount of Glycine is from 1 g to 10 g per batch of composition. In another embodiment the amount of Glycine is from 2.5 g to 7.5 g per batch of composition. In another embodiment the amount of Glycine is 5 g per batch of composition.

In one embodiment the amount of Histidine is from 1 g to 10 g per batch of composition. In another embodiment the amount of Histidine is from 2.5 g to 7.5 g per batch of composition. In another embodiment the amount of Histidine is 5 g per batch of composition.

In one embodiment the amount of Ho Wood Oil is from 1.0 ml to 5.0 ml per batch of composition. In another embodiment the amount of Ho Wood Oil is from 1.5 ml to 3.5 ml per batch of composition. In another embodiment the amount of Ho Wood Oil is 2.5 ml per batch of composition.

In one embodiment the amount of Hydroxyproline is from 1 g to 10 g per batch of composition. In another embodiment the amount of Hydroxyproline is from 2.5 g to 7.5 g per batch of composition. In another embodiment the amount of Hydroxyproline is 5 g per batch of composition.

In one embodiment the amount of Isoleucine is from 1 g to 10 g per batch of composition. In another embodiment the amount of Isoleucine is from 2.5 g to 7.5 g per batch of composition. In another embodiment the amount of Isoleucine is 5 g per batch of composition.

In one embodiment the amount of Jasmine Oil is from 1.0 ml to 5.0 ml per batch of composition. In another embodiment the amount of Jasmine Oil is from 1.5 ml to 3.5 ml per batch of composition. In another embodiment the amount of Jasmine Oil is 2.5 ml per batch of composition.

In one embodiment the amount of Kaempferol is from 1 g to 10 g per batch of composition. In another embodiment the amount of Kaempferol is from 2.5 g to 7.5 g per batch of composition. In another embodiment the amount of Kaempferol is 5 g per batch of composition.

In one embodiment the amount of Kanuka Oil is from 1.0 ml to 5.0 ml per batch of composition. In another embodiment the amount of Kanuka Oil is from 1.5 ml to 3.5 ml per batch of composition. In another embodiment the amount of Kanuka Oil is 2.5 ml per batch of composition.

In one embodiment the amount of Lavodin Oil is from 1 ml to 20 ml per batch of composition. In another embodiment the amount of Lavodin Oil is from 5 ml to 15 ml per batch of composition. In another embodiment the amount of Lavodin Oil is 10 ml per batch of composition.

In one embodiment the amount of Lecithin is from 10 g to 50 g per batch of composition. In another embodiment the amount of Lecithin is from 15 g to 35 g per batch of composition. In another embodiment the amount of Lecithin is 25 g per batch of composition.

In one embodiment the amount of Leucine is from 1 g to 10 g per batch of composition. In another embodiment the amount of Leucine is from 2.5 g to 7.5 g per batch of composition. In another embodiment the amount of Leucine is 5 g per batch of composition.

In one embodiment the amount of Limonene Oil is from 100 ml to 1,000 ml per batch of composition. In another embodiment the amount of Limonene Oil is from 200 ml to 600 ml per batch of composition. In another embodiment the amount of Limonene Oil is 400 ml per batch of composition.

In one embodiment the amount of Linoleic Acid is from 1 ml to 10 ml per batch of composition. In another embodiment the amount of Linoleic Acid is from 2.5 ml to 7.5 ml per batch of composition. In another embodiment the amount of Linoleic Acid is 5 ml per batch of composition.

In one embodiment the amount of Litsea Cubebe Oil is from 1 ml to 10 ml. In another embodiment the amount of Litsea Cubebe Oil is from 2.5 ml to 7.5 ml per batch of composition. In another embodiment the amount of Litsea Cubebe Oil is 5 ml per batch of composition.

In one embodiment the amount of Lysine is from 1 g to 10 g per batch of composition. In another embodiment the amount of Lysine is from 2.5 g to 7.5 g per batch of composition. In another embodiment the amount of Lysine is 5 g per batch of composition.

In one embodiment the amount of Marula Oil is from 1.0 ml to 5.0 ml per batch of composition. In another embodiment the amount of Marula Oil is from 1.5 ml to 3.5 ml per batch of composition. In another embodiment the amount of Marula Oil is 2.5 ml per batch of composition.

In one embodiment the amount of Methyl Sulfonyl Methane is from 10 g to 50 g per batch of composition. In another embodiment the amount of Methyl Sulfonyl Methane is from 10 g to 50 g per batch of composition. In another embodiment the amount of Methyl Sulfonyl Methane is 25 g per batch of composition.

In one embodiment the amount of Myrrh is from 1 ml to 10 ml per batch of composition. In another embodiment the amount of Myrrh is from 2.5 ml to 7.5 ml per batch of composition. In another embodiment the amount of Myrrh is 5 ml per batch of composition.

In one embodiment the amount of Nerolina Oil is from 1.0 ml to 5.0 ml per batch of composition. In another embodiment the amount of Nerolina Oil is from 1.5 ml to 3.5 ml per batch of composition. In another embodiment the amount of Nerolina Oil is 2.5 ml per batch of composition.

In one embodiment the amount of Niacinamide is from 1.0 g to 5.0 g per batch of composition. In another embodiment the amount of Niacinamide is from 1.5 g to 3.5 g per batch of composition. In another embodiment the amount of Niacinamide is 2.5 g per batch of composition.

In one embodiment the amount of Niaouli Oil is from 1 ml to 10 ml per batch of composition. In another embodiment the amount of Niaouli Oil is from 2.5 ml to 7.5 ml per batch of composition. In another embodiment the amount of Niaouli Oil is 5 ml per batch of composition.

In one embodiment the amount of Nigella saliva Black Cumin Seed Oil is from 10 ml to 100 ml per batch of composition. In another embodiment the amount of Nigella saliva Black Cumin Seed Oil is from 25 ml to 75 ml per batch of composition. In another embodiment the amount of Nigella saliva Black Cumin Seed Oil is 50 ml per batch of composition.

In one embodiment the amount of Oleic Acid is from 1 ml to 10 ml per batch of composition. In another embodiment the amount of Oleic Acid is from 2.5 ml to 7.5 ml per batch of composition. In another embodiment the amount of Oleic Acid is 5 ml per batch of composition.

In one embodiment the amount of Palmarosa Oil is from 1.0 ml to 5.0 ml per batch of composition. In another embodiment the amount of Palmarosa Oil is from 1.5 ml to 3.5 ml per batch of composition. In another embodiment the amount of Palmarosa Oil is 2.5 ml per batch of composition.

In one embodiment the amount of Palo Santo is from 1.0% to 5.0% per batch of composition. In another embodiment the amount of Palo Santo is from 1.5% to 3.5% per batch of composition. In another embodiment the amount of Palo Santo is 2.5% per batch of composition.

In one embodiment the amount of Panthenol is from 1 ml to 20 ml per batch of composition. In another embodiment the amount of Panthenol is from 5 ml to 15 ml per batch of composition. In another embodiment the amount of Panthenol is 10 ml per batch of composition.

In one embodiment the amount of Peppermint is from 1 ml to 10 ml per batch of composition. In another embodiment the amount of Peppermint is from 2.5 ml to 7.5 ml per batch of composition. In another embodiment the amount of Peppermint is 5 ml per batch of composition.

In one embodiment the amount of Praline is from 1 g to 10 g per batch of composition. In another embodiment the amount of Praline is from 2.5 g to 7.5 g per batch of composition. In another embodiment the amount of Praline is 5 g per batch of composition.

In one embodiment the amount of Pratocatechuic Acid is from 1 g to 20 g per batch of composition. In another embodiment the amount of Pratocatechuic Acid is from 5 g to 15 g per batch of composition. In another embodiment the amount of Pratocatechuic Acid is 10 g per batch of composition.

In one embodiment the amount of Rose Hip Seed Oil is from 1 ml to 20 ml per batch of composition. In another embodiment the amount of Rose Hip Seed Oil is from 2.5 ml to 15 ml per batch of composition. In another embodiment the amount of Rose Hip Seed Oil is 5-10 ml per batch of composition.

In one embodiment the amount of Sachi Inchi oil is from 1 ml to 10 ml per batch of composition. In another embodiment the amount of Sachi Inchi oil is from 2.5 ml to 7.5 ml per batch of composition. In another embodiment the amount of Sachi Inchi oil is 5 ml per batch of composition.

In one embodiment the amount of Sea Buckthorn Oil is from 1 ml to 10 ml per batch of composition. In another embodiment the amount of Sea Buckthorn Oil is from 2.5 ml to 7.5 ml per batch of composition. In another embodiment the amount of Sea Buckthorn Oil is 5 ml per batch of composition.

In one embodiment the amount of Sericin is from 10 g to 100 g. In another embodiment the amount of Sericin is from 25 g to 75 g per batch of composition. In another embodiment the amount of Sericin is 50 g per batch of composition.

In one embodiment the amount of Sericin is from 5 g to 50 g. In another embodiment the amount of Sericin is from 10 g to 30 g per batch of composition. In another embodiment the amount of Sodium Polyacrylate is 20 g per batch of composition.

In one embodiment the amount of Tamanu Oil is from 1 ml to 10 ml per batch of composition. In another embodiment the amount of Tamanu Oil is from 2.5 ml to 7.5 ml per batch of composition. In another embodiment the amount of Tamanu Oil is 5 ml per batch of composition.

In one embodiment the amount of Terpineol is from 1 ml to 10 ml per batch of composition. In another embodiment the amount of Terpineol is from 2.5 ml to 7.5 ml per batch of composition. In another embodiment the amount of Terpineol is 5 ml per batch of composition.

In one embodiment the amount of Thyme Red, White is from 1 ml to 10 ml per batch of composition. In another embodiment the amount of Thyme Red, White is from 2.5 ml to 7.5 ml per batch of composition. In another embodiment the amount of Thyme Red, White is 5 ml per batch of composition.

In one embodiment the amount of Vetiver is from 1.0 ml to 5.0 ml per batch of composition. In another embodiment the amount of Vetiver is from 1.5 ml to 3.5 ml per batch of composition. In another embodiment the amount of Vetiver is 2.5 ml per batch of composition.

In one embodiment the amount of Vitamin A is from 1.0 g to 5.0 g per batch of composition. In another embodiment the amount of Vitamin A is from 1.5 g to 3.5 g per batch of composition. In another embodiment the amount of Vitamin A is 2.5 g per batch of composition.

In one embodiment the amount of Vitamin B3 or Niacin is from 1 g to 25 g per batch of composition. In another embodiment the amount of Vitamin B3 or Niacin is from 5 g to 17.5 g per batch of composition. In another embodiment the amount of Vitamin B3 or Niacin is 12.5 g per batch of composition.

In one embodiment the amount of Vitamin C is from 1.0 g to 5.0 g per batch of composition. In another embodiment the amount of Vitamin C is from 1.5 g to 3.5 g per batch of composition. In another embodiment the amount of Vitamin C is 2.5 g per batch of composition.

In one embodiment the amount of Vitamin E is from 1.0 g to 5.0 g per batch of composition. In another embodiment the amount of Vitamin E is from 1.5 g to 3.5 g per batch of composition per batch of composition. In another embodiment the amount of Vitamin E is 2.5 g per batch of composition per batch of composition.

In one embodiment the amount of Winter Savory is from 1 ml to 10 ml per batch of composition. In another embodiment the amount of Winter Savory is from 2.5 ml to 7.5 ml per batch of composition. In another embodiment the amount of Winter Savory is 5 ml per batch of composition.

In one embodiment a method of treatment for Dupuytren's Contracture, comprises administering to a mammal in need thereof a composition comprising a combination of components in Table 1 and 2.

In one embodiment a method of treatment for Skin Damage from Cuts, Abrasions, and Burns, comprises administering to a mammal in need thereof a composition comprising a combination of components in Table 1 and 2.

In one embodiment a method of treatment for Peyronie's Disease, comprises administering to a mammal in need thereof a composition comprising a combination of components in Table 1 and 2.

In one embodiment a method of treatment for Aging Skin, comprises administering to a mammal in need thereof a composition comprising a combination of components in Table 1 and 2.

In one embodiment a method of treatment for Toe Nail Fungus, comprises administering to a mammal in need thereof a composition comprising a combination of components in Table 1 and 2.

In one embodiment a method of treatment for Aphthous Ulcers, comprises administering to a mammal in need thereof a composition comprising a combination of components in Table 1 and 2.

In one embodiment a method of treatment for Scleroderma Induced Subcutaneous Damage, comprises administering to a mammal in need thereof a composition comprising a combination of components in Table 1 and 2.

In one embodiment a method of treatment for Raynaud's Phenomenon, comprises administering to a mammal in need thereof a composition comprising a combination of components in Table 1 and 2.

In one embodiment a method of treatment for Chemotherapy/Radiation Induced Oral Mucosa! Ulceration, comprises administering to a mammal in need thereof a composition comprising a combination of components in Table 1 and 2.

Additional embodiments are described in the following paragraphs.

Paragraph 1. A composition comprising a-pinene, ghana shea butter and methylsulfonylmethane.

Paragraph 2. The composition of Paragraph 1 further comprising glycerol, black cumin seed, aloe vera gel, collagen and lecithin.

Paragraph 3. The composition of Paragraph 2 further comprising at least one from the group consisting of functional oil, alcohol, anti-inflammatory, anti-oxidant, antimicrobial, floral, thickener, wax, fragrance, fatty acid, analgesic, amino acid, carbohydrate, vitamin, solvent, gel, moisturizer and acid.

Paragraph 4. The composition of Paragraph 3 wherein the functional oil is selected from the group consisting of Apricot Kernal Oil, Argan Nut Oil, Baobab Oil, Calendula Oil, Camellia Oil, Caprylic, Capric Triglyceride, Caryophyllene, Elemi Oil, Kanuka Oil, Litsea Cubebe Oil, Marula Oil, Palmarosa Oil, Palo Santo, Rose Hip Seed Oil, Sachi Inchi Oil, Sea Buckthorn Oil and Tamanu Oil.

Paragraph 5. The composition of Paragraph 3 wherein the alcohol is selected from the group consisting of Benzyl Alcohol, Cetyl Alcohol and Panthenol.

Paragraph 6. The composition of Paragraph 3 wherein the anti-inflammatory is selected from the group consisting of Acai Berry, Chamomile German Oil, Capaiba Oil, Myrrh, Rose Hip Seed Oil, Oleic Acid and Linoleic Acid.

Paragraph 7. The composition of Paragraph 3 wherein the anti-oxidant is selected from the group consisting of Kaempferol, Caffeic acid and Protocatechuic Acid.

Paragraph 8. The composition of Paragraph 3 wherein the anti-microbial is selected from the group consisting of Anethole Anise Camphor, Cabreuva Oil, Carvacrol, Niaouli Oil, Thyme and Winter Savory.

Paragraph 9. The composition of Paragraph 3 wherein the floral is Rosemary Oil.

Paragraph 10. The composition of Paragraph 3 wherein the thickener is Benzoin.

Paragraph 11. The composition of Paragraph 3 wherein the wax is Bees Wax.

Paragraph 12. The composition of Paragraph 3 wherein the fragrance is selected from the group consisting of Carvone Oil, Geranium Oil, Ho Wood Oil, Jasmine Oil, Lavodin Oil, Limonene Oil, Nerolina Oil, Peppermint, Terpineol and Vetiver.

Paragraph 13. The composition of Paragraph 3 wherein the fatty acid is Ferulic Acid.

Paragraph 14. The composition of Paragraph 3 wherein the analgesic is Benzocaine.

Paragraph 15. The composition of Paragraph 3 wherein the amino acid is selected from the group consisting of Alanine, Arginine, Glutamine, Glycine, Histidine, Hydroxyproline, Isoleucine, Leucine, Lysine and Praline.

Paragraph 16. The composition of Paragraph 3 wherein the carbohydrate is Agave nectar.

Paragraph 17. The composition of Paragraph 3 wherein the vitamin is selected from the group consisting of Vitamin A, Vitamin B3, Niacin, Vitamin C, Vitamin E, Niacinamide.

Paragraph 18. The composition of Paragraph 3 wherein the solvent is distilled water.

Paragraph 19. The composition of Paragraph 3 wherein the gel is Sericin.

Paragraph 20. The composition of Paragraph 3 wherein the moisturizer is selected from the group consisting of Sodium Polyacrylate and 1-Tetradecanol.

Paragraph 21. A method of combining hydrophobic components and hydrophilic components with high dosage of active ingredients, comprising the steps of:
 a) placing hydrophobic components that are a liquid or become a liquid at 45° C. in a first vessel and placing hydrophilic components that are a liquid or become a liquid at 45° C. in a second vessel;
 b) inserting into each of the first vessel and the second vessel a propeller mixer rotating at 400 rotations per minute (RPM) propeller mixing speed and heating each of the first vessel and the second vessel to 45° C.;
 c) after sufficient mixing at 45° C., placing hydrophobic components that are not liquid at 45° C. in the first vessel and placing hydrophilic components that are not liquid at 45° C. in the second vessel, and increasing rotation of each propeller mixer to 800 RPM and increasing the temperature of the first vessel and the second vessel to 60° C.;
 d) after sufficient time for mixing and completion of reaction in the first vessel and the second vessel, pouring the contents of the second vessel into the first vessel and combining the contents of both vessels, and maintaining the rotation of the propeller mixer at 800 RPM and temperature at 60° C. for an additional 20 minutes of reaction time;
 e) adjusting pH to 7.5 with NaOH;
 f) cooling the mixed contents in the first vessel slowly over several hours to ambient temperature by insulating the first vessel and reducing the propeller mixer to 600 RPM;
 g) stopping the propeller mixer after the contents in the first vessel reaches ambient temperature;
 h) filling mixed content into a container.

Paragraph 22. A method of combining hydrophobic components and hydrophilic components with high dosage of active ingredients, comprising the steps of:
 a) placing hydrophobic components that are a liquid or become a liquid at 30° C.-60° C. in a first vessel and placing hydrophilic components that are a liquid or become a liquid at 30° C.-60° C. in a second vessel;
 b) inserting into each of the first vessel and the second vessel a propeller mixer rotating at 200-600 rotations per minute (RPM) propeller mixing speed and heating each of the first vessel and the second vessel to 30° C.-60° C.;
 c) after sufficient mixing at 30° C.-60° C., placing hydrophobic components that are not liquid at 30° C.-60° C. in the first vessel and placing hydrophilic components that are not liquid at 30° C.-60° C. in the second vessel, and increasing rotation of each propeller mixer to 600-1,000 RPM and increasing the temperature of the first vessel and the second vessel to greater than or equal to 60° C.;
 d) after sufficient time for mixing and completion of reaction in the first vessel and the second vessel, pouring the contents of the second vessel into the first vessel and combining the contents of both vessels, and maintaining the rotation of the propeller mixer at 600-1,000 RPM and temperature at greater than or equal to 60° C. for an additional 10-60 minutes of reaction time;
 e) adjusting pH to 7.5 with NaOH;
 f) cooling the mixed contents in the first vessel slowly over several hours to ambient temperature by insulating the first vessel and reducing the propeller mixer speed to 400-800 RPM;
 g) stopping the propeller mixer after the contents in the first vessel reaches ambient temperature;
 h) filling mixed content into a container.

Paragraph 23. The method of combining hydrophobic components and hydrophilic components with high dosage of active ingredients in Paragraph 22, wherein the temperature in step a) is 40° C.-50° C.

Paragraph 24. The method of combining hydrophobic components and hydrophilic components with high dosage of active ingredients in Paragraph 23, wherein the temperature in step a) is 45° C.

Paragraph 25. The method of combining hydrophobic components and hydrophilic components with high dosage of active ingredients in Paragraph 22, wherein the propeller mixing speed is step b) is 300-500 RPM.

Paragraph 26. The method of combining hydrophobic components and hydrophilic components with high dosage of active ingredients in Paragraph 25, wherein the propeller mixing speed is step b) is 400 RPM.

Paragraph 27. The method of combining hydrophobic components and hydrophilic components with high dosage of active ingredients in Paragraph 22, wherein the temperature in step b) is 40° C.-50° C.

Paragraph 28. The method of combining hydrophobic components and hydrophilic components with high dosage of active ingredients in Paragraph 27, wherein the temperature in step b) is 45° C.

Paragraph 29. The method of combining hydrophobic components and hydrophilic components with high dosage of active ingredients in Paragraph 22, wherein the temperature in step c) is 40° C.-50° C.

Paragraph 30. The method of combining hydrophobic components and hydrophilic components with high dosage of active ingredients in Paragraph 29, wherein the temperature in step C) is 45° C.

Paragraph 31. The method of combining hydrophobic components and hydrophilic components with high dosage of active ingredients in Paragraph 22, wherein the propeller mixing speed is step c) is 700-900 RPM.

Paragraph 32. The method of combining hydrophobic components and hydrophilic components with high dosage of active ingredients in Paragraph 31, wherein the propeller mixing speed is step c) is 800 RPM.

Paragraph 33. The method of combining hydrophobic components and hydrophilic components with high dosage of active ingredients in Paragraph 22, wherein the temperature in step c) is increased to 60° C.-80° C.

Paragraph 34. The method of combining hydrophobic components and hydrophilic components with high dosage of active ingredients in Paragraph 33, wherein the temperature in step c) is increased to greater than 80° C.

Paragraph 35. The method of combining hydrophobic components and hydrophilic components with high dosage of active ingredients in Paragraph 22, wherein the propeller mixing speed is step d) is 700-900 RPM.

Paragraph 36. The method of combining hydrophobic components and hydrophilic components with high dosage of active ingredients in Paragraph 35, wherein the propeller mixing speed is step d) is 800 RPM.

Paragraph 37. The method of combining hydrophobic components and hydrophilic components with high dosage of active ingredients in Paragraph 22, wherein the temperature in step d) is increased to 60° C.-80° C.

Paragraph 38. The method of combining hydrophobic components and hydrophilic components with high dosage of active ingredients in Paragraph 37, wherein the temperature in step d) is increased to greater than 80° C.

Paragraph 39. The method of combining hydrophobic components and hydrophilic components with high dosage of active ingredients in Paragraph 22, wherein the sufficient time is 1 to 8 hours.

Paragraph 40. The method of combining hydrophobic components and hydrophilic components with high dosage of active ingredients in Paragraph 39, wherein the sufficient time is more than 8 hours.

Paragraph 41. The method of combining hydrophobic components and hydrophilic components with high dosage of active ingredients in Paragraph 22, wherein the additional reaction time is 10-40 minutes.

Paragraph 42. The method of combining hydrophobic components and hydrophilic components with high dosage of active ingredients in Paragraph 41, wherein the additional reaction time is 20 minutes.

Paragraph 43. The method of combining hydrophobic components and hydrophilic components with high dosage of active ingredients in Paragraph 22, wherein the several hours in step f) is 2 to IO hours.

Paragraph 44. The method of combining hydrophobic components and hydrophilic components with high dosage of active ingredients in Paragraph 43, wherein the several hours in step f) is more than 10 hours.

Paragraph 45. The method of combining hydrophobic components and hydrophilic components with high dosage of active ingredients in Paragraph 22, wherein the propeller mixer speed in step f) is 500-700 RPM.

Paragraph 46. The method of combining hydrophobic components and hydrophilic components with high dosage of active ingredients in Paragraph 46, wherein the propeller mixer speed in step f) is 600 RPM.

Paragraph 47. The method of combining hydrophobic components and hydrophilic components with high dosage of active ingredients in Paragraph 22, wherein the ambient temperature in step g) is 25° C.-37° C.

Paragraph 48. The method of combining hydrophobic components and hydrophilic components with high dosage of active ingredients in Paragraph 47, wherein the ambient temperature in step g) is less than 25° C.

The disclosed compositions for treatments of topical diseases and syndromes, many with similarities in terms of their anti-inflammatory and anti-oxidative activities, but also multiple differences in their observed abilities that can be combined to challenge the current, underlying pathophysiology. The following disorders, described below, can be treated with the disclosed compositions with the proper combination and alteration of ingredients:

1. Dupuytren's Contracture
2. Skin Damage from Cuts, Abrasions, and Burns
3. Peyronie's Disease
4. Aging Skin Changes on arms and hands
5. Toe Nail Fungus
6. Aphthous Ulcers
7. Scleroderma Induced Subcutaneous Damage
8. Raynaud's (or Renaud's) Phenomenon
9. Chemotherapy/Radiation Induced Oral Mucosa! Ulceration

DETAILED DESCRIPTION OF THE INVENTION

Components of the Compositions

Figure 1:
FIG. 1 shows a hand with a chord of a patient with Dupytren's Disease and Contracture [permission granted—Frank C. Muller, Baden-Baden].

Table 3 shows the function, and scientific name or chemical formula for each hydrophobic component that can be used in a composition.

TABLE 3

| Hydrophobic Components | Function | Scientific name/Formula |
|---|---|---|
| a-Pinene (APN) | anti-inflammatory, anti-microbe | *Pinophyta* C10H16 |
| Acai Berry | anti-inflammatory | *Euterpe oleracea* |
| Anethole Anise Camphor | anti-microbial | C10H12O |
| Apricot Kernel Oil (AKO) | functional oil | *Prunus armeniaca* |
| Argan Nut Oil (AGN) | skin disorders | *Argania spinosa* |
| Baobab Oil (BAB) | moisturizer | *Adansonia digitata* |
| Bees Wax (BW) | phase change emulsion | *Apis mellifera* |
| Benzoin (BZN) | thickener | *Styrax benzoin* |
| Benzyl Alcohol (BA) | solvent, low toxicity | C6HsCH2OH |
| Black Cumin Seed | oil | *Nigella sativa* |
| Cabreuva Oil | anti-microbial | *Myrocarpusfrondosus* |
| Caffeic acid | anti-oxidant | C9HsO4 |
| *Calendula* Oil (CDA) | anti-inflammatory | *Calendula officinalis* |
| *Camellia* Oil (CMA) | anti-oxidant | *Camellia japonica* |
| Capaiba Oil (CPO) | anti-inflammatory | *Copaifera officinalis* |
| Caprylic, Capric Triglyceride (CCT) | soft skin | *Cocos nucifera* |
| Carvacrol (CVC) | anti-microbial | C10H14O |
| Carvone Oil (CRV) | fragrance | C10H14O |
| Caryophyllene (CAP) | anti-oxidant | *Syzygium aromaticum* |
| Cedarwood essential Oil | flavor | Pine or cypress |
| Cetyl Alcohol (CTA) | alcohol | C16H34O |
| Chamomile German Oil (CGB) | fragrance | *Chamaemelum nobile* |
| Elemi Oil (EMO) | functional oil | *Canarium luzonicum* |
| Geranium Oil (GER) | essential oil | *Pelargonium graveolens* |
| Ghana Shea Butter (GSB) | salve, moisturize | *Vitellaria paradoxa* |
| Glycerol (GYO) | moisturizer, solvent | C3HsO3 |
| Ho Wood Oil (HWO) | fragrance | *Cinnamomum camphora* |
| Jasmine Oil (JAS) | essential oil | *Jasminum officinale* |
| Kaempferol | anti-oxidant | C1sH10O6 |
| Kanuka Oil (KNO) | functional oil | *Kunzea ericoides* |
| Lavandin Oil (LVO) | fragrance | *Lavandin intermedia* |
| Limonene Oil (LMN) | fragrance | C10H16 |
| *Litsea Cubeba* Oil (LCO) | functional oil | *Litsea cubeba* |
| Marula Oil (MRL) | moisture, anti-oxidant | *Sclerocarya birrea* |
| Myrrh | anti-inflammatory | Genus *Commiphora* |
| Nerolina Oil (NRL) | fragrance | *Melaleuca quinquenervia* |
| Niaouli Oil | anti-microbial | *Melaleuca quinquenervia* |
| Palmarosa Oil (PLO) | traditional, anti-microbial | *Cymbopogon martinii* |
| Palo Santo | functional oil | *Bursera graveolens* |
| Panthenol (PNT) | alcohol | C9H19NO4 |
| Peppermint | fragrance | *Mentha x piperita* |

TABLE 3-continued

| Hydrophobic Components | Function | Scientific name/Formula |
|---|---|---|
| Rose Hip Oil (RHO) | healing, moisturizing | *Rosa moschata* & *Rosa rubiginosa* |
| Rosemary Oil (RMO) | floral | *Rosmarinus officinalis*, |
| Sacha Inchi Oil (SIO) | supportive skin care | *Plukenetia volubillis* |
| Sea Buckthorn Oil (SBO) | repair, anti-oxidant | *Hippophae rhamnoides* |
| Tamanu Oil (TMU) | skin care | *Calophyllum inophyllum* |
| Terpineol | fragrance | C10H18O |
| Thyme Red, White | anti-microbial | Genus *Thymus* |
| Vetiver | fragrance | *Chrysopogon zizanioides* |
| Vitamin E (VTE) | cell reactions, anti-oxidant | Tocotrienol, tocopherol |
| Winter Savory | anti-microbial | *Satureja montana* |

Table 4 shows the function, and scientific name or chemical formula for each hydrophilic component that can be used in a composition.

TABLE 4

| Hydrophilic Components | Function | Scientific name |
|---|---|---|
| 1-Tetradecanol | moisturizer | C14H30O |
| *Agave* (AGV) | cell nutrients, fructose, sucrose | *Agave tequilana* weber azul |
| Alanine (ALA) | amino acid for collagen | C3H1NO2 |
| *Aloe Vera* Gel (AVG) | skin healing, anti-inflammatory | *Aloe barbadensis* mil |
| Arginine (ARG) | amino acid | C6H14N4O2 |
| Artie Fish Collagen (AFC) | critical soluble protein | *Arctogadus glacialis* |
| Benzocaine (BZC) | local analgesic | C9H11NO2 |
| Distilled water | solvent | H2O |
| Ferulic Acid (FRA) | anti-oxidant | C10H10O4 |
| Glutamine (GLU) | amino acid | CsH10N2O3 |
| Glycine (GLY) | amino acid for collagen | C2HsNO2 |
| Histidine (HST) | amino acid | C6H9N3O2 |
| Hydroxyproline (HDP) | amino acid | CsH9NO3 |
| Isoleucine (ISL) | amino acid | C6H13NO2 |
| Lecithin (LCT) | skin soft and smooth | *Glycine max* |
| Leucine (LUC) | amino acid | C6H13NO2 |
| Linoleic Acid (LOA) | anti-inflammatory | C18H32O2 |
| Lysine (LYS) | amino acid | C6H14N2O2 |
| Methyl sulfonyl methane (MSM) | transport | C2H6SO2 |
| Niacin (NCN) | vitamin b3 skin health, vasodilate | C6HsNO2 |
| Niacinamide (NCM) | vitamin b3, no flush | C6H6N2O |
| Oleic Acid (OLA) | anti-inflammatory | C18H34O2 |
| Panthenol | alcohol analogue of Vitamin B5 | C9H19NO4 |
| Praline (PRL) | amino acid for collagen | CsH9NO2 |
| Protocatechuic Acid (PCT) | anti-oxidant | C1H6O4 |
| Sericin | gel | C30H40N10O16 |
| Sodium Polyacrylate | moisturizer | (C3H3NaO2)n |
| ethanol | solvent | C2H6O |
| isopropyl alcohol | solvent | C3HsO |
| Vitamin A (VTA) | vitamin | retinal, retinal, retinoic acid, provitamin A carotenoids, beta-carotene |
| Vitamin B3 (VTB3) or Niacin | vitamin b3 skin health, vasodilate | nicotinamide, niacin, nicotinamide riboside |
| Vitamin C (VTC) | tissue repair, anti-oxidant | C6HsO6 |

Hydrophobic Components

Acai Berry—A small, round, black-purple fruit similar in appearance to a grape. The seed makes up about 60-80% of the fruit. The palm bears fruit year round.

a-Pinene—Formula—$C_{10}H_{16}$—a-Pinene is a terpene that is not toxic, which is one of two isomers of this compound with the other being-Pinene that has toxic characteristics. They originate predominantly from conifer pine trees (Pinophyta) and are both natural compositions. a-Pinene has important anti-inflammatory properties working through the PGEl mechanism. In addition, it has important anti-microbial activities. It also been used in medicinal compositions as a bronchial dilator, anti-septic agent, and anti-cancer agent. Its primary use in the composition is its anti-inflammatory and anti-microbial effects.

Anethole Anise Camphor-Formula—$C_{10}H_{12}O$—An organic compound that is widely used as a flavoring. A derivative of phenylpropene, an aromatic compound that occurs widely in nature in essential oils. It is distinctly sweet and pleasant to the taste. It contributes a large component of the odor and flavor of anise and fennel. It is a colorless, fragrant, mildly volatile liquid. Anethole has potent antimicrobial properties. Reported antibacterial properties include both bacteriostatic and bactericidal action. Antifungal activity includes increasing the effectiveness of some other phytochemicals.

Apricot Kernal Oil (AKO)—Pressed from the kernels of the *Prunus armeniaca*. Apricot kernels have an oil content of 40-50%. It is also used to extract an essential oil, which contains amygdalin. The oil is chiefly composed of oleic acid and linoleic acid.

Argan Nut Oil—*Argania spinosa* is an important tree grown in Morocco. It is a dietary oil and used in cosmetics. The oil comes from the tree's nuts. Its intended use for the compositions is to support the oils with higher levels of healing.

Baobab Oil—*Adansonia digitalia* is the most common of the nine species of Baobab trees with the oil extracted from seeds. It is commonly used on the skin as a moisturizer, a stimulant for skin cell replication, a skin anti-oxidant, a wound healing agent, and an anti-inflammatory agent due to its omega fatty acids. Is use in the compositions is primarily for its anti-oxidant, anti-inflammatory, and wound healing properties.

Bees Wax—Wax from honey bees (*Apis mellifera*) is utilized in some of the compositions as a temperature sensitive agent that melts at 58° C. and solidifies at lower temperatures depending upon concentration that keeps the manufacturing process in the liquid phase for alterations and modifications of the natural components at a higher temperature. Upon cooling, it acts with other components to provide solidity within the final composition.

Benzoin (BZN)—*Styrax benzoin*—A balsamic resin obtained from the bark of several species of trees in the genus *Styrax*. It is used in perfumes, incense, flavoring, and medicine. Benzoin is sometimes called gum benzoin or gum benjamin. Benzoin is also called storax. Benzoin has a sweet vanilla-like aroma and fixative properties.

Benzyl Alcohol—Formula C6HsCH20H—Benzyl Alcohol is often used as a solvent due to low toxicity, polarity, and low vapor pressure with moderate solubility in water and miscibility in other alcohols. It is commonly found in plants and fruits and along with a variety of essential oils, such as, jasmine, hyacinth, and ylang-ylang. It is also used as a bacteriostatic preservative in intravenous medications, cosmetics, and skin care compositions. It has a low toxicity value with $LD_{50}$ of 1.2 gm/kg in rats. Its use in the compositions is as a solvent and its anti-microbial properties.

Black Cumin Seed Oil (BCS)—*Nigella sativa*—It is an annual flowering plant in the family Ranunculaceae.

Cabreuva Oil—*Myrocarpus frondosus*—Its aroma is deep and mellow, with a pleasing woodsy, smoky base note that blends very well with most oils. In natural perfumery, clove bud essential oil is used in making floral notes such as rose and lily of the valley, amber bases, precious wood notes, and in Caffeic acid—Formula—$C_9H_8O_4$—An organic compound classified as a hydroxycinnamic acid. It consists of both phenolic and acrylic functional groups. It is found in all plants because it is a key intermediate in the biosynthesis of lignin. Caffeic acid has a variety of potential pharmacological effects and the inhibitory effect of caffeic acid on cancer cell proliferation by an oxidative mechanism. Caffeic acid is an antioxidant, immunomodulatory and anti-inflammatory activity.

Calendula Oil—*Calendula officinalis* is a type of marigold that is used for herbal, cosmetic, and medicinal compositions. The yellow petals are edible and have been used medicinally for centuries. It is currently utilized for its pharmacologic effects for anti-inflammatory, anti-tumor, and wound healing attributes. Topical applications are also used on the skin for radiation damage, the prevention of dermatitis and pain, as well as, an agent to decrease healing times on skin injuries. It was a popular treatment in the Civil War and World War I to reduce wound bleeding and infection. Its use in the compositions is for its anti-inflammatory and wound healing properties.

*Camellia* Oil—*Camellia japonica* has been used for centuries by the Japanese as skin care and moisturizing compositions, as well as, for wound healing and scar reduction as it readily absorbs into the skin. It has also been used medically as a vitamin carrier for injections. The oil is cold pressed from seeds. *Camellia* is part of the flowering plants from the Theaceae family with leaves from *Camellia sinensis* the most popular for tea products. Its primary use in the compositions is it anti-inflammatory and wound healing properties.

Capaiba Oil (CPO)—*Copaifera officinalis*—It reduces pain and inflammation, protects against infections, heals the skin, prevents fungal growth, and boosts the respiratory health. It improves the skin, speeds up healing, and tightens the skin. Copaiba essential oil is a distilled oil from an oleoresin. This resin is produced as a sap from a tree in the *Copaifera* genus. The oil is a pale yellow in color with a slightly bitter taste and an aroma. Copaiba is considered to be one of the most anti-inflammatory substances on earth. In traditional medicine, this essential oil has been used extensively by indigenous people. The active components in copaiba essential oil consist mainly of terpenes. It has topical applications and the copaiba essential oil has astringent properties. Copaiba's active components tighten the skin, which can help the skin look younger, reduce the appearance of wrinkles, and even strengthen the skin to prevent lesions or wounds as the body ages. Additionally, a topical application of copaiba essential oil helps reduce the appearance of acne on the face. Copaiba essential oil also heals the skin and infuses the body with powerful nutrients and organic compounds that can eliminate the appearance of blisters, marks, and pimples. Copaiba essential oil is often topically applied to scars in order to speed their healing and reduce their visibility. Copaiba essential oil is a analgesic and is a strong antibacterial agent. It can act as a shield for your skin, protecting any wounds from developing an infection. The unique terpene structures found in copaiba essential oil are very effective as antifungal agents.

Capryllic, Capric Triglyceride—Formulae—Capryllic Acid $C_8H_{16}O_2$, —Capric Acid CH3(CH2)sCOOH—*Cocos nucifera* is the cocoa nut palm from which the composition is purified as <10% constituents of the kernal. Individual uses of these triglycerides have little direct effect on the intended use of this topical composition. However, this mixed, medium chain triglyceride composition is considered an inert energy source readily available for use by the skin cells and dermis cells that are being challenged to function properly in their limited condition brought on by their specific disease state.

Carvacrol (CVC)—Formula—$C_6H_3(CH_3)(OH)C_3H_7$—It is a monoterpenoid phenol. It has a characteristic pungent, warm odor of oregano. Carvacrol inhibits the growth of several bacteria strains, e.g. *Escherichia coli*. It disrupts cell membranes of bacteria and inhibits their proliferation.

Carvone Oil (CRV)—Formula—$C_{10}H_{14}O$—It is a terpenoid and found naturally in many essential oils, but is most abundant in the oils from seeds of caraway (*Carum carvi*), spearmint (*Mentha spicata*), and dill. Carvone is available in both enantiomerically pure forms.

Caryophyllene Oil—This oil is most commonly from the stem and flowers of *Syzygium aromaticum* to produce clove oil. There are 14 plant sources of Caryophyllene oil. However, only 9 of these plants have their Caryophyllene levels above 10% of these oils from clove, cannabis, hops, basil, oregano, West African pepper, cinnamon, malabathrum, and ylang-ylang. Two of these, the West African pepper and the India cinnamon or malabathrum, contain up to 25% of their oils as Caryophyllene oil. Its use in the compositions is primarily for its anti-inflammatory properties.

Cedarwood essential Oil—An essential oil derived from various types of conifers, most in the pine or cypress botanical families. It has uses in medicine and perfumery, and while the characteristics of oils derived from various species may themselves vary, all have some degree of bactericidal effects. Although termed cedar or cedarwood oils, the most important oils are produced from distilling wood of a number of different junipers and cypresses (of the family Cupressaceae), rather than true cedars (of the family Pinaceae). Cedarwood oils each have characteristic woody odors which may change somewhat in the course of drying out. The crude oils are often yellowish or even darker in color. They find use in fragrance applications. The oil has antifungal and antibacterial properties.

Cetyl Alcohol (CTA)—Formula—$CH_3(CH_2)_{15}OH$—It is a fatty alcohol and also known as hexadecan-1-ol and palmityl alcohol. At room temperature, cetyl alcohol takes the form of a waxy white solid or flakes. Cetyl alcohol is used in the cosmetic industry as an opacifier in shampoos, or as an emollient, emulsifier or thickening agent in the manufacture of skin creams and lotions.

Chamomile German Oil—*Chamaemelum nobile* is used for treating skin conditions such as eczema, chicken pox lesions, and psoriasis. It has a wide medical usage for inflammation, ulcers, and hemorrhoids. Chamomile tea has long been popular and is made from the dried flowers and may be a relaxant. There also may be anti-anxiety effects from its use. Its primary use in the compositions is to aid healing and reduce inflammation.

Elemi Oil (EMO)—It is steam distilled from the resin of the Asian tree *Canarium luzonicum* or *Canarium vulgare*. Elemi Oil is rich in monoterpenes. It can be especially helpful in wound care and for supporting respiratory health. It has a clear color with a tinge of yellow. It is effective against infectious skin conditions, wounds, cuts, fatigue.

Geranium Essential Oil—*Pelargoniun graveolens* encompasses a relatively large group of plants from which this complex, essential oil comprises ~50 different oil components. The number of species has been greatly increased due to significant hybrid culturing seeking to focus on different flower and scent expressions. It currently has limited medicinal use and is being used as a general oil solution and fragrance for these applications.

Ghana Shea Butter—*Vitellaria paradoxa* is the general name for the Shea trees of the Sapotacea family and is the only species in this genus, located predominantly in Africa. This species is a major food source of dietary fat. Shea butter is composed of 5 fatty acids:palmitic, stearic, oleic, linoleic and arachidic of which 85-90% is stearic and oleic acids. These fatty acid contents change in percentages from region to region in Africa with the shea butter changing from liquid to near solid depending upon the fatty acid concentrations. There are also 10 phenolic compounds in shea butter that also vary from region to region. Therefore, shea butter is obtained from one region, Ghana. Shea butter is one of the largest components of the compositions and is used not only for composition consistency but also as a major anti-oxidant.

Glycerol—Formula—$C_3H_8O_3$—Glycerol is a colorless, odorous liquid with three —OH groups assuring solubility in water that is also hydroscopic. It is the backbone of all triglycerides. It is derived from soy beans and under large scale manufacturing. It is widely used for extractions of plant compositions and as a solvent. Its primary use in the compositions is as a solvent.

Ho Wood Oil (HWO)—*Cinnamomum camphora* var linaloo—It is steam distilled from the bark and wood. Ho Wood is one of the most potent sources of naturally occurring linalol found in any steam distilled essential oil. Aromatically, Ho Wood Essential Oil is a beautifully fragrant wood oil that possesses some similarity to that of Rosewood Oil. The color is clear. A sweet, fresh and woody, with subtle floral notes. Its significant content of linalol gives it analgesic, anti-inflammatory and antibacterial properties.

Jasmine Essential Oil—*Jasminum officinale* is a species of the olive family in Eastern Europe and Asia that has been adopted as a garden varietal with appealing flowers. It has a history of use in aromatherapy and herbal medicine predominantly as a skin anti-septic and anti-inflammatory agent. Its inclusion in the compositions is for these uses, as well as, its essential oil fragrance.

Kaempferol—Formula—3,4',5,7-tetrahydroxyflavone ($C_{15}H_{10}O_6$)—It is a natural flavonol. Kaempferol is a yellow crystalline solid. It is slightly soluble in water and highly soluble in hot ethanol, ethers, and DMSO. Kaempferol acts as an antioxidant by reducing oxidative stress. Kaempferol is common in Pteridophyta, Pinophyta and Angiospermae. Studies have shown kaempferol has pharmacological activities, including antioxidant, anti-inflammatory, antimicrobial, and analgesic activities. It also has been shown to work synergistically with antibiotics. Kaempferol has been shown to inhibit or decrease the activity of enzymes in viral infection, such as, reverse transcriptase, viral proteases and neuraminidase. Kaempferol has been shown to have an array of antioxidant effects. Kaempferol can prevent the oxidation of low-density lipid proteins.

Kanuka Oil (KNO)—*Kunzea ericoides* I *Leptospermum ericoides*—Sometimes known as White Tea Tree Essential Oil. Kanuka is much higher in monoterpenes than is Australian Tea Tree. It contains about 5% cineole. It is a pale yellow color.

Lavandin Oil (LVO)—The two most popular varieties are *Lavandula angustifolia* (lavender) and *Lavandula Intermedia* (lavandin). Lavandin is also commonly referred to as French lavender because it was developed for the French perfume industry. It is considered to be an antiseptic. Lavandin is a hybrid plant of true lavender and spike lavender. The oil is a pale yellow color to an almost neutral hue. The essential oil may assist in removing scars and stretch marks. It enhances blood circulation, promotes cell regeneration, and heals wounds and cuts. Lavandin oil has antiseptic properties that helps prevent infections from lacerations. It also speeds up the healing of cuts. It relieves pain and inflammation. The essential oil may alleviate pain in the muscles and joints. Lavandin oil is extracted by steam distilling the plant stalks and flowers. Lavandin may also be steam distilled with the help of a volatile solvent like benzene.

Limonene Oil (LMN)—Formula—$C_{10}H_{16}$—It is a colorless liquid aliphatic hydrocarbon classified as a cyclic monoterpene, and is the major component in the oil of citrus fruit peels. The D-isomer; occurring more commonly in nature as the fragrance of oranges, is a flavoring agent in food manufacturing. Limonene takes its name from the peel of the lemon. Limonene is a chiral molecule, and biological sources produce one enantiomer. Limonene is a relatively stable monoterpene and can be distilled without decomposition. It is a fragrance ingredient for cosmetics compositions.

*Litsea Cubeba* Oil (LCO)—*Litsea cubeba* is an evergreen tree or shrub in the Lauraceae family. It produces a fruit which is processed for its lemony essential oil. The oil is used as a fragrance and flavoring. It is used as a raw material by the chemical industry for the synthesis of vitamin A and violet-like fragrances.

Marula Oil—*Sclerocarya birrea* produces a nut from which this oil is recovered. Manila Oil contains a large proportion of mono-unsaturated fatty acids, as well as, significant anti-oxidants. Its primary anti-oxidant effects are due to tocopherols, sterols, and flavonoids. The primary use in the compositions is its wide types of fatty acids, as well as, its anti-oxidants.

Myrrh—It is a natural gum or resin extracted from a number of small, thorny tree species of the genus *Commiphora*. Myrrh resin is used as a perfume, incense, medicine, antiseptic and salves for abrasions and other minor skin ailments.

Nerolina Oil (NRL)—*Melaleuca quinquenervia*—It is a sweetly-scented oil distilled from the leaves and small branches of the paperbark tea tree or the broad-leaved paperbark tree. Nerolina oil is a component of perfume and has topical antibacterial properties. Nerolina oil is a rich emollient and easily penetrates the skin's surface. It can be added to coconut oil, cocoa butter, shea butter or other natural moisturizers to accentuate their effects to soften skin. Nerolina oil aids in the composition of vitamin E and the skin proteins collagen and elastin, which make up the skin's structural layer and accelerates cell turnover.

Niaouli Oil—It is also extracted from *Melaleuca quinquenervia*. Niaouli Oil has camphorous, earthy and a harsh smell. It has therapeutic benefits helpful for skin infections, acne, rashes, pimples, wounds and cuts.

Palmarosa Essential Oil—*Cymbopogon martinii*—It is a species of lemon grass with a popular fragrance. It contains geroniol and is used in medicinal applications. It is an effective anti-fungal agent, and used predominantly in food storage. Its primary use in the compositions is its fragrance but also as an anti-fungal and potential non-specific medicinal actions.

Palo Santo—Also called Lignum vitae, guayacan or guaiacum. The wood is obtained chiefly from *Guaiacum officinale* and *Guaiacum sanctum*, both small, slow growing trees. "Lignum vitae" is Latin for "wood of life," and derives its name from its medicinal uses. Lignum vitae resin is used to treat a variety of medical conditions from coughs to arthritis.

Panthenol (PNT)—Formula—HO—$CH_2$—C($CH_3$h-CH(OH)—CONH—$CH_2CH_2CH_2$—OH— The alcohol analog of pantothenic acid (vitamin $B_5$) and a provitamin of $B_5$. It is commonly utilized in pharmaceuticals, cosmetics, and skin care products as a moisturizer and humectant. It readily penetrates the skin and mucous membranes where it is converted to pantothenic acid that readily binds water and enables reactivity with other composition components and with the tissues. It is odorless, colorless and a viscous liquid at room temperature. Panthenol is to improve wound healing in pharmaceutical and cosmetic compositions. In ointments it is used for the treatment of sunburns, mild burns, and minor skin injuries. It improves hydration, reduces itching and inflammation of the skin, improves skin elasticity, and accelerates epidermal wounds' rate of healing. Pantothenic acid is extremely hygroscopic. It is used in the biosynthesis of coenzyme A. Panthenol is an odorless, slightly bitter, highly viscous, transparent and colorless liquid at room temperature. It is easily soluble in water. Panthenol comes in two enantiomers, D and L. Only D-panthenol (dexpanthenol) is biologically active, however both forms have moisturizing properties.

Peppermint—*Mentha x piperita*—An herbal extract using alcohol of essential oils of peppermint leaves. Medicinal uses of peppermint extract may relieve itching when applied topically. Moreover, peppermint extract is believed to have antiviral and medicinal properties.

Rose Hip Oil—*Rosa moschata, R. rubiginosa* and *R. canina*—Wild rose species that produce seeds are extracted for Rose Hip Oil. It contains Provitamin A with high levels of tretinoin that is an all-trans retinoic acid that can be converted to Vitamin A. Rose Hip Oil contains the essential fatty acids of linoleic acid (omega 6) and linoleic acid (omega 3). Rose Hip Oil is frequently used in a variety of skin conditions including eczema, dermatitis, and sunburn, as well as, photoaging and healing scars. Its inclusion in these formulations is primarily for its anti-inflammatory effects.

Rosemary Oil (RMO)—*Rosmarinus officinalis*—It is a woody, perennial herb with fragrant flowers and is a member of the mint family Lamiaceae. Rosemary leaves are used as a flavoring in foods. Rosemary oil is used for fragrant bodily perfumes and an aroma into a room.

Sacha Inchi Oil—*Plukenetia volubillis*—It is a small tree that produces star shaped fruits with enclosed nuts. The nuts contain high protein (27%) and oil (35-60%). The oil is rich in essential fatty acids. There is not much evidence for its use in skin care compositions but its components suggest it should be helpful in skin care compositions. Its primary use in the compositions is supportive of the other oils with already demonstrated effectiveness.

Sea Buckthorn Oil—*Hippophae rhamnoides*—It accumulates lipids in the fleshy, pulp part of the fruit, as well as, in their seeds. The pulp oil is preferred for these applications since it has high concentrations of the mono-unsaturated fatty acid, palmitoleic acid, and the saturated fatty acid, palmitic acid, which are at unusual levels compared to the plant kingdom. Caretenoids provide the color in the oil and provide beta-carotene, zeazanthin, and lycopene that are associated with Vitamin A activity. The tocopherols and tocotrienols components are major reasons for the anti-oxidant activity of this oil. Its primary purpose for the compositions is its anti-oxidant activities.

Tamanu Oil—*Calophyllum inophyllum*—It is a large evergreen that produces nuts that contain 70-75% oil. This oil contains Linoleic acid (38%), Oleic acid (34%), Stearic acid (13%), and Palmitic acid (12%). Additional oil components include calophyllolide, freidlin, inophyllums B & P, terpenic essences, benzoic acid, oxibenzoic acid, phosphoamino lipids, glycerides, saturated fatty acids, and 4-phenylcoumarins. This oil has been used for skin diseases and for treating ulcers and infected wounds. Its inclusion in the compositions is for its anti-inflammatory and wound healing characteristics.

Terpineol—Formula—$C_{10}H_{18}O$— It is a monoterpene alcohol that has been isolated from a variety of sources such as cajuput oil, pine oil, and petitgrain oil. There are four isomers, alpha-, beta-, gamma-terpineol, and terpinen-4-ol. Beta- and gamma-terpineol differ only by the location of the double bond. Terpineol is usually a mixture of these isomers with alpha-terpineol as the major constituent. Terpineol has a pleasant odor similar to lilac.

Thyme Red. White—An aromatic perennial evergreen herb with culinary, medicinal, and ornamental uses. The most common variety is *Thymus vulgaris*. Thyme is of the genus Thymus of the mint family (Lamiaceae). Thymol, an antiseptic, is an active ingredient in various commercially produced mouthwashes. Oil of thyme was used to medicate bandages before the advent of modern antibiotics.

Vetiver—*Chrysopogon zizanioides*—It is a perennial bunchgrass of the Poaceae family. Vetiver has been used to produce perfumes, creams and soaps. It is used for its antiseptic properties to treat acne and sores. Vetiver is mainly cultivated for the fragrant essential oil distilled from its roots. Vetiver is a more common ingredient in fragrances for men.

Vitamin E—Formula (a-tocopherol)—$C_{29}H_{50}O_2$—Vitamin E has several different configurations, but the most prominent is a-tocopherol. Vitamin E is a lipid soluble vitamin from wheat germ oil, sunflower oil, and safflower oil. It stops the propagation of oxygen radicals through cell membranes and protects cells from oxygen radical damage. It is used in a number of medical supplements and topical medication, but it may not be effective in wound healing or reduction of scar tissue. Its use in the compositions is to provide assistance in proper healing of wounds and its anti-oxidant properties.

Winter Savory—*Satureja montana*—It is a perennial, semi-evergreen herb in the family Lamiaceae. Winter savory has antiseptic and aromatic benefits. It has been used in the treatment of bee stings or insect bites. Therapeutic-grade oil inhibits growth of yeast.

Hydrophilic Components

1-Tetradecanol—Formula—C14H300—Myristyl alcohol (*Myristicafragrans*—nutmeg plant) is a straight-chain saturated fatty alcohol. 1-Tetradecanol is prepared by the hydrogenation of myristic acid (or its esters). Myristic acid is found in nutmeg. 1-Tetradecanol is used as an ingredient in cosmetics, such as, cold creams for its emollient properties.

Agave Nectar—*Agave tequilana* weber azul—Besides producing tequila, it produces agave nectar that is high in fructose (47%) and glucose (16%) concentrations. It is included in the compositions as a readily available fuel source for the cells being treated.

Alanine—Formula—$C_3H_7NO_2$—Alanine is a non-essential amino acid since the body readily produces it. One main dietary source is in meats. Alanine is an important amino acid in collagen and other similar proteins. Its use in the compositions is to enhance the ability to produce collagen.

Aloe Vera Gel—*Aloe barbadensis* mil—It is a short growing plant. Studies have not confirmed its use for treating burns, wounds, and sunburn. Topical aloe vera is not associated with toxicity issues or side effects. Historically, aloe vera was used topically and continues use in traditional medicine today. Its role in the composition relates to a potential role in healing cutaneous damages due to different causes and to increase the rate of healing.

Arginine (ARG)—Formula—$C_6H_{14}N_4O_2$—An a-amino acid that is used in the biosynthesis of proteins. In humans, arginine is classified as a semiessential or conditionally essential amino acid, depending on the developmental stage and health status of the individual.

Artie Fish Collagen—*Arctogadus glacialis*—The artic cod lives in the artic seas at cold temperatures and is thus one of the few species whose collagen is a liquid at cold and room temperatures. Collagen from non-artic animals and non-artic fish is a solid at room temperature. For the compositions, dissolvable collagen is a major advantage in utilizing the protein in the compositions that is in a liquid form rather than a solid form so it can readily react with the other components. Its use in the compositions is to provide collagen forwound support and softening.

Benzocaine—Formula—$C_9H_{11}NO_2$—Benzocaine is a local or topical anesthetic to relieve topical pain. It appears in many compositions to treat a variety of pain related problems. Local anesthesia for oral and pharyngeal mucous membranes is common for sore throats, mouth ulcers, denture irritation, earache, insect bites, and similar topical irritations. Few side effects are noted as long as intended doses are utilized. Its addition in the compositions is only applicable to the two types of oral mucosa! lesions described and should not be given to young children.

Distilled water—Formula—$H_2O$—It is water that has been boiled into vapor and condensed back into liquid in a separate container. Impurities in the original water that do not boil below or at the boiling point of water remain in the original container. Distilled water can also refer to reverse osmosis and ultrafiltration of tap water. Thus, distilled water is purified water.

Ferulic Acid—Formula—$C_{10}H_{10}O_4$—Ferulic acid is a hydroxycinnamic acid and a natural phenol that is a major anti-oxidant that readily reacts with free radicals that accelerate aging of the skin. Its use in the compositions to reduce free-radical damage at the time of attempting to stimulate new cell growth and metabolism during the use of the compositions.

Glutamine (GLU)—Formula—$C_5H_{10}N_2O_3$—An a-amino acid that is used in the biosynthesis of proteins. Its side chain is similar to that of glutamic acid, except the carboxylic acid group is replaced by an amide.

Glycine—Formula—$C_2H_5NO_2$—Glycine is the simplest possible formula for an amino acid and remains in dissolved in both hydrophobic or hydrophilic solutions. Its use in the compositions is to enhance the ability to form collagen.

Histidine (HST)—Formula—$C_6H_9N_3O_2$—An a-amino acid and is a positively charged amino acid at physiological pH. The histidine amino acid is a precursor for histamine, an amine produced in the body necessary for inflammation.

Hydroxyproline (HDP)—Formula—$C_5H_9NO_3$—A common non-proteinogenic amino acid. Hydroxyproline is a major component of the protein collagen, comprising roughly 13.5% of mammalian collagen. Hydroxyproline and praline play key roles for collagen stability. They permit the sharp twisting of the collagen helix. Hydroxyproline is found in few proteins other than collagen.

Isoleucine (ISL)—Formula—$C_6H_{13}NO_2$—An a-amino acid and must be ingested in the diet since it is essential in humans.

Lecithin—Lecithin is a generic term including animal and plant materials that are both hydrophilic and lipophilic mixtures of glycerophospholipids, that include phosphatidylcholine, phosphatidylethanolamine, phosphatidylinositol, and phosphoric acid. It can be processed from soybeans, eggs, milk, marine sources, rapeseed, cottonseed, and sunflower. While it has low solubility in water, it is an excellent emulsifier. Its use in the compositions is to function as an emulsifier and dispersing agent for the combination of hydrophilic and hydrophobic components.

Leucine (LUC)—Formula—$C_6H_{13}NO_2$—An essential amino acid. Leucine exhibits pharmacological activity in humans and have been demonstrated to promote protein biosynthesis. Leucine is a dietary amino acid with the capacity to directly stimulate myofibrillar muscle protein synthesis.

Linoleic Acid (LOA)—Formula—$C_{18}H_{32}O_2$—A polyunsaturated omega-6 fatty acid, an 18-carbon chain with two double bonds in cis-configuration. It typically occurs in nature as a triglyceride ester. Free fatty acids are typically low in foods. Linoleic acid belongs to one of the two essential fatty acids.

Lysine (LYS)—Formula—$C_6H_{14}N_2O_2$—An a-amino acid and is essential in humans. Lysine plays a role in crosslinking of collagen polypeptides, uptake of essential mineral nutrients, and in the production of carnitine. Due to its importance in several biological processes, a lack of lysine can lead to several disease states including defective connective tissues, impaired fatty acid metabolism, anemia, and systemic protein-energy deficiency.

Methyl Sulfonyl Methane—Formula—$C_2H_6O_2S$—Methyl Sulfonyl Methane (MSM) has one additional oxygen compared to the similar Dimethyl Sulfoxide (DMSO). It is found naturally in a number of primitive plants and in the atmosphere above marine areas. It has been tested in a number of medical conditions similar to DMSO, but does not have any medical disease approval by the FDA. It is sold as a dietary supplement without any substantiated claims. For cutaneous application, its primary role may simply be enhancement of compositions through the skin rather than a primary effect by itself. Although, it may have anti-inflammatory effects as does DMSO. The FDA has approved MSM for the Generally Regarded as Safe (GRAS) status. A number of animal studies suggest MSM benefits in oxidative stress and inflammation, but not sufficient for drug approval. MSM primary use in the compositions is to enhance cutaneous transfer of agents through the skin. It may also add relief as an anti-oxidant and an anti-inflammatory.

Niacinamide—Formula—$C_6H_6N_2O$—Niacinamide or nicotinamide are like niacin, critical vitamins to a number of important functions, including the NAD/NADP complex. NAD is critical to catabolism of fat, carbohydrate, protein, and alcohol and cell signaling and DNA repair. NADP is important for anabolic reactions in fatty acid and cholesterol synthesis. Its use in the compositions along with niacin is to provide these required compounds that are important in these types of reactions.

Oleic Acid (OLA)—Formula—$CH_3(CH_2)?CH=CH(CH_2)?COOH$—A fatty acid that occurs naturally in various animal and vegetable fats and oils. It is an odorless, colorless oil. In chemical terms, oleic acid is classified as a monounsaturated omega-9 fatty acid. It is the most common fatty acid in nature.

Proline—Formula—$C_5H_9NO_2$—Praline is a non-essential amino acid that the body can produce. Praline is biosynthetically derived from the amino acid L-glutamate. However, its commercial synthesis is from diethyl maionate and acrylonitrile. It is used in the compositions to enhance the production of collagen.

Protocatechuic Acid (PCT)—Formula—$C_7H_6O_4$—A dihydroxybenzoic acid which is a type of phenolic acid. Protocatechuic acid is antioxidant and anti-inflammatory.

Sericin—Formula—C30H40N10O16—It is a protein created by *Bombyx mori* (silkworms) in the production of silk. Silk consists of 70-80% fibroin and 20-30% sericin. Fibroin is the structural center of the silk and sericin being the gum coating the fibers and allowing them to stick to each other. Composed structurally of 18 different amino acids, and 32% serine in a randomized amorphous coil. Sericin can be easily converted into a-sheet conformation, via repeated moisture absorption and mechanical stretching. Sericin has been used in medicine and cosmetics. Sericin is primarily used in medicine for wound suturing due to its elasticity, tensile strength, and a natural affinity for keratin. It has a natural infection resistance and biocompatibility, and can be used as a wound coagulant. When used in cosmetics, sericin has been found to improve skin elasticity and several anti-aging factors which include an anti-wrinkle property. This is done by minimizing water loss from the skin.

Sodium Polyacrylate—Formula—$[-CH_2-CH(CO_2Na)-]n$—It is a sodium salt of polyacrylic acid is an anionic polyelectrolyte with negatively charged carboxylic groups in the main chain and has a broad application in consumer compositions. This super absorbent polymer has the ability to absorb as much as 100 to 1000 times its mass in water.

Vitamin A (VTA)—A group of unsaturated nutritional organic compounds that includes retinal, retinal, retinoic acid, and several provitamin A carotenoids (most notably beta-carotene). Vitamin A has multiple functions. It is important for growth and development, maintenance of the immune system and good vision. Vitamin A is needed by the retina of the eye in the form of retinal. Vitamin A also functions in a very different role as retinoic acid (an irreversibly oxidized form of retinal), which is an important hormone-like growth factor for epithelial and other cells.

Vitamin B3 (VTB3) or Niacin—Formula—$C_6H_5NO_2$—Niacin cannot be directly converted to niacinamide, but both are critical precursors of the important NAD/NADP complex. NAD is critical to catabolism of fat, carbohydrate, protein, alcohol, cell signaling and DNA repair. NADP is important for anabolic reactions in fatty acid and cholesterol synthesis. Niacin also is a vasodilator that can also aid in the absorption of the composition on the skin. Their uses in the compositions along with niacinamide are to provide these required compounds that are important in these reactions.

Vitamin C—Formula—$C_6H_8O_6$—Vitamin C or Ascorbic Acid is water soluble and found in dairy and food supplies. Vitamin C is an essential nutrient that is required for tissue repair and a cofactor in multiple enzymatic reactions. Vitamin C is critical for collagen production, carnitine production, and neurotransmitter production. It functions importantly in the body as an anti-oxidant protecting against oxidative stress. It is used in the compositions as an anti-oxidant, for tissue repair, and collagen production. An alternative to Vitamin C is D-iso-ascorbic acid that blocks collagen formation, opposite to Vitamin C. It is only used in the one composition as a topical use in cutaneous Scleroderma to attempt to limit the excessive collagen production that causes skin thickening and joint movement limitations. It is the excessive collagen formation in the subcutaneous site that builds up as a response in Scleroderma that is stimulated by its inflammation and the responses to that inflammation.

Additional Beneficial Components of Compositions

Emu Oil—*Dromaius novaehollandiae* is the emu that is indigenous to Australia. The oil is extracted from adipose tissue with this industry refined product containing 70% unsaturated fatty acids. Oleic acid, a mono-unsaturated omega-9-fatty acid, is the largest component. It also contains 20% linoleic acid, an omega-6-fatty acid and 2% linoleic acid, an omega-3-fatty acid. Its claims as a dietary supplement have not been confirmed. However, recent clinical studies suggest efficacy in its use as a skin moisturizer and as an insect repellent. Its proposed use in the product is as a skin moisturizer.

Emu Oil Solids—*Dromaius novaehollandiae* is the emu that is indigenous to Australia. After the oil is extracted from processed adipose tissue, there is a residual oil based, semi-solid product that can be used as a thickener for skin care products. It is used in the product as a thickener replacement for bees wax.

*Helichrysum Italicum* Essential Oil—*Helichrysum Italicum* is one of 600 species of Helichrysum with its oil designated as an essential oil. It is part of the sunflower family occurring in South Africa, Madagascar, Australasia, and Euroasia. Its primary use in the formulation is as a standard fragrance.

Hyssop Oil—*Hyssopus officinalis* is from southern Europe and the Middle East commonly used as a medicinal plant, predominantly as an antiseptic, expectorant, and cough depressant that can also stimulate the gastrointestinal system. Its use in the product is as an oil with an antiseptic nature. It is limited to products for use only in adults as it can cause seizures in young children.

Lavender Essential Oil—*Lavendula augustiflora* is a species of lavender from which the oil is produced that is a complex mixture of natural phytochemicals with the major components being linalool and linalyl acetae and the major supply produced in Bulgaria. It has a long usage in perfumes and aromatherapy. Its primary contribution to the product is fragrance.

Patchouli Essential Oil—*Pogostemon patchouli* or *P. cabin* are shrub-like plants originally in tropical regions of Asia, but are now cultivated widely in tropical areas due to the popular nature of this fragrance. This essential oil is prepared by steam distillation of the leaves. Three primary components of this oil are Patchoulol—Formula—$C_1sH_260$—that is the primary essence of the scent of the product, Norpatchoulenol—Formula—$C14H220$—that is a terpenoid component that also effects the primary scent, and Germacrene—$C_{15}H_{24}$—that has anti-microbial properties. This essential oil has been used in perfumes for centuries and is now found in insect repellents and alternative medicines. Its use in the product is primary for fragrance but also for its anti-microbial component.

Ylang-Ylang Essential Oil—*Cananga odorata*, known as the tropical *cananga* tree in Indonesia, Malaysia, and the Philippines, is valued for its Ylang-Ylang flowers that produce a popular oil through steam distillation that has been used for centuries in perfume. Its primary components are Linalool, Germacrene, Caryophyllene, p-cresyl methyl ether, methyl benzoate, and sesquiterpenes. Its proposed medicinal usages include reduction of blood pressure, reduction of sebum secretion in the skin, and as an aphrodisiac. Its primary use in the product is as a fragrance, although it contains several components that are in other valuable oil products from this region that we use.

Berberine HCL—Formula—$C_{20}H_{18}NO_4$—*Berberis vulgaris* is one of several plants with berberine as a quarternary ammonium salt with a very strong yellow color used for dying wool and other fabrics. It was reported in use in China as a folk medicine in 3,000 BC. It currently is a research product for different potential treatments of arrhythmia, diabetes, hyperlipidemia, and cancer. Berberine is considered an antibiotic and is being evaluated as a treatment for methicillin-resistant Staph infections. It is used in the product as a potential anti-microbial as well as a marker for the lack of anti-oxidant activity that would reduce the yellow color.

Chlorhexidine—Formula—$C_{22}H_{30}ChN_{10}$—Chlorhexidine is used in disinfectants, cosmetics, and pharmaceutical products as an anti-microbial agent that appears more potent than provodone-iodine (Betadine). It is active against Gram-positive and Gram-negative organisms, facultative anaerobes, aerobes, and yeasts. It is particularly effective against Gram-positive bacteria (2:1 µg/l). Significantly higher concentrations (10 to 73 µg/ml) are required for Gram-negative bacteria and fungi. At physiologic pH, it disassociates and releases the positively charged chlorhexadine cation that readily binds to the negatively charged bacterial cell wall. At low doses, its membrane binding acts as bacterial static effect. At high doses, its binding to the bacterial cell wall causes cell wall disruption and destruction of the microbe. It is on the World Health Organization's List of Essential Medicines. It is used in the product for its potent anti-microbial activities.

Natamax—Formula—C33H$_7$NO13—Natamycin (Natamax) is a naturally occurring anti-fungal agent produced during fermentation by *Streptomyces natalensis* that is commonly found in soil. It is used in the food industry as a natural preservative. It is listed on the World Health Organization's List of Essential Medicines. It has been used in the food industry for decades in dairy products and other foods to retard microbial growth. Its medical use is usually in the form of a cream, lozenge, or drops for the eye or ear. It does not have any acute toxicity in animals or humans. It inhibits fungal growth by inhibiting amino acids and glucose passage across plasma membranes. It is used in the product to inhibit fungal growth.

Panthenol—Formula—$C_9H_{19}NO_4$—Panthenol is an alcohol analogue of Vitamin B5 or pantothenic acid that is commonly utilized in pharmaceuticals, cosmetics, and skin care products as a moisturizer and humectant. It readily penetrates the skin and mucous membranes where it is converted to pantothenic acid that readily binds water and enables reactivity with the other product components and with the tissues. It is odorless and colorless. Its inclusion in the product is for its moisturizing and humectant qualities.

Ouercitin—Formula—$C_{15}H_{10}O_7$—Quercitin is a plant polyphenol in the flavonoid group that is widely found in many vegetables and in many supplements. It is a form of many flavonoid glycosides. In spite of many studies, there is no clear evidence that the use of quercitin is useful in the treatment of cancer or any other diseases. This may in part be due to the fact that quercitin has a very short half-life in the human body. The question for the product is if its half-life can be longer in these topical to subcutaneous products. Its in vitro pharmacology supports the anti-oxidant activities of this compound. Its use in the product is to be an anti-oxidant in the skin and subcutaneous sites.

Ubiquitin—Formula—$C_{89}H_{151}N_{27}O_{24}$—Ubiquitin is a small, regulatory protein that exists in all eukaryotic cells, those with a nucleus and membrane bound organelles. It has 4 genes in the human genome that code for it. Ubiquitin carries out a multitude of functions predominantly through protein conjugations that result in many different protein modifications, from induced degradation, to change cellular location, to alter their activities, and to either promote or inhibit protein interactions. They can also form chains together to add another dimension to their protein interactions. Ubiquitin is highly conserved with human cells and yeast sharing 96% sequence identity. Abnormal ubiquitin activity is associated with many different diseases that can have tissue sections staining for excessive accumulations of ubiquitin based compounds including Alzheimer's (neurofibrillary tangles), Parkinson's (Lewy body), Huntington's (inclusions in motor neurons), alcoholic liver disease (Mallory bodies), and brain astrocytes (Rosenthal fibers). A number of studies have related that defects and alterations in ubiquination processes are often found in a variety of cancers, including renal cell, breast, cervical, colorectal, and glioblastoma. Ubiquitin is utilized in the product to potentially promote normal cell replication and growth, both intimately involved with the product.

Vanzan—Formula—$C_{13}H_{10}O$—Zanthan gum, a polysaccharide, that was discovered as a product of fermentation from a strain of bacteria, *Xanthomohas campestris*, that can be commercially produced using these bacteria given simple sugars and the proper fermentation conditions. It has many uses regarding its ability to readily increase viscosity in a variety of liquids, including in foods and drinks. It is used in the product to increase thickening as required above that achieved by phase change and other agents.

Groups of Components
Core
a-Pinene (APN)
Glycerol (GLY)
Ghana Shea Butter (GSB)
Black Cumin Seed Oil (BCS)
AF (Artie Fish) Collagen(AFC)
Aloe Vera Leaf Gel (AVLG)
Lecithin (LCT)
Methyl Sulfonyl Methane (MSM)
Functional Oil
Apricot Kemal Oil (AKO)
Argan Nut Oil (AGN)
Baobab Oil (BAB)
Calendula Oil (CDA)
Camellia Oil (CMA)
Caprylic, Capric Triglyceride (CCT)
Caryophyllene (CAP)
Elemi Oil (EMO)
Kanuka Oil (KNO)
*Litsea Cubeba* Oil (LCO)
Manila Oil (MRL)
Palmarosa Oil (PLO)
Palo Santo
Rose Hip Seed oil
Sachi Inchi oil
Sea Buckthom Oil (SBO)
Tamanu Oil (TMU)
Alcohol
Benzyl Alcohol (BA)
Cetyl Alcohol (CTA)
Panthenol (PNT)
Anti-Inflammatory
Acai Berry
Chamomile German Oil (CGB)
Capaiba Oil (CPO)
Myrrh
Rose Hip Seed Oil
Oleic Acid (OLA)
Linoleic Acid (LOA)
Anti-Oxidant
Kaempferol
Caffeic acid
Protocatechuic Acid (PCT)
Anti-Microbial
Anethole Anise Camphor
Cabreuva Oil
Carvacrol (CVC)
Niaouli Oil
Thyme Red, White
Winter Savory
Floral
Rosemary Oil (RMO)
Thickener
Benzoin (BZN)
Wax
Bees Wax (BW)
Flavors
Cedarwood essential Oil
Fragrance
Carvone Oil (CRV)
Geranium Oil (GER)
Ho Wood Oil (HWO)
Jasmine Oil (JAS)
Lavandin Oil (LVO)
Limonene Oil (LMN)
Nerolina Oil (NRL)
Peppermint
Terpineol
Vetiver
Fatty Acid
Ferulic Acid (FRA)
Analgesic
Benzocaine
Amino Acid
Alanine (ALA)
Arginine (ARG)
Glutamine (GLU)
Glycine (GLY)
Histidine (HST)
Hydroxyproline (HDP)
Isoleucine (ISL)
Leucine (LUC)
Lysine (LYS)
Praline (PRL)
Carbohydrate
Agave nectar (AGV)
Vitamin
Vitamin A (VTA)
Vitamin B3 (VTB3) or Niacin
Vitamin C (VTC)
Vitamin E (VTE)
Niacinamide (NCM)
Solvent
Distilled water
Gel
Sericin
Moisturizer
Sodium Polyacrylate
1-Tetradecanol

EXAMPLES

Dupytren's Disease and Contracture

Example 1

Dupytren's Disease of the hands is an early form of what most likely will evolve overtime into Dupytren's Contracture of the hands. This relatively infrequent disease is based on northern European ancestry that increases in incidence typically from age 45-50 years of age with increasing incidence and severity of existing disease throughout the rest of these people's lives. There is a mild increase in the incidence of males over females in the progression of the disease. The earlier in life it begins the expectation of more accelerated progression and the involvement of more fingers will be experienced. It converts from Dupytren's Disease to Dupytren's Contracture when the fingers begin to bend in towards the palms. The abnormality begins as the Disease with the discovery of a subcutaneous nodule on the palmar surface of the hand that is usually not tender at the base of fingers 3, 4, and 5 on either hand. After a relatively short time, abnormal skin folds begin to develop below the nodule into the palm. Additional nodules may form then or at any time in the future on either hand mostly involving fingers 3, 4, and 5. Another example of involvement of any finger is observed by placing the palm on a flat surface and determining the ability to raise the affected finger up off the table. Over time, the involved fingers will not be able to rise above the flat surface. Progression of this problem is expected for any involved finger in Dupytren's Disease to Dupytren's contracture whenever the angle between any finger and the palm begins to decrease from vertical with the hands held upright. Ongoing disease progression of Dupytren's Contracture will be noted with further movement of the fingers into the palm, as shown in FIG. 1. This degree of curvature is measured to document ongoing progression of the disease.

The disclosed composition halts the progression of Dupytren's disease to the Dupytren's contracture stage. All nodules show significant decrease in size which appears to happen within the first 2-4 months of treatment.

Example 2

White male, 69 years old, developed palm nodules and skin folds at base of both left and right hands with rigid third digits in 2014. When the left hand had progressed to bend towards the palm at 5 degrees in 2015, the first preliminary product formulation used twice daily, thoroughly rubbing it into the skin, made nodules disappear and stopped progression of contracture of third digit. The composition was applied to both fingers twice a day. Within a few weeks of using the composition, the nodule size and thickness began to decrease, first on the left hand and then followed on the right hand. More importantly, the left fourth finger had returned back to vertical, reversing from the early Contracture Stage back to the Disease Stage of Dupuytren's. Many months usage of the product kept these progressions limited. However, when no product was available for 6 months in 2017, ventral surface cords developed with new chords extending into the palm on both the left and right hands extending from the fourth fingers down into the palm. When product became available again, the previous progression of these lesions halted with continuous usage of this product twice a day up to November, 2018. Current observations show decreased skin folds, softening of the flexor chords, and no new contractures noted with continued twice a day usage.

Example 3

White male, 66 years of age developed skin nodules and skin folds on left and right third digits at the base. Both nodules disappeared and skin folds decreased with 6 months of twice a day applications.

Example 4

A small clinical trial for the use of the disclosed composition for patients with active Dupuytren's Disease and Contracture was conducted in Ukraine with two patients.

The first is a 73 year old male, 5 foot 6 inches weighing 139 pounds who had untreated contractures on the right hand for 11 years and on the left hand for 16 years. Prior to treatment, the right hand had a fifth finger Stage 3 contracture with 100° of flexion and a left hand fifth finger Stage 4 contracture with 150° of flexion. After 6 weeks of treatment with the disclosed composition, the right hand fifth finger contraction reduced to a Stage 2 contracture with 55° of flexion, but the left hand Stage 4 contraction treated for the same time remained a stage 4 lesion that only reduced to a 140° of flexion.

The second patient in this preliminary trial was also a 73 year old male, 5 foot 8 inches weighing 194 pounds who had untreated contractures on the right fifth digit Stage I with 25° of flexion and a fourth digit Stage 2 with 75° of flexion for 13 years. The left hand had a fifth digit Stage 3 contraction with 95° of flexion and a fourth finger Stage 4 contraction with 140° contraction for 9 years. After 6 weeks of treatment with the disclosed composition, the right hand Pith digit Stage 1 lesion with 25° of flexion remained a Stage 1 but no longer had any degrees of flexion. The right hand fourth digit Stage 2 contracture with 75° flexion reduced to 55° of flexion. The left hand fifth digit Stage 3 contracture with 95° of flexion reduced to a Stage 2 contraction with 45° of flexion. The left hand fourth finger Stage 4 contraction with 140° of flexion reduced to a Stage 3 contracture with 110° of contraction.

Table 5 lists the composition formulation for treatment of Dupuytren's Disease and Contracture.

TABLE 5

Dupuytren's Disease and Contracture Composition Formulation

| Hydrophobic Components | amount | Hydrophilic Components | amount |
| --- | --- | --- | --- |
| a-Pinene (APN) | 60 ml | 1-Tetradecanol | 2.5 g |
| Apricot Kernal Oil (AKO) | 5 ml | AF (Artie Fish) Collagen (AFC) | 40 g |
| Argan Nut Oil (AGN) | 5 ml | *Agave* nectar (AGV) | 10 ml |
| Baobab Oil (BAB) | 2.5 ml | Alanine (ALA) | 5 g |
| Bees Wax (BW) | 40 g | *Aloe Vera* Leaf Gel (AVLG) | 275 g |

TABLE 5-continued

Dupuytren's Disease and Contracture Composition Formulation

| Hydrophobic Components | amount | Hydrophilic Components | amount |
|---|---|---|---|
| Benzoin (BZN) | 4 ml | Arginine (ARG) | 5 g |
| Benzyl Alcohol (BA) | 50 ml | Distilled water | 500 ml |
| *Calendula* Oil (CDA) | 5 ml | Ferulic Acid (FRA) | 10 g |
| *Camellia* Oil (CMA) | 10 ml | Glutamine (GLU) | 5 g |
| Capaiba Oil (CPO) | 10 ml | Glycine (GLY) | 5 g |
| Caprylic, Capric Triglyceride (CCT) | 10 ml | Histidine (HST) | 5 g |
| Carvacrol (CVC) | 5 ml | Hydroxyproline (HDP) | 5 g |
| Caryophyllene (CAP) | 10 ml | Isoleucine (ISL) | 5 g |
| Cetyl Alcohol (CTA) | 40 g | Lecithin (LCT) | 25 g |
| Chamomile German Oil (CGB) | 10 ml | Leucine (LUC) | 5 g |
| Elemi Oil (EMO) | 5 ml | Linoleic Acid (LOA) | 5 ml |
| Geranium Oil (GER) | 2.5 ml | Lysine (LYS) | 5 g |
| Ghana Shea Butter (GSB) | 275 g | Methyl Sulfonyl Methane (MSM) | 25 g |
| Glycerol (GLY) | 10 ml | Niacinamide (NCM) | 2.5 g |
| Ho Wood Oil (HWO) | 2.5 ml | Oleic Acid (OLA) | 5 ml |
| Jasmine Oil (JAS) | 2.5 ml | Praline (PRL) | 5 g |
| Kanuka Oil (KNO) | 2.5 ml | Protocatechuic Acid (PCT) | 10 g |
| Lavandin Oil (LVO) | 10 ml | Sericin | 50 g |
| Limonene Oil (LMN) | 40 ml | Sodium Polyacrylate | 20 g |
| *Litsea Cubeba* Oil (LCO) | 5 ml | Vitamin A (VTA) | 2.5 g |
| Marula Oil (MRL) | 2.5 ml | Vitamin B3 (VTB3) or Niacin | 12.5 g |
| Nerolina Oil (NRL) | 2.5 ml | Vitamin C (VTC) | 2.5 g |
| Black Cumin Seed Oil (BCS) | 50 ml | Vitamin E (VTE) | 2.5 g |
| Palmarosa Oil (PLO) | 2.5 ml | | |
| Panthenol (PNT) | 10 ml | | |
| Rosemary Oil (RMO) | 5 ml | | |
| Sea Buckthorn Oil (SBO) | 5 ml | | |
| Tamanu Oil (TMU) | 5 ml | | |

Abrasions, Cuts, & Minor Burns

Example 5

Figure 2A:
FIG. 2A shows an abrasion of the palm.
Figure 2B:
FIG. 2B shows a cut on the leg [permission granted—ClockFace].
Figure 2C:
FIG. 2C shows a burn to the top of a hand.

There are many first aid products currently on the market focused on treating abrasions (FIG. 2A), cuts (FIG. 2B), and minor burns (FIG. 2C) that have a variety of effectiveness and varied times to achieve healing compared to no treatment besides cleansing. One of the oldest compositions and most successful in terms of global distribution is a triple antibiotic ointment called NEOSPORIN™ by Johnson & Johnson (1952). Its formulation is very basic including three antibiotics: neomycin, polymyxin, and bacitracin. It also contains petroleum jelly, cocoa butter, cottonseed oil, sodium pyruvate, and tocopheryl acetate. Since many users develop allergies to neomycin, Johnson & Johnson offers a double antibiotic composition containing only bacitracin and polymyxin called POLYSPORIN™. The NEOSPORIN™ composition, while very popular for years, has essentially no ingredients proven to hasten healing. Petroleum jelly from oil compositions is also called Vaseline as branded by Unilever and only prevents moisture loss from the skin. The only potentially healing agent would be cocoa butter that is processed from whole cocoa beans and melts at just under body temperature, making it convenient to use in many compositions, including soaps and lotions. Cocoa butter contains Oleic acid (34.5%—Omega-9, used in food and soap), Stearic acid (34.5%—surfactant, detergents, soaps, lubricants), Palmitic acid (26.0%—soaps, food compositions, cosmetics), Linoleic acid (3.2%—Omega-6, essential oil, surfactant, anti-inflammatory), Arachidic acid (1.0%—detergents, lubricants) and Palmitoleic acid (0.3%—Omega-7). Cottonseed oil is a cooking oil. Sodium pyruvate protects against peroxides. Tocopherol acetate is a form of Vitamin E that can resist acid destruction. None of these NEOSPORIN™ components are able to hasten healing in the skin.

Establishing formulations for these problems is complicated by utilizing many of the components collected due to their long history of enabling accelerated healing. The disclosed composition has been used by nearly a dozen people who had received abrasions, cuts, and minor burns at different times. The results of their use of the composition show a consistent ability to heal these skin wounds rapidly, usually within 2 to 7 days depending upon the size of the wound. Small wounds or injuries usually are sealed and healed within 2-4 days. The larger abrasions on extremities heal well with little evidence of scarring within 7-9 days that would normally take 10 to 14 days. So these results demonstrate a composition that clearly improves healing in a short time scale with little scarring after it is healed. There also is a clear protection against microbial contamination and infection at the same time. In fact, one can simply apply the composition to an infected finger nail or toe nail that had that had been previously cut or injured that over a few days will show the infection has been eliminated while the composition continues to hasten healing.

Example 6

A 39 year white male was a bicycle rider going on trails in the area. He fell while riding a trail and landed on his left side inducing a large, 5 by 12 cm skin abrasion with bleeding. On return from the ride, he washed it off and placed NEOSPORIN™ on the wound. The next day, he was offered to replace the NEOSPORIN™ with the disclosed composition. His experience with NEOSPORIN™ for this kind of partial thickness skin wound, would take 10 to 14 days for it to heal. The three times a day usage of this product permitted the healing to be essentially over in 5-6 days with little evidence of scarring.

Example 7

A 70 year old white male fell at home while working outside and suffered a superficial laceration of the skin on the knee. The disclosed composition was applied to the injury after cleaning. The disclosed composition was applied three times a day. By the second day, the wound was closed and no longer weeping fluid and had lost most of its pain. By the fourth day, the wound was essentially healed over and without pain or sign of infection.

Example 8

A 52 year old white male applied the disclosed composition on multiple occasions of scratches, scrapes, and cuts. The disclosed composition treats injuries without infection, and healed in half the time usually required for NEOSPORIN™.

Table 6 lists the composition formulation for treatment of cuts, abrasions, and minor burns.

TABLE 6

Abrasions, Cuts, and Minor Burns Composition Formulation

| Hydrophobic Components | amount | Hydrophilic Components | amount |
|---|---|---|---|
| a-Pinene (APN) | 60 ml | 1-Tetradecanol | 2.5 g |
| Acai Berry | 10 ml | AF (Artie Fish) Collagen (AFC) | 40 g |
| Anethole Anise Camphor | 5 ml | *Agave* nectar (AGV) | 10 ml |
| Argan Nut Oil (AGN) | 5 ml | Alanine (ALA) | 5 g |
| Baobab Oil (BAB) | 5 ml | *Aloe Vera* Leaf Gel (AVLG) | 275 g |
| Bees Wax (BW) | 40 g | Arginine (ARG) | 5 g |
| Benzoin (BZN) | 4 ml | Distilled water | 500 ml |
| Benzyl Alcohol (BA) | 50 ml | Ferulic Acid (FRA) | 10 g |
| Cabreuva Oil | 5 ml | Glutamine (GLU) | 5 g |
| *Calendula* Oil (CDA) | 5 ml | Glycine (GLY) | 5 g |
| *Camellia* Oil (CMA) | 10 ml | Histidine (HST) | 5 g |
| Capaiba Oil (CPO) | 10 ml | Hydroxyproline (HDP) | 5 g |
| Caprylic acid (CCT) | 10 ml | Isoleucine (ISL) | 5 g |
| Carvacrol (CVC) | 5 ml | Lecithin (LCT) | 25 g |
| Caryophyllene (CAP) | 10 ml | Leucine (LUC) | 5 g |
| Cetyl Alcohol (CTA) | 40 g | Linoleic Acid (LOA) | 5 ml |
| Chamomile German Oil (CGB) | 10 ml | Lysine (LYS) | 5 g |
| Ghana Shea Butter (GSB) | 275 g | Methyl Sulfonyl Methane (MSM) | 25 g |
| Glycerol (GLY) | 10 ml | Niacinamide (NCM) | 2.5 g |
| Kaempferol | 5 g | Oleic Acid (OLA) | 5 ml |
| Kanuka Oil (KNO) | 2.5 ml | Praline (PRL) | 5 g |
| Limonene Oil (LMN) | 40 ml | Protocatechuic Acid (PCT) | 10 g |
| *Litsea Cubeba* Oil (LCO) | 5 ml | Sericin | 50 g |
| Myrrh | 5 ml | Sodium Polyacrylate | 20 g |
| Nerolina Oil (NRL) | 2.5 ml | Vitamin A (VTA) | 2.5 g |
| Niaouli Oil | 5 ml | Vitamin B3 (VTB3) or Niacin | 12.5 g |
| Black Cumin Seed Oil (BCS) | 50 ml | Vitamin C (VTC) | 2.5 g |
| Panthenol (PNT) | 10 ml | Vitamin E (VTE) | 2.5 g |
| Peppermint | 5 ml | | |
| Rosemary Oil (RMO) | 5 ml | | |
| Sachi Inchi oil | 5 ml | | |
| Sea Buckthorn Oil (SBO) | 5 ml | | |
| Tamanu Oil (TMU) | 5 ml | | |
| Terpineol | 5 ml | | |
| Thyme Red, White | 5 ml | | |

Peyronie's Disease or Induratio Penis Plastica (IPP)

Example 9

Figure 3:
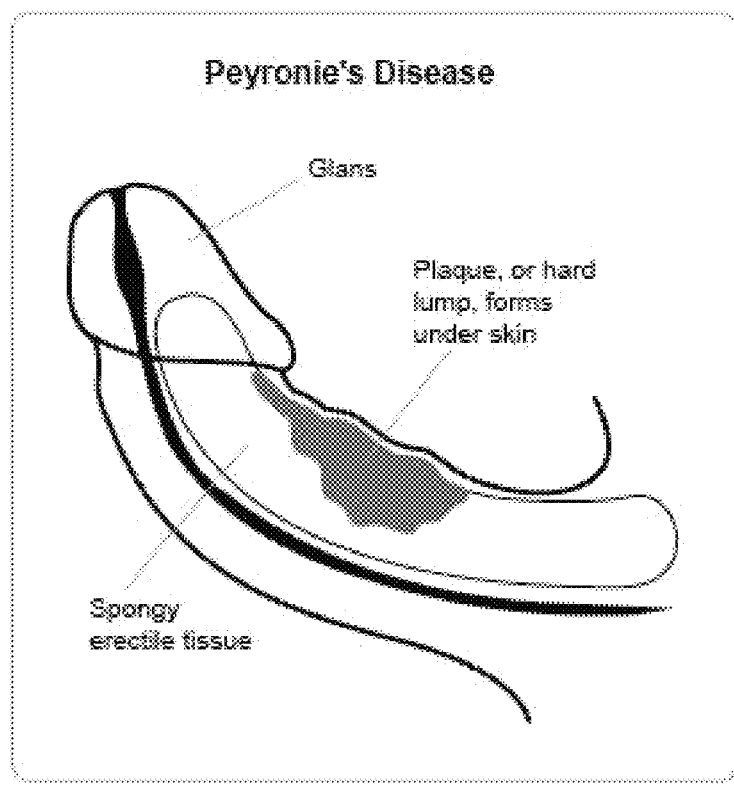
FIG. 3 illustrates the curvature of the penis due to Peyronie's Disease.

Peyronie's Disease is a connective tissue disorder of the penis affecting 5% of the male population. It involves fibrous plaques developing along the fibrous sheath, the tunica albuginea, that surrounds the spongy erectile tissue, the corpus cavernosa, in the penis. When the penis fills with blood and erects, these fibrous plaques or bands prevent that portion of the penis from erecting properly. This leads to two types of deformities of the penis: the more common is a marked curvature of the penis in any direction at the point of the stricture (FIG. 3) while the least common is an hour glass stricture completely around the penis. Regardless of the type of stricture, as it progresses it causes more deformity. Penile penetration during intercourse becomes painful and eventually impossible. A small percentage of men with Dupuytren's Disease or Contracture also develop Peyronie's Disease for unknown reasons. There is no known cause of these progressive deformities of the penis. Without treatment, 10-15% will spontaneously improve over time, 40-50% will get worse, and 35-50% will not change. Currently, there is no effective treatment that does not include a high risk of doing more harm. Injection of collagenase into the plaques can soften them to reduce the strictures causing the deformities. However, if the physician happens to inject collagenase into the spongy erectile tissue, it can be weakened and fracture during intercourse producing a non-functional penis. Trying to surgically remove these plaques has a high risk of permanently injuring the penis, which can lead to internal fracture leading to non-function regarding intercourse. At this point, there is no effective treatment to this disease without a high risk of making it worse.

Due to the observations of the effect of the disclosed composition in people with Dupuytren's Disease and Contracture, a similar preparation was tried in men with untreated Peyronie's disease. Four patients were selected and provided with the topical composition to apply twice a day to the region of the penis involved. At one month follow up, the first two patients, one with a marked lateral curve and the other with an hour-glass deformity near the end of the penis returned quite pleased with their results. The marked curve patient's penis had the curvature reduced by 50% at that time permitting him to again have intercourse. The second patient with the hour-glass deformity had his stricture essentially resolve in this time leaving him to have fairly normal intercourse as well. They are continuing to use the medication. The second two patients are in treatment currently and will be returning with their one month follow up soon.

Example 10

A 34 year old, middle eastern male with Peyronie's disease of the cicatrix, circumferential type with significant curvature of the penis restricting intercourse. Photos and measurements were made after injection of agents into the base of the penis to cause a maximal erection of the penis. The patient was given the disclosed composition for treatment of Peyronie's Disease and told to apply it twice a day to the lesion near by tissue in the penis. On 3 month follow up, the penile constricting lesion had significantly loosened with a resulting reduction of the curvature from 80 degrees down to 45 degrees which has been sufficient to permit intercourse. Additional treatment and follow up are underway.

Example 11

A 38 year old, middle eastern male with Peyronie's disease of the dorsal ligament as a thickened nodule causing a dorsal and partially lateral curvature of the penis with significant curvature of the penis restricting intercourse. Photos and measurements were made after injection of agents into the base of the penis to cause a maximal erection of the penis. The patient was given the disclosed composition for treatment of Peyronie's Disease and told to apply it twice a day to the lesion near by tissue in the penis. After 4 months of follow up, the dorsal penile ligament lesion had softened permitting the curvature to reduce from 65 degrees down to 35 degrees permitting the ability to have intercourse again. Treatment continues with additional observation periods in follow up.

Table 7 lists the composition formulation for treatment of Peyronie's Disease or Induration Penis Plastica.

TABLE 7

Peyronie's Disease or Induration Penis Plastica Composition Formulation

| Hydrophobic Components | amount | Hydrophilic Components | amount |
|---|---|---|---|
| a-Pinene (APN) | 60 ml | 1-Tetradecanol | 2.5 g |
| Acai Berry | 10 ml | AF (Artie Fish) Collagen (AFC) | 40 g |
| Anethole Anise Camphor | 5 ml | *Agave* nectar (AGV) | 10 ml |
| Argan Nut Oil (AGN) | 5 ml | Alanine (ALA) | 5 g |
| Bees Wax (BW) | 40 g | *Aloe Vera* Leaf Gel (AVLG) | 275 g |
| Benzoin (BZN) | 4 ml | Arginine (ARG) | 5 g |
| Benzyl Alcohol (BA) | 50 ml | Distilled water | 500 ml |
| *Calendula* Oil (CDA) | 5 ml | Ferulic Acid (FRA) | 10 g |
| *Camellia* Oil (CMA) | 10 ml | Glutamine (GLU) | 5 g |
| Capaiba Oil (CPO) | 10 ml | Glycine (GLY) | 5 g |
| Caprylic, Capric Triglyceride (CCT) | 10 ml | Histidine (HST) | 5 g |
| Carvacrol (CVC) | 5 ml | Hydroxyproline (HDP) | 5 g |
| Caryophyllene (CAP) | 10 ml | Isoleucine (ISL) | 5 g |
| Cetyl Alcohol (CTA) | 40 g | Lecithin (LCT) | 25 g |
| Chamomile German Oil (CGB) | 10 ml | Leucine (LUC) | 5 g |
| Elemi Oil (EMO) | 5 ml | Linoleic Acid (LOA) | 5 ml |
| Ghana Shea Butter (GSB) | 275 g | Lysine (LYS) | 5 g |
| Glycerol (GLY) | 10 ml | Methyl Sulfonyl Methane (MSM) | 25 g |
| Kanuka Oil (KNO) | 2.5 ml | Niacinamide (NCM) | 2.5 g |
| Limonene Oil (LMN) | 40 ml | Oleic Acid (OLA) | 5 ml |
| *Litsea Cubeba* Oil (LCO) | 5 ml | Praline (PRL) | 5 g |
| Marula Oil (MRL) | 2.5 ml | Protocatechuic Acid (PCT) | 10 g |
| Black Cumin Seed Oil (BCS) | 50 ml | Sericin | 50 g |
| Palo Santo | 2.5 ml | Sodium Polyacrylate | 20 g |
| Panthenol (PNT) | 10 ml | Vitamin A (VTA) | 2.5 g |
| Rosemary Oil (RMO) | 5 ml | Vitamin B3 (VTB3) or Niacin | 12.5 g |
| Sea Buckthorn Oil (SBO) | 5 ml | Vitamin C (VTC) | 2.5 g |
| Terpineol | 5 ml | Vitamin E (VTE) | 2.5 g |

Exposed Aging Skin

Example 12

Figure 4A:
FIG. 4A shows damage to the skin of the forearm of an elderly person.

As everyone ages overtime, their skin is under easy observation, and readily shows multiple aging changes. The age relating skin changes include thinning of the outer surface of the skin, loss of substance and softness in both the outer and deeper skin components, wrinkles, easy bruising, appearance of pigmented flat lesions, scaly lesions, skin tags, loss of hair, and scratches which take much longer to heal (FIG. 4A). The appearance and the rate of the increasing incidence of these aging disorders predominantly depend upon the individual's history of sun exposure, history and the degree of routine skin care, race, as well as, genetics. An increasing incidence of skin cancers also will occur with increasing age. Routine skin care of the face, as well as, the use of sun protectants is more common in both men and women than routine skin care of the hands, arms, legs, and feet. Thus, it is very common to see multiple types of accelerated skin aging problems in the arms and hands of the vast majority of the aging populations.

Figure 4B:
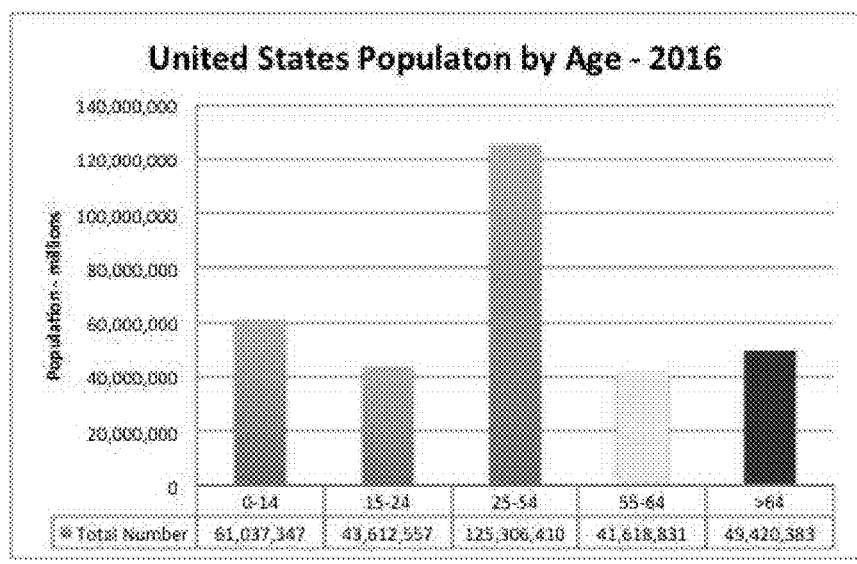
FIG. 4B is a graph of age range of the United States, Year 2016.

If one examines the USA population by age from 2016, one finds there are 49.4 million people over the age of 64 years of age (FIG. 4B). This is 15.2% of the population that is subject to aging skin and would certainly have the skin aging readily observable and open for potential treatment. Of this age group, 44.3% are males and 55.7% are females. While aging skin can certainly begin in the 55 year olds, it is not as frequent as in the >64 year olds.

Example 13

A 72 year old, white male, had progressive hair loss on the dorsal surfaces of both forearms and hands that had progressed over the last several years. Skin thinning had also progressed to the marked reduction of surface hair and easy bruising of the skin. Several superficial skin tears had also occurred leaving scars.

There were many actinic keratoses present on these same surfaces from previous sun damage. This person had been using moisturizers for several years on these surfaces without any effect on delaying these-age related changes. The disclosed composition was applied to the dorsal surface of the right forearm while moisturizers were continued on the left forearm. Within a couple of months, there was noticeable difference in the appearance of the two forearms. The left forearm was unchanged. The right forearm skin had begun to thicken with increased terger of the skin noted along with the epidermal layer clearly thickening. The actinic keratoses began to flatten and become thinner and smoother. Then, new hair began to appear across the right forearm without any new hair forming on the left forearm. The test subject was allowed to apply the disclosed composition to both forearms after the changes became quite obvious when examining both forearms. Several months of continued use of the disclosed composition on both forearms shows established hair, both dark and white, growing well to its normal length, increased dermal thickening, strengthening and thickening of the epidermis without any new tears, and ongoing reduction in the actinic keratoses size and appearance.

Table 8 lists the composition formulation for treatment of exposed aging skin.

TABLE 8

Old-Age Skin Treatment Composition Formulation

| Hydrophobic Components | amount | Hydrophilic Components | amount |
|---|---|---|---|
| a-Pinene (APN) | 60 ml | 1-Tetradecanol | 2.5 g |
| Acai Berry | 10 ml | AF (Artie Fish) Collagen (AFC) | 40 g |
| Argan Nut Oil (AGN) | 5 ml | *Agave* nectar (AGV) | 10 ml |
| Baobab Oil (BAB) | 5 ml | Alanine (ALA) | 5 g |
| Bees Wax (BW) | 40 g | *Aloe Vera* Leaf Gel (AVLG) | 275 g |
| Benzoin (BZN) | 4 ml | Arginine (ARG) | 5 g |
| Benzyl Alcohol (BA) | 50 ml | Distilled water | 500 ml |
| Cabreuva Oil | 5 ml | Ferulic Acid (FRA) | 10 g |
| Caffeic acid | 5 g | Glutamine (GLU) | 5 g |
| *Calendula* Oil (CDA) | 5 ml | Glycine (GLY) | 5 g |
| *Camellia* Oil (CMA) | 10 ml | Histidine (HST) | 5 g |
| Capaiba Oil (CPO) | 10 ml | Hydroxyproline (HDP) | 5 g |
| Caprylic, Capric Triglyceride (CCT) | 10 ml | Isoleucine (ISL) | 5 g |
| Carvacrol (CVC) | 5 ml | Lecithin (LCT) | 25 g |
| Caryophyllene (CAP) | 10 ml | Leucine (LUC) | 5 g |
| Cetyl Alcohol (CTA) | 40 g | Linoleic Acid (LOA) | 5 ml |
| Chamomile German Oil (CGB) | 10 ml | Lysine (LYS) | 5 g |
| Elemi Oil (EMO) | 5 ml | Methyl Sulfonyl Methane (MSM) | 25 g |
| Geranium Oil (GER) | 2.5 ml | Niacinamide (NCM) | 2.5 g |
| Ghana Shea Butter (GSB) | 275 g | Oleic Acid (OLA) | 5 ml |
| Glycerol (GLY) | 10 ml | Praline (PRL) | 5 g |
| Ho Wood Oil (HWO) | 2.5 ml | Protocatechuic Acid (PCT) | 10 g |
| Jasmine Oil (JAS) | 2.5 ml | Sericin | 50 g |
| Kaempferol | 5 g | Sodium Polyacrylate | 20 g |
| Kanuka Oil (KNO) | 2.5 ml | Valine (VAL) | 5 g |
| Lavandin Oil (LVO) | 10 ml | Vitamin A (VTA) | 2.5 g |
| Limonene Oil (LMN) | 40 ml | Vitamin B3 (VTB3) or Niacin | 12.5 g |
| *Litsea Cubeba* Oil (LCO) | 5 ml | Vitamin C (VTC) | 2.5 g |
| Marula Oil (MRL) | 2.5 ml | Vitamin E (VTE) | 2.5 g |
| Myrrh | 5 ml | | |
| Nerolina Oil (NRL) | 2.5 ml | | |
| Niaouli Oil | 5 ml | | |
| Black Cumin Seed Oil (BCS) | 50 ml | | |
| Palmarosa Oil (PLO) | 2.5 ml | | |
| Palo Santo | 2.5 ml | | |
| Panthenol (PNT) | 10 ml | | |
| Peppermint | 5 ml | | |
| Rose Hip Seed oil | 5 ml | | |
| Rosemary Oil (RMO) | 5 ml | | |
| Sachi Inchi oil | 5 ml | | |
| Sea Buckthorn Oil (SBO) | 5 ml | | |
| Tamanu Oil (TMU) | 5 ml | | |
| Vetiver | 2.5 ml | | |

Toe Nail Fungus

Example 14

Figure 5:
FIG. 5 shows toes with severe fungus infection of toe nails [permission granted—James Heilman, Md.].

Toe nail fungus is medically known as onychomycosis, or tinea unguium, commonly affects toe nails and can be progressive to the state of nail destruction, if not treated properly (FIG. 5). It can also affect the finger nails. It is the most common of all the nail afflictions affecting 10% of the population and represents 50% of all nail afflictions. The progression is from mild forms to the most severe with loss of most of the normal nail.

The pathogens involved in onchyomycosis are all represented in the fungus kingdom that includes dermatophytes in the western world and *Candida* and non-dermatophyes in the tropics and subtropics. The dermatophytes most common representative is *Trichophyton rubrum* with multiple related species. *Candida* species predominantly affect the finger nails, rather than the toe nails. The non-dermatophytes are predominantly molds, mostly from the genus of *Neoscytalidium, Scopulariopsis,* and *Aspergillus*. Conditions that can be confused with onychomycosis include nail psoriasis, lichen planus, contact dermatitis, and nail bed tumors such as melanoma, thrauma, and Q yellow nail syndrome.

Six patients with this condition have used the disclosed composition for treating infected toe nails. One patient had the most involvement with all ten toe nails involved to the severe stage. His podiatrist suggested he needed to have all ten nails removed to enable healing his problem. He was supplied with the disclosed formulation with application once a day after showering, as well as, keeping his nails trimmed well through out the treatment. Within one month, most all of the nails were growing out with normal nails below the fungal infected outer edge. By two to three months, all of the toe nails had been eliminated from their fungus. The other patients had involvements of lesser degree, but all patients had eliminated their toe nail fungus in a similar time frame.

Example 15

A 66 year old white male had chronic, severe onychomycosis involving fungal infections of all of his toe nails and was being followed by a podiatrist. After trying several known potential remedies over months to a few years, the podiatrist told this patient that there was nothing else topically to help his problem. He asked to schedule him for removal of all of his toenails so he could remove the difficult to heal infected toenails and clear the growth beds that were not responding to his treatment. He delayed the proposed surgery and started applying the disclosed composition daily to his nails after showering. Before starting the treatment, the podiatrist cleaned the extra debris from the infection and cut the nails close. Within a few weeks, the toenails began to heal and growing out healthy nails from the nail beds. When all of the infected toenail and base had been cleared, he had normal looking nails and no longer needed the surgery the podiatrist wanted to perform.

Example 16

A 69 year old white male had developed chronic onychomycosis, or toe nail fungus, involving most of the toe nails on both feet, but with different degrees of infection. The disclosed composition was applied once a day on all of the nails after shower or bath. The nails were to be kept well clipped and the disclosed composition applied daily. Over a few weeks, the mildly infected nails cleared of their fungus, but the more heavily infected nails took a few more weeks to clear. But, at the end, all of the nails recovered from their fungal infection.

Table 9 lists the composition formulation for treatment of toe nail fungus.

TABLE 9

Toe Nail Fungus Composition Formulation

| Hydrophobic Components | amount | Hydrophilic Components | amount |
| --- | --- | --- | --- |
| a-Pinene (APN) | 60 ml | 1-Tetradecanol | 2.5 g |
| Acai Berry | 10 ml | AF (Artie Fish) Collagen (AFC) | 40 g |
| Anethole Anise Camphor | 5 ml | *Agave* nectar (AGV) | 10 ml |
| Argan Nut Oil (AGN) | 5 ml | Alanine (ALA) | 5 g |
| Baobab Oil (BAB) | 5 ml | *Aloe Vera* Leaf Gel (AVLG) | 275 g |
| Bees Wax (BW) | 40 g | Arginine (ARG) | 5 g |
| Benzoin (BZN) | 4 ml | Distilled water | 500 ml |
| Benzyl Alcohol (BA) | 50 ml | Ferulic Acid (FRA) | 10 g |
| Cabreuva Oil | 5 ml | Glutamine (GLU) | 5 g |
| *Calendula* Oil (CDA) | 5 ml | Glycine (GLY) | 5 g |
| *Camellia* Oil (CMA) | 10 ml | Histidine (HST) | 5 g |
| Capaiba Oil (CPO) | 10 ml | Hydroxyproline (HDP) | 5 g |
| Caprylic acid (CCT) | 10 ml | Isoleucine (ISL) | 5 g |
| Carvacrol (CVC) | 5 ml | Lecithin (LCT) | 25 g |
| Cetyl Alcohol (CTA) | 40 g | Leucine (LUC) | 5 g |
| Chamomile German Oil (CGB) | 10 ml | Linoleic Acid (LOA) | 5 ml |
| Ghana Shea Butter (GSB) | 275 g | Lysine (LYS) | 5 g |
| Glycerol (GLY) | 10 ml | Methyl Sulfonyl Methane (MSM) | 25 gm |
| Kanuka Oil (KNO) | 2.5 ml | Niacinamide (NCM) | 2.5 g |
| Limonene Oil (LMN) | 40 ml | Oleic Acid (OLA) | 5 ml |
| *Litsea Cubeba* Oil (LCO) | 5 ml | Praline (PRL) | 5 g |
| Myrrh | 5 ml | Protocatechuic Acid (PCT) | 10 g |
| Niaouli Oil | 5 ml | Sericin | 50 g |
| Black Cumin Seed Oil (BCS) | 50 ml | Sodium Polyacrylate | 20 g |
| Panthenol (PNT) | 10 ml | Vitamin A (VTA) | 2.5 g |
| Peppermint | 5 ml | Vitamin B3 (VTB3) or Niacin | 12.5 g |
| Sea Buckthorn Oil (SBO) | 5 ml | Vitamin C (VTC) | 2.5 g |

TABLE 9-continued

Toe Nail Fungus Composition Formulation

| Hydrophobic Components | amount | Hydrophilic Components | amount |
|---|---|---|---|
| Terpineol | 5 ml | Vitamin E (VTE) | 2.5 g |
| Thyme Red, White | 5 ml | | |
| Winter Savory | 5 ml | | |

Aphthous Ulcers

Example 17

Figure 6:
FIG. 6 shows an aphthous ulcer in the mouth of a patient [permission granted—Ryanfransen at English Wikipedia].

Aphthous ulcers or stomatitis are characterized by repeated, benign and non-contagious oral cavity ulcerations that are self-limited to usually 7-10 days, as shown in FIG. 6. These are painful and sensitive to increased pain by topical exposure to compositions with excessive pH, spices, and increased temperature. Episodes usually occur 3-6 times a year for several years around the time of adolescence. There is no known cause, but are thought to be multi-factorial.

While the ulceration triggers are not identified, the ulcers develop due to immune cell reactions from T-cells, mast cells, and macrophages to unknown triggers with the emphasis on T-cell involvement. Forty percent of persons getting these lesions have a family history of involvement. Some episodes seem to clearly be responding to acute, excessive stress in those who get these ulcers, but most do not. The natural duration of 7-10 days remains fairly uniform, even in spite of several different types of proposed treatments.

The disclosed composition has demonstrated the ability to reduce the duration of these ulcers to 2-4 days while relieving the pain. However, it does not appear to prevent the regular occurrence of these ulcers. Approximately 10 patients have used this formulation and uniformly experience a shorter duration of time and a reduction of pain.

Example 18

A 65 year old white male, was having occasional episodes of aphthous ulcers of the mouth that were typical in severity and duration with pain lasting 7 to 10 days and final clearing from 2 to 2.5 weeks. These aphthous ulcers were occurring every three to four months without an obvious cause. The disclosed composition was applied at the start of an episode. The disclosed composition was designed to be thick enough to stay within the bed of the ulcer with application 2 to 4 times a day. From starting the use of the disclosed composition on the first day of the lesion appearing, and treating it 3 times a day after meals and again at bed time, the ulcer lost its pain in 2-3 days and disappeared in 4-5 days. Due to benzocaine being used as a product ingredient, the ulcer had a significant decrease in pain during the treatment phase and prior to its healing.

Table 10 lists the composition formulation for treatment of aphthous ulcers of the mouth.

TABLE 10

Aphthous Ulcers of the Mouth Composition Formulation

| Hydrophobic Components | amount | Hydrophilic Components | amount |
|---|---|---|---|
| a-Pinene (APN) | 60 ml | 1-Tetradecanol | 2.5 g |
| Acai Berry | 10 ml | AF (Artie Fish) Collagen (AFC) | 40 g |
| Anethole Anise Camphor | 5 ml | *Agave* nectar (AGV) | 10 ml |
| Argan Nut Oil (AGN) | 5 ml | Alanine (ALA) | 5 g |
| Baobab Oil (BAB) | 5 ml | *Aloe Vera* Leaf Gel (AVLG) | 275 g |
| Bees Wax (BW) | 40 g | Arginine (ARG) | 5 g |
| Benzoin (BZN) | 4 ml | Benzocaine | 3 g |
| Benzyl Alcohol (BA) | 50 ml | Distilled water | 500 ml |
| Cabreuva Oil | 5 ml | Ferulic Acid (FRA) | 10 g |
| Caffeic acid | 5 g | Glutamine (GLU) | 5 g |
| *Calendula* Oil (CDA) | 5 ml | Glycine (GLY) | 5 g |
| Capaiba Oil (CPO) | 10 ml | Histidine (HST) | 5 g |
| Caprylic acid (CCT) | 10 ml | Hydroxyproline (HDP) | 5 g |
| Carvacrol (CVC) | 5 ml | Isoleucine (ISL) | 5 g |
| Caryophyllene (CAP) | 10 ml | Lecithin (LCT) | 25 g |
| Cedarwood essential Oil | 2.5 nl | Leucine (LUC) | 5 g |
| Cetyl Alcohol (CTA) | 40 g | Linoleic Acid (LOA) | 5 ml |
| Chamomile German Oil (CGB) | 10 ml | Lysine (LYS) | 5 g |
| Ghana Shea Butter (GSB) | 275 g | Methyl Sulfonyl Methane (MSM) | 25 g |
| Glycerol (GLY) | 10 ml | Niacinamide (NCM) | 2.5 g |
| Kanuka Oil (KNO) | 2.5 ml | Oleic Acid (OLA) | 5 ml |
| Limonene Oil (LMN) | 40 ml | Praline (PRL) | 5 g |
| *Litsea Cubeba* Oil (LCO) | 5 ml | Protocatechuic Acid (PCT) | 10 g |
| Niaouli Oil | 5 ml | Sericin | 50 g |
| Black Cumin Seed Oil (BCS) | 50 ml | Sodium Polyacrylate | 20 g |
| Panthenol (PNT) | 10 ml | Vitamin A (VTA) | 2.5 g |
| Peppermint | 5 ml | Vitamin B3 (VTB3) or Niacin | 12.5 g |
| Sea Buckthorn Oil (SBO) | 5 ml | Vitamin C (VTC) | 2.5 g |
| Thyme Red, White | 5 ml | Vitamin E (VTE) | 2.5 g |
| Winter Savory | 5 ml | | |

Cutaneous Involvement of Scleroderma

Example 19

Figure 7:
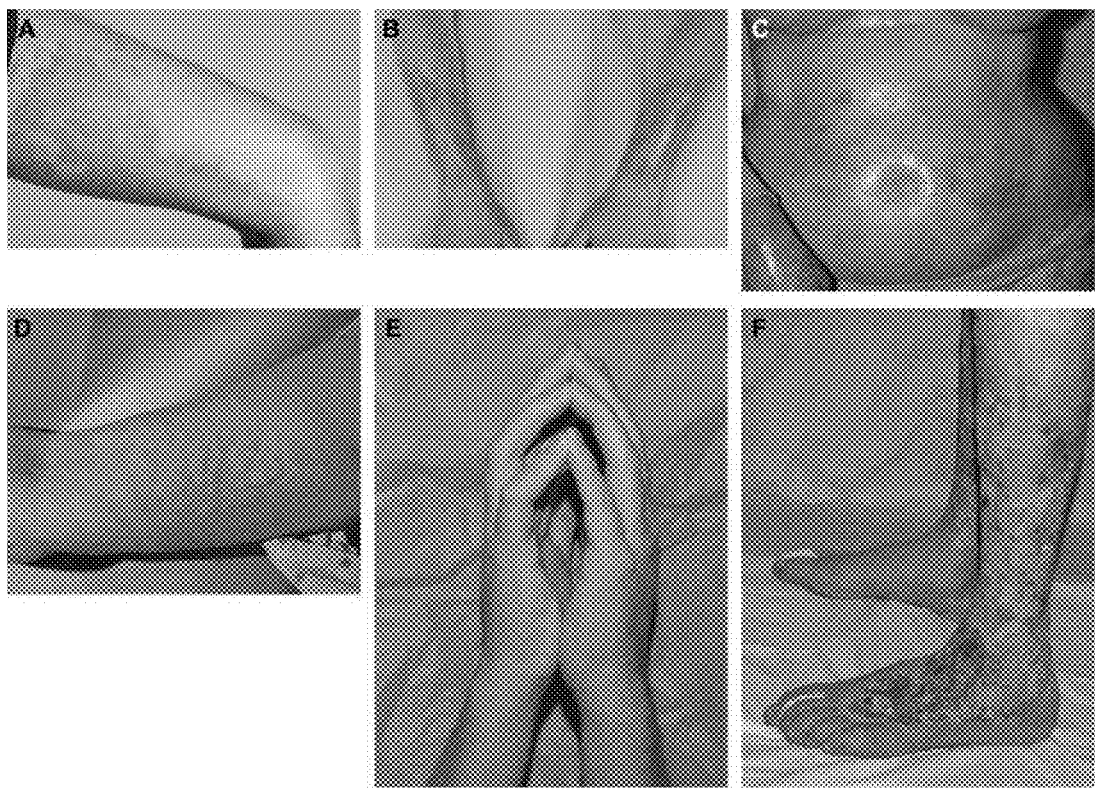
FIG. 7 shows several photographs of people with cutaneous scleraderma

Scleroderma is a systemic disease that results in progressive fibrosis of organs starting with skin lesions that can then progress to involving major organs, such as, the heart, lungs, intestines and kidneys. The pathophysiology for the skin appears to involve the laying down in a random orientation of collagen much like scar formation diffusively in the subcutaneous tissues. This leads to joint immobilization starting in the fingers and spreading into the wrists and elbows as well as in the toes and ankle (FIG. 7). Its increased pressure beneath the skin also reduces blood flow causing extensive Raynaud's phenomenon, or skin blanching episodes on the digits that readily leads to poorly healing ulcerations and potential digit loss.

A white female, 52 years old developed Scleroderma with cutaneous manifestations that resulted in contractures of all the joints of the fingers on both hands, both wrists, and early limitations of both elbows. Fibrosis of the fingers only left about 5-10% motion in all fingers. The wrist joints were about 50% inhibited with elbows about 30% inhibited, all due to the subcutaneous fibrosis. She had evidence of some areas of collagen formation beneath the skin in both upper extremities. The patient's primary complaint was that her skin was giving her so many symptoms on a 24 hour basis; she was treating subcutaneous discomfort in both arms with over the counter skin moisturizers every two hours without much relief, including at night. She tested the disclosed composition on the skin of both arms and found symptomatic relief. Instead of every two hours, she found by applying this product only every 12 hours, she got improved relief of her previous cutaneous symptoms. In addition, she had developed significant Raynaud's Phenomenon on fingers on both hands with early joint ulcerations noted on several fingers. With some early systemic symptoms, she was treated with an oral drug for Scleroderma for several months but systemic disease progression continued. She underwent bone marrow ablation and received a bone marrow transplant and is currently under remission. The disclosed composition was discontinued when her disease progression began to advance to systemic symptoms.

Table 11 lists the composition formulation for treatment of cutaneous scleroderma.

TABLE 11

| Cutaneous Scleroderma Composition Formulation | | | |
|---|---|---|---|
| Hydrophobic Components | amount | Hydrophilic Components | amount |
| a-Pinene (APN) | 60 ml | 1-Tetradecanol | 2.5 g |
| Acai Berry | 10 ml | AF (Artie Fish) Collagen (AFC) | 40 g |
| Argan Nut Oil (AGN) | 5 ml | *Agave* nectar (AGV) | 10 ml |
| Baobab Oil (BAB) | 5 ml | Alanine (ALA) | 5 g |
| Bees Wax (BW) | 40 g | *Aloe Vera* Leaf Gel (AVLG) | 275 g |
| Benzoin (BZN) | 4 ml | Arginine (ARG) | 5 g |
| Benzyl Alcohol (BA) | 50 ml | Distilled water | 500 ml |
| *Calendula* Oil (CDA) | 5 ml | Ferulic Acid (FRA) | 10 g |
| *Camellia* Oil (CMA) | 10 ml | Glutamine (GLU) | 5 g |
| Capaiba Oil (CPO) | 10 ml | Glycine (GLY) | 5 g |
| Caprylic, Capric Triglyceride (CCT) | 10 ml | Histidine (HST) | 5 g |
| Carvacrol (CVC) | 5 ml | Hydroxyproline (HDP) | 5 g |
| Caryophyllene (CAP) | 10 ml | Isoleucine (ISL) | 5 g |
| Cetyl Alcohol (CTA) | 40 g | Lecithin (LCT) | 25 g |
| Chamomile German Oil (CGB) | 10 ml | Leucine (LUC) | 5 g |
| Elemi Oil (EMO) | 5 ml | Linoleic Acid (LOA) | 5 ml |
| Geranium Oil (GER) | 2.5 ml | Lysine (LYS) | 5 g |
| Ghana Shea Butter (GSB) | 275 g | Methyl Sulfonyl Methane (MSM) | 25 g |
| Glycerol (GLY) | 10 ml | Niacinamide (NCM) | 2.5 g |
| Ho Wood Oil (HWO) | 2.5 ml | Oleic Acid (OLA) | 5 ml |
| Jasmine Oil (JAS) | 2.5 ml | Praline (PRL) | 5 g |
| Kanuka Oil (KNO) | 2.5 ml | Protocatechuic Acid (PCT) | 10 g |
| Lavandin Oil (LVO) | 10 ml | Sericin | 50 g |
| Limonene Oil (LMN) | 40 ml | Sodium Polyacrylate | 20 g |
| *Litsea Cubeba* Oil (LCO) | 5 ml | Vitamin A (VTA) | 2.5 g |
| Marula Oil (MRL) | 2.5 ml | Vitamin B3 (VTB3) or Niacin | 12.5 g |
| Nerolina Oil (NRL) | 2.5 ml | Vitamin C (VTC) | 2.5 g |
| Black Cumin Seed Oil (BCS) | 50 ml | Vitamin E (VTE) | 2.5 g |
| Palo Santo | 2.5 ml | | |
| Panthenol (PNT) | 10 ml | | |
| Rose Hip Seed Oil | 10 ml | | |
| Rosemary Oil (RMO) | 5 ml | | |
| Sachi Inchi oil | 5 ml | | |
| Sea Buckthorn Oil (SBO) | 5 ml | | |
| Tamanu Oil (TMU) | 5 ml | | |

Raynaud's (or Renaud's) Phenomenon Preparation

Example 20

Figure 8:
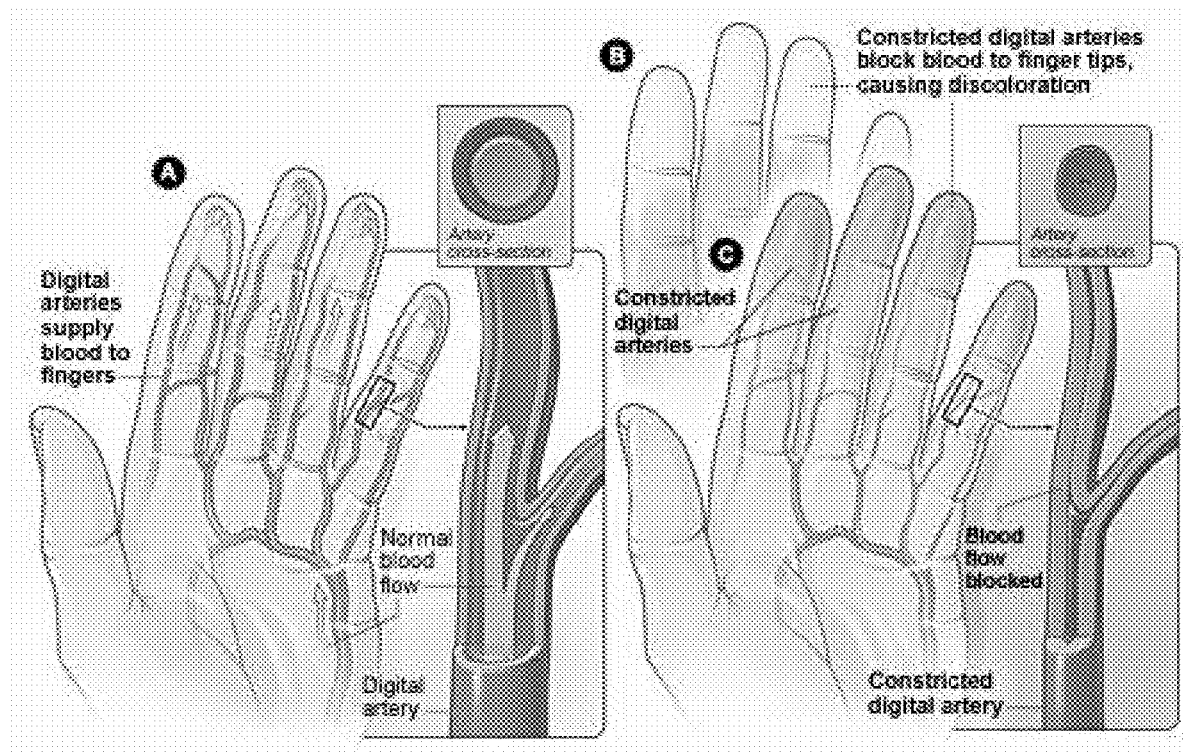
FIG. 8 illustrates the effects of Raynaud's phenomenon on the hand.

Raynaud's Phenomenon or Syndrome is a medical condition that involves episodic spasm of the arteries that markedly reduces blood flow to the hands and/or feet that can eventually lead to poorly healing ulcers and to gangrene with loss of digits (FIG. 8). The episodes affecting the hands or feet initially turn white and later blue, often with associated numbness or pain. As the spasm ends with blood flow returning, the affected parts turn red and are typically painful. These episodes usually only last a few minutes, but can last for hours. There are two major types of Raynaud's Phenomenon that includes 4% of the population: primary without a known cause and secondary which occurs related to other primary conditions. The secondary conditions that can cause these episodes include immune disorders, such as, lupus and scleroderma, former trauma including frost bite, smoking, thyroid problems, and certain medications, such as, birth control pills. The existing primary treatment is to eliminate known stimulants, such as, smoking and to avoid exposing the affected extremities to cold temperatures. If these are not effective, then calcium channel blockers or a vasodilator can be tried. There currently are no other known remedies.

The patient that presented with scleroderma also suffered from Raynaud's phenomenon in both hands with sufficient frequency and intensity that multiple ulcers formed on the dorsum of several digits. The disclosed composition for treatment of Raynaud's Phenomenon was applied to the hands, between episodes of Raynaud's attacks, of the patient with scleroderma and improved the color of the fingers which also were found by palpation to be warmer.

Table 12 lists the composition formulation for treatment of Raynaud's Phenomenon.

Chemotherapy/Radiation Therapy Induced Oral Mucosal Lesions

Example 21

Figure 9:
FIG. 9 shows the ulcers Induced in Oral Mucosa by Chemotherapy/Radiation Therapy.

A common problem with both systemic irradiation and chemotherapy is the development of multiple induced oral mucosa! ulcers scattered throughout the mouth to the 40-60% patient incidence level (FIG. 9). These are very painful and have no known treatment at the moment. The pathophysiology of these ulcers relates to the fact that the oral mucosa! lining cells normally have a rapid turnover and replacement time. Whenever chemotherapy and/or radiation therapy in the body occurs, the turnover replication rate of these oral mucosa! lining cells reduces significantly. This means these cells cannot replicate sufficiently fast enough to replace their normal losses resulting in the formation of a mucosa with major gaps in their surface cell coverage.

Currently there is no treatment for this painful consequence of the tumor treatment. The significant factor one has to consider in developing a replacement is that the increased cell replication agent cannot interfere with the treatment of the tumor. This means that the treatment has to remain local within the mouth and cannot be absorbed into the body that is being treated for systemic cancers.

Table 13 lists the composition formulation for treatment of chemotherapy/radiation therapy induced oral mucosa! lesions.

TABLE 12

Raynaud's Phenomenon Composition Formulation

| Hydrophobic Components | amount | Hydrophilic Components | amount |
| --- | --- | --- | --- |
| a-Pinene (APN) | 60 ml | 1-Tetradecanol | 2.5 g |
| Acai Berry | 10 ml | AF (Artie Fish) Collagen (AFC) | 40 g |
| Argan Nut Oil (AGN) | 5 ml | *Agave* nectar (AGV) | 10 ml |
| Baobab Oil (BAB) | 5 ml | Alanine (ALA) | 5 g |
| Bees Wax (BW) | 40 g | *Aloe Vera* Leaf Gel (AVLG) | 275 g |
| Benzoin (BZN) | 4 ml | Arginine (ARG) | 5 g |
| Benzyl Alcohol (BA) | 50 ml | Distilled water | 500 ml |
| Caffeic acid | 5 g | Ferulic Acid (FRA) | 10 g |
| *Calendula* Oil (CDA) | 5 ml | Glutamine (GLU) | 5 g |
| *Camellia* Oil (CMA) | 10 ml | Glycine (GLY) | 5 g |
| Capaiba Oil (CPO) | 10 ml | Histidine (HST) | 5 g |
| Caprylic, Capric Triglyceride (CCT) | 10 ml | Hydroxyproline (HDP) | 5 g |
| Carvacrol (CVC) | 5 ml | Isoleucine (ISL) | 5 g |
| Cetyl Alcohol (CTA) | 40 g | Lecithin (LCT) | 25 g |
| Chamomile German Oil (CGB) | 10 ml | Leucine (LUC) | 5 g |
| Ghana Shea Butter (GSB) | 275 g | Linoleic Acid (LOA) | 5 ml |
| Glycerol (GLY) | 10 ml | Lysine (LYS) | 5 g |
| Kanuka Oil (KNO) | 2.5 ml | Methyl Sulfonyl Methane (MSM) | 25 g |
| Limonene Oil (LMN) | 40 ml | Niacinamide (NCM) | 2.5 g |
| *Litsea Cubeba* Oil (LCO) | 5 ml | Oleic Acid (OLA) | 5 ml |
| Black Cumin Seed Oil (BCS) | 50 ml | Praline (PRL) | 5 g |
| Panthenol (PNT) | 10 ml | Protocatechuic Acid (PCT) | 10 g |
| Terpineol | 5 ml | Sericin | 50 g |
| | | Sodium Polyacrylate | 20 g |
| | | Vitamin A (VTA) | 2.5 g |
| | | Vitamin B3 (VTB3) or Niacin | 12.5 g |
| | | Vitamin C (VTC) | 2.5 g |
| | | Vitamin E (VTE) | 2.5 g |

TABLE 13

Chemotherapy/Radiation Therapy Induced Oral Mucosal Lesions Composition Formulation

| Hydrophobic Components | amount | Hydrophilic Components | amount |
|---|---|---|---|
| a-Pinene (APN) | 60 ml | 1-Tetradecanol | 2.5 g |
| Acai Berry | 10 ml | AF (Artie Fish) Collagen (AFC) | 40 g |
| Anethole Anise Camphor | 5 ml | *Agave* nectar (AGV) | 10 ml |
| Argan Nut Oil (AGN) | 5 ml | Alanine (ALA) | 5 g |
| Baobab Oil (BAB) | 5 ml | *Aloe Vera* Leaf Gel (AVLG) | 275 g |
| Bees Wax (BW) | 40 g | Arginine (ARG) | 5 g |
| Benzoin (BZN) | 4 ml | Distilled water | 500 ml |
| Benzyl Alcohol (BA) | 50 ml | Ferulic Acid (FRA) | 10 g |
| Cabreuva Oil | 5 ml | Glutamine (GLU) | 5 g |
| *Calendula* Oil (CDA) | 5 ml | Glycine (GLY) | 5 g |
| *Camellia* Oil (CMA) | 10 ml | Histidine (HST) | 5 g |
| Capaiba Oil (CPO) | 10 ml | Hydroxyproline (HDP) | 5 g |
| Caprylic, Capric Triglyceride (CCT) | 10 ml | Isoleucine (ISL) | 5 g |
| Carvacrol (CVC) | 5 ml | Lecithin (LCT) | 25 g |
| Caryophyllene (CAP) | 10 ml | Leucine (LUC) | 5 g |
| Cedarwood essential Oil | 2.5 ml | Linoleic Acid (LOA) | 5 ml |
| Cetyl Alcohol (CTA) | 40 g | Lysine (LYS) | 5 g |
| Chamomile German Oil (CGB) | 10 ml | Methyl Sulfonyl Methane (MSM) | 25 g |
| Ghana Shea Butter (GSB) | 275 g | Niacinamide (NCM) | 2.5 g |
| Glycerol (GLY) | 10 ml | Oleic Acid (OLA) | 5 ml |
| Kaempferol | 5 g | Praline (PRL) | 5 g |
| Kanuka Oil (KNO) | 2.5 ml | Protocatechuic Acid (PCT) | 10 g |
| Limonene Oil (LMN) | 40 ml | Sericin | 50 g |
| *Litsea Cubeba* Oil (LCO) | 5 ml | Sodium Polyacrylate | 20 g |
| Niaouli Oil | 5 ml | Vitamin A (VTA) | 2.5 g |
| Black Cumin Seed Oil (BCS) | 50 ml | Vitamin B3 (VTB3) or Niacin | 12.5 g |
| Panthenol (PNT) | 10 ml | Vitamin C (VTC) | 2.5 g |
| Peppermint | 5 ml | Vitamin E (VTE) | 2.5 g |
| Sea Buckthorn Oil (SBO) | 5 ml | | |
| Thyme Red, White | 5 ml | | |
| Winter Savory | 5 ml | | |

Methods of Making Compositions

Example 22

The methods involved in producing these compositions are generally similar, but have different components for each composition. There are hydrophobic components and hydrophilic components that must be initially mixed separately under different temperature controls and then combined together properly. As many of these components are not liquid at room temperature, heating to phase change so they all become liquids is the first requirement. The first temperature level for the first mixture is set at 40° C. to 50° C., preferably 45° C., with a 300 to 500 rotations per minute (RPM), preferably 400 RPM, propeller mixing speed. All of the components that are a liquid or become a liquid at that temperature are mixed together in one of two vessels: a hydrophobic vessel and a hydrophilic vessel. The remaining unmixed components require higher temperatures to become liquid. Thus, the temperatures of the mixtures are increased to 60° C. to 80° C., preferably 60° C., and the speed of rotation is increased to 700 to 900 RPM, preferably 800 RPM. The remaining hydrophobic group components are added to its vessel and the hydrophilic group components are added to its vessel. After sufficient time of 1 to 8 hours, preferably more than 8 hours, for mixing and completion of reaction in each of the two vessels, the mixed hydrophilic group of components is then poured into the hydrophobic group vessel, maintaining the 700 to 900 RPM, preferably 800 RPM and the 60° C. to 80° C., preferably 60° C., temperature for another 10-40 minutes, preferably 20 minutes, of reaction time. At this point, the mixture is slowly cooled to room temperature over several hours of 2 to 10 hours while reducing the mixing speed to 500-700 RPM, preferably 600 RPM, continuing to insulate the mixing container. This lets the mixture cool to ambient room temperature of 25° C. to 37° C., preferably 25° C., over a slow period time while continuously being thoroughly mixed. When cooled to room temperature, the propeller is stopped and this final mixing vessel is removed to a surface top. This final composition will remain semisolid until it is returned to partial liquid at 37° C. by design to melt onto the skin when applied. Filling individual pumps (15 ml to 50 ml) is the final step prior to storage and then for delivery of this composition to the purchaser on a regular basis.

The information provided below is intended to compliment information provided above in this application.

The below definitions and discussion are intended to guide understanding but are not intended to be limiting with regard to other disclosures in this application. References to percentage (%) in compositions of the present invention refers to the % by weight of a given component to the total weight of the composition being discussed, also signified by "w/w", unless stated otherwise.

A "composition" of the present invention comprises alpha-pinene, an aloe vera preparation, a shea butter preparation, and other hydrophobic and hydrophilic components as discussed throughout the application, for instance in Tables 1-4 above and Tables I and II below. In an embodiment, a composition of the present invention is a topical composition, formulated to be applied topically to the skin. In other embodiments, a composition of the present invention may be formulated for and administered to a subject for instance by parenteral or enteral routes, injection, intravenous delivery, intramuscular, transdermal, intraperitoneal, or other routes of administration. In an embodiment, a composition of the present invention is formulated for oral delivery, for instance in a discrete solid dose unit, including for instance tablets, capsules, powders, liquids, chews, gummies, transdermals, injectables, dietary supplements, topical creams, lozenges, pills, and so forth. A composition of the present invention may further comprise one or more excipients, additives, and/or other substances.

In an embodiment, a composition of this invention is a water-in-oil emulsion. A water-in-oil emulsion of this invention further comprises water and an emulsifier. In an embodiment, water is distilled water, and comprises about 25-70% w/w of the emulsion and the composition. In an embodiment, water comprises about 25-50% w/w or about 50%-about 70% w/w of the emulsion. In an embodiment, an emulsifier that may be used in a water-in-oil emulsion of this invention is Tri-(polyglyceryl-3/Lauryl) Hydrogenated Trilinoleate (Cithrol PGTL); Polyglyceryl-3 Sorbityl Linseedate (Sinerga); Polyglyceryl-2 Oleate (and) Polyhydroxystearic Acid (and) Polyglyceryl-2 Stearate (Innovacos); Polyglyceryl-3 Triolivate (Acme Hardesty); Polyglyceryl-3 Polyricilinoleate (IOI Oleo); Polyglyceryl-2 Dipolyhydroxystearate (BASF); Polyglyceryl-2 Sesquiisostearate (Clariant); Polyglyceryl-3 Diisostearate (Gattefosse, BASF); Polyglyceryl-6 Polyricinoleate (and) Polyglyceryl-3 Diisostearate (and) Disteardimonium Hectorite (Elementis); Olive Oil Polyglyceryl-6 Esters (and) Polyglyceryl-6 Pentaoleate (Coast Southwest); Polyglyceryl-6 Polyricilinoleate (and) Polyglyceryl-10 Dioleate (Grant); Cetyl PEG/PPG-10/1 Dimethicone (Evonik); Methylglucose Sesquioleate (Lubrizol); and/or Octyldodecanol(and) octyldodecyl xyloside (and) PEG-30 dipolyhydroxystearate (Easynov). In an embodiment, a water-in-oil emulsion of the present invention comprises about 0.1-10.0% w/w of emulsifier; about 0.5% to 5% w/w emulsifier; about 1% to about 3% emulsifier w/w; in another embodiment; or about 1% to about 2% emulsifier w/w. In an embodiment, the water-in-oil composition is a topical composition.

In an embodiment, a composition of this invention may comprise, consist of, or consist essentially of components, ingredients, and/or other substances identified in this application as part of a composition, in any combination, including in particular those identified in Tables 1-4 above and Tables I-III below and emulsifiers identified in Example A. In an embodiment, said compositions comprise, consist of, or consist essentially of components and/or ingredients in percentages by weight of the composition as specified throughout the application or generally discussed in the antepenultimate paragraph of this application. Some exemplary compositions of the present invention are indicated below, as well as throughout the Tables and Examples of this application.

In an embodiment, a composition of the present invention comprises alpha-pinene, an aloe vera preparation, and a shea butter preparation.

In an embodiment, a composition of the present invention comprises alpha-pinene, an aloe vera preparation, a shea butter preparation, and an emulsifier.

In an embodiment, a composition of the present invention comprises alpha-pinene, an aloe vera preparation, a shea butter preparation, an emulsifier, and one or more functional oils.

In an embodiment, a composition of the present invention comprises alpha-pinene, an aloe vera preparation, a shea butter preparation, an emulsifier, soluble collagen, and one or more of the following functional oils: Black Cumin Seed Oil, Baobab Oil, Apricot Kernal Oil, Argan Nut Oil, *Camellia* Oil, Marula Oil, Sea Buckthorn Oil, Tamanu Oil, Calendula Oil, caprylic/capric triglyceride, caryophyllene, Elemi Oil, Kanuka Oil, Litsea Cubebe Oil, Palmarosa Oil, Palo Santo, Rose Hip Seed Oil, and Sachi Inchi Oil.

In an embodiment, a composition of the present invention comprises alpha-pinene, an aloe vera preparation, a shea butter preparation, an emulsifier, soluble collagen, and Black Cumin Seed Oil.

In an embodiment, a composition of the present invention comprises alpha-pinene, an aloe vera preparation, a shea butter preparation, an emulsifier, and one or more soluble collagens.

In an embodiment, a composition of the present invention comprises alpha-pinene, an aloe vera preparation, a shea butter preparation, an emulsifier, and one or more alcohols.

In an embodiment, a composition of the present invention comprises alpha-pinene, an aloe vera preparation, a shea butter preparation, an emulsifier, and one or more anti-inflammatories.

In an embodiment, a composition of the present invention comprises alpha-pinene, an aloe vera preparation, a shea butter preparation, an emulsifier, soluble collagen, one or more functional oils, caryophyllene, caprylic/capric triglyceride, and one or more of the following anti-inflammatories: chamomile oil, copaiba oil, oleic acid, and linoleic acid.

In an embodiment, a composition of the present invention comprises alpha-pinene, an aloe vera preparation, a shea butter preparation, an emulsifier, and one or more anti-oxidants.

In an embodiment, a composition of the present invention comprises alpha-pinene, an aloe vera preparation, a shea butter preparation, an emulsifier, soluble collagen, one or more functional oils, caryophyllene, caprylic/capric triglyceride, ferulic acid, one or more anti-inflammatories, and one or more of the following anti-oxidants: tocopherol, tocopheryl acetate, retinyl palmitate, and tetrahexyldecyl ascorbate.

In an embodiment, a composition of the present invention comprises alpha-pinene, an aloe vera preparation, a shea butter preparation, an emulsifier, and one or more anti-microbials.

In an embodiment, a composition of the present invention comprises alpha-pinene, an aloe vera preparation, a shea butter preparation, an emulsifier, soluble collagen, one or more functional oils, caryophyllene, caprylic/capric triglyceride, ferulic acid, one or more anti-inflammatories, one or more anti-oxidants, and one or more of the following anti-microbials: carvacrol, niacinamide, and one or more amino acids.

In an embodiment, a composition of the present invention comprises alpha-pinene, an aloe vera preparation, a shea butter preparation, an emulsifier, and one or more florals.

In an embodiment, a composition of the present invention comprises alpha-pinene, an aloe vera preparation, a shea butter preparation, an emulsifier, and one or more thickeners.

In an embodiment, a composition of the present invention comprises alpha-pinene, an aloe vera preparation, a shea butter preparation, an emulsifier, and one or more waxes.

In an embodiment, a composition of the present invention comprises alpha-pinene, an aloe vera preparation, a shea butter preparation, an emulsifier, and one or more fragrances.

In an embodiment, a composition of the present invention comprises alpha-pinene, an aloe vera preparation, a shea butter preparation, an emulsifier, and one or more fatty acids.

In an embodiment, a composition of the present invention comprises alpha-pinene, an aloe vera preparation, a shea butter preparation, an emulsifier, and one or more analgesics.

In an embodiment, a composition of the present invention comprises alpha-pinene, an aloe vera preparation, a shea butter preparation, an emulsifier, and one or more amino acids.

In an embodiment, a composition of the present invention comprises alpha-pinene, an aloe vera preparation, a shea butter preparation, an emulsifier, and one or more carbohydrates.

In an embodiment, a composition of the present invention comprises alpha-pinene, an aloe vera preparation, a shea butter preparation, an emulsifier, and one or more vitamins.

In an embodiment, a composition of the present invention comprises alpha-pinene, an aloe vera preparation, a shea butter preparation, an emulsifier, and one or more solvents.

In an embodiment, a composition of the present invention comprises alpha-pinene, an aloe vera preparation, a shea butter preparation, an emulsifier, and one or more gels.

In an embodiment, a composition of the present invention comprises alpha-pinene, an aloe vera preparation, a shea butter preparation, an emulsifier, and one or more moisturizers.

In an embodiment, a composition of the present invention comprises alpha-pinene, an aloe vera preparation, a shea butter preparation, an emulsifier, and one or more additional components selected from the group consisting of functional oils, soluble collagens, alcohols, anti-inflammatories, anti-oxidants, anti-microbials, florals, thickeners, waxes, fragrances, fatty acids, analgesics, amino acids, carbohydrates, vitamins, solvents, gels, and moisturizers.

In an embodiment, a composition of the present invention comprises alpha-pinene, an aloe vera preparation, a shea butter preparation, an emulsifier, soluble collagen, one or more functional oils, caryophyllene, caprylic/capric triglyceride, ferulic acid, methyl sulfonyl methane, magnesium sulfate, propylene glycol, one or more anti-inflammatories, one or more anti-oxidants, and one or more anti-microbials.

In an embodiment, a composition of the present invention comprises alpha-pinene, an aloe vera preparation, a shea butter preparation, an emulsifier, soluble collagen, one or more functional oils, caryophyllene, caprylic/capric triglyceride, ferulic acid, methyl sulfonyl methane, magnesium sulfate, propylene glycol, betaine, sodium PCA, sodium lactate, PCA, 1,2-hexane diol, caprylyl glycol, one or more anti-inflammatories, one or more anti-oxidants, and one or more anti-microbials.

In an embodiment, a composition of the present invention comprises alpha-pinene, an aloe vera preparation, a shea butter preparation, Tri-(polyglyceryl-3/Lauryl) Hydrogenated Trilinoleate, soluble collagen, one or more functional oils, caryophyllene, caprylic/capric triglyceride, ferulic acid, methyl sulfonyl methane, magnesium sulfate, propylene glycol, betaine, sodium PCA, sodium lactate, PCT, 1,2-hexane diol, caprylyl glycol, one or more anti-inflammatories, one or more anti-oxidants, and one or more anti-microbials.

While the following substances may be included in a composition of the present invention, in an embodiment, a composition of this invention does not comprise a drug of addiction in pharmacologically significant amounts, beta-pinene added individually or as a substantial component of a natural product, a propellant such as for a mousse or spray, and/or trans-tert-butyl-cyclohexanol. In an embodiment, compositions of the present invention are not formulated as a sunblock, not formulated to complement other specific compounds or families of compounds other than those identified in the present application, not formulated to prevent diaper rash or provide a barrier on the skin to protect from urine and feces, and/or are not formulated as an additive to other compositions. In an embodiment, a composition of the present invention requires water, and is not anhydrous. In an embodiment, a composition of the present invention may include any or all of the above.

In the present invention, an "effective amount" of a composition refers to an amount of alpha-pinene, an aloe preparation, a shea butter preparation, and other components and/or ingredients of a composition of the present invention needed to be administered to a subject, for instance enough composition to be topically applied to the skin, in an area of the skin for treatment or alleviation, and if necessary for treatment or alleviaton to reach a subject's bloodstream and/or bodily tissues and thereby improve the condition to be treated or alleviated, such as Dupuytren's disease and/or contracture and others as discussed throughout this application. In an embodiment, a composition of the present invention is formulated to include an effective amount to treat one or more of the conditions described throughout this application. Percentages by weight of at least alpha-pinene, an aloe preparation, a shea butter preparation, along with other components and/or ingredients described throughout this application, in a composition of the present invention, provide an effective amount of these substances, when the composition is topically applied to the affected area in sufficient volume.

In an embodiment, the present invention is directed to a method of treatment or alleviation of Dupuytren's Disease and Contracture; Abrasions, Cuts, and Minor Burns; Peyronie's Disease or Induratio Penis Plastica; Aging Skin; Nail Fungus; Aphthous Ulcers; Cutaneous Involvement of Scleroderma; Raynaud's Phenomenon; Chemotherapy/Radiation Therapy Induced Oral Mucosal Lesions; Plantar Fasciitis; Arthritis; Sun Burn; and/or Baldness. The method comprises the step of applying a composition of the present invention to an area affected by the above diseases or wounds. In addition, the present invention is directed to a method of promoting Wound Healing, for instance by decreasing time for a wound to heal, and a method of promoting hair growth on the arms, legs, and scalp.

For the treatment or alleviation of Dupuytren's disease and contracture, the improvement provided by the topical application of a composition such as described in Table 5 to an affected area such as the hands is described as in Examples 1-4, above, for instance with a decrease in nodule size or contracture of the hands. Similarly, in an embodiment, large-scale composition described in Example A treats or alleviates Dupuytren's disease when topically applied over the affected area, for instance by decreasing nodule size and/or contracture. For instance as discussed in Example A, in an embodiment 15-30 ml of the composition of Table III prepared according to the process of Example A was applied to the hands of an adult male suffering from Dupuytren's Disease and Contracture. The topical application, twice daily, reduced symptoms including contracture symptoms prevented progression of the disease for a period of several months, as of the date of filing this application.

For the treatment of Abrasions, Cuts, and Minor Burns, the improvement provided by the topical application of a composition of the present invention to an abrasion, cut, and/or minor burn, such as described in Table 6 and Examples 5-8 above. In another embodiment, compositions of the present invention improve Wound Healing (that is, healing of abrasions, cuts, and/or minor burns). Similarly, in an embodiment, the large-scale composition described in Example A provides Wound Healing properties and treats abrasions, cuts, and minor burns according to the present invention.

For the treatment of Peyronie's Disease or Induratio Penis Plastica, improvements by the topical application of a composition of the present invention to the penis, such as described in Table 7 and Examples 9-11 above, including for instance a reduction in curvature of the penis and ability of the subject to resume/participate in intercourse. Similarly, in an embodiment, the large-scale composition described in Example A treats Peyronie's Disease or Induratio Penis Plastica when applied to the penis of a subject suffering from the condition.

For the treatment of the condition of Aging Skin, improvement by the topical application of a composition of the present invention to aging skin, such as described in Table 8 and Examples 12-13 above. Similarly, in an embodiment, the large-scale composition described in Example A treats Aging Skin for instance by improving its thickness and ability to grow hair.

For the treatment of Nail Fungus such as Toe Nail Fungus, the improvement by the topical application of a composition of the present invention to the area afflicted with fungus, such as described in Table 9 and Examples 14-16 above, is elimination or reduction of the fungal infection. Similarly, in an embodiment, the topical application of the large-scale composition described in Example A treats Nail Fungus such as Toe Nail Fungus.

For the treatment of Aphthous Ulcers, the improvement by the topical application of a composition of the present invention to the aphthous ulcer, such as described in Table 10 and Examples 17-18 above, reduces the duration and/or relieves pain from the ulcer. Similarly, in an embodiment, the topical application of the large-scale composition described in Example A treats Aphthous Ulcers.

For the treatment of Cutaneous Involvement of Scleroderma, the improvement by the topical application a composition of the present invention to a skin lesion from scleroderma, as discussed in Table 11 and Example 19 above, relieves discomfort and other symptoms. Similarly, in an embodiment, the large-scale composition described in Example A treats skin lesions associated with Scleroderma.

For the treatment of Raynaud's Phenomenon, the improvement by the topical application of a composition of the present invention to affected areas such as fingers and toes, such as described in Table 12 and Example 20 above, includes for instance improving the color and or warmth of the subject's digits. Similarly, in an embodiment, the large-scale composition described in Example A treats Raynaud's Phenomenon.

For the treatment of Chemotherapy/Radiation Therapy Induced Oral Mucosal Lesions, the improvement by the topical application of a composition of the present invention to said lesions, such as described in Table 13 and Example 21 above, includes reducing the size of the lesion and/or associated pain. Similarly, in an embodiment, the large-scale composition described in Example A treats Oral Mucosal Lesions induced by Chemotherapy/Radiation Therapy.

Other conditions may be treated by the topical application of a composition of the present invention to the affected area, such as the large-scale composition described in Table III and Example A, and other compositions described throughout this application, including those described in Tables 5-13.

In an embodiment, Plantar Fasciitis is treated by the topical application of a composition of the present invention to the heels and surrounding areas of the feet, such as the large-scale composition described in Example A, and other compositions described throughout this application. Treatment of Plantar Fasciitis according to the present invention relieves inflammation and/or pain in the heels and feet of the subject.

In an embodiment, Arthritis may be treated by the topical application of a composition of the present invention to a joint of the body such as a knee, elbow, hands, or other area affected by arthritis, such as the large-scale composition described in Example A and Table III, and other compositions described throughout this application. Treatment of Arthritis according to the present invention relieves pain and inflammation in the joints.

In an embodiment, Sun Burn of the skin may be treated or alleviated by the topical application of a composition of the present invention to a sun burned area, such as the large-scale composition described in Example A, and other compositions described throughout this application. Treatment or alleviation of Sun Burn of the skin according to the present invention relieves redness and/or pain on the affected area.

In an embodiment, unwanted Baldness may be treated by the topical application of a composition of the present invention to an area of the scalp where hair growth is desired, such as the large-scale composition described in Example A, and other compositions described throughout this application. Treatment of Baldness of the scalp according to the present invention increases hair growth on the scalp.

In an embodiment, a composition of the present invention is prepared by a process of the present invention. In an embodiment, a composition of the present invention may be used for the treatment of one or more of the conditions identified above. In an embodiment, the present invention is directed to the use of a composition of the present invention for the preparation of a medicament to treat one of the above conditions.

Additional Components: Tables I and II

Tables I and II summarize ingredients that may be included in a composition of the present invention, in addition to those discussed elsewhere and throughout this application. Indications of functions are intended as descriptive of an embodiment of the invention and not limiting, and are not meant to bind the present invention by theory. In an embodiment, a component of a composition of this invention may provide one, and/or more than one, function in the composition. The below Tables are intended to add to Tables 1-4, above, and to be understood in that context. In an embodiment, optional components of the present invention such as those listed below are individually less than 10% of a composition of this invention (w/w); less than 5% of a composition of this invention (w/w); less than 3%, less than 2%, less than 1%, or less than 0.5% w/w of a composition of this invention (w/w). Taken together, for instance as described throughout this application, the ingredients identified allow for variation in formulation while retaining usefulness such as described in this application.

TABLE I

| Hydrophobic Component | Function | Scientific Name/ Formula | Component % of Composition (w/w) |
|---|---|---|---|
| Acai Berry Oil | Anti-inflammatory, Skin Moisturizer | *Euterpe oleracea* | 0.00 to 50.00% |
| Ajwain Oil | Anti-microbial, anti-inflammatory | *Trachyspermum ammi* herb | 0.00 to 50.00% |
| Almond Oil | Emulsifier, Emollient | *Prunus dulcis* tree | 0.00 to 50.00% |
| Galbanum Oil, Greater Galangal | Anti-inflammatory | *Alpinia galangal* | 0.00 to 50.00% |
| Lesser Galangal | Anti-Microbial | *Alpinia officinarum* | 0.00 to 50.00% |
| Norwegian *Angelica* Oil | Anti-inflammatory, Anti-Microbial | *Angelica archangelica* tree | 0.00 to 50.00% |
| Anise Seed Oil | Micro-Emulsion, Anti-Microbial | *Pimpinella anisum* | 0.00 to 50.00% |
| Anethole Oil | Micro-Emulsion, Anti-Microbial | turpentine-like tree extracts | 0.00 to 50.00% |
| Annato | Anti-Inflammatory, Anti-Oxidant, Colorant | *B. orellana* | 0.00 to 50.00% |
| Arachidonic Acid | Anti-Inflammatory, Vasodilator | $C_{20}H_{32}O_2$ | 0.00 to 50.00% |
| Atlas Cedar Wood Oil | Anti-Oxygen Radical, Anti-Microbial | *Cedarus atlantica* | 0.00 to 50.00% |
| Carnauba Wax | Hypoallergenic, Emollient, Cross-Linker | *Copernica cerifera* | 0.00 to 50.00% |
| Bayberry Wax | Fragrance, Cross-Linker | complex; CAS 8038-77-5; mp 45° C. | 0.00 to 50.00% |
| Bixin | Pigment, Dye | $C_{25}H_{30}O_6$ | 0.00 to 50.00% |
| *Boesenbergia rotunda* | Anti-Microbial | *Boesenbergia rotunda* | 0.00 to 50.00% |
| Cajuput or Cajeput Oil | Fragrance, Anti-inflammatory | *Melaeuca Leucadendron* | 0.00 to 50.00% |
| Canolol Oil | Anti-Oxidant | $C_{10}H_{12}O_3$ | 0.00 to 50.00% |
| *Cassia* Oil | Fragrance | *Cinnamomum cassia* | 0.00 to 50.00% |
| Cedar Oil | Anti-Microbial, Fragrance | *Cedrus atlantica* | 0.00 to 50.00% |
| Cichoric Acid | Anti-Hyaluronidase, Anti-Collagenase | $C_{22}H_{18}O_{12}$; {2R,3R}-2,3-bis[[(E)-3-(3,4-dihydroxyphenyl)prop-2-enoyl]oxy] butanedioic acid | 0.00 to 50.00% |
| Chlorogenic Acid | Anti-Oxidant | $C_{16}H_{18}O_9$ | 0.00 to 50.00% |
| Chlorophyll Oil | Colorant, Pigment | CAS 1406-65-1 | 0.00 to 50.00% |
| Coumaric Acid | Anti-Oxidant, Anti-inflammatory | $C_9H_8O_3$ | 0.00 to 50.00% |
| CoEnzyme Q10 | Anti-Oxidant | $C_{59}H_{90}O_4$ | 0.00 to 50.00% |
| Copaiba Oil | Anti-inflammatory | *Copaifera langsdorff* | 0.00 to 50.00% |
| Costmary Oil | Anti-Microbial | *Tanacetum balsamita* herb | 0.00 to 50.00% |
| Cubeb Oil | Fragrance | *Piper cubeba* | 0.00 to 50.00% |
| Curcumin | Anti-oxidant, Fragrance | I$C_{21}H_{20}O_6$, $C_{21}H_{20}O_6$ | 0.00 to 50.00% |
| Davana Oil | Fragrance | *Artemisia pallens* | 0.00 to 50.00% |
| Emu Oil | Micro-Emulsion, High Oleic Acid content | *Dromaius novahollandiae* bird | 0.00 to 50.00% |
| Ethyl Cinnamate Oil | Fragrance, Anti-Microbial | *Cinnamomum verum* | 0.00 to 50.00% |
| Eucalyptol Oil | Anti-Inflammatory, Fragrance | *Eucalyptus obliqua* | 0.00 to 50.00% |
| Frankincense Oil | Fragrance | *Boswellia carteri* | 0.00 to 50.00% |
| Galangin | Anti-Microbial, flavonol from Lesser Galangal | $C_{15}H_{10}O_5$ | 0.00 to 50.00% |
| Ginger Oil | Fragrance | *Zingiber officianale* | 0.00 to 50.00% |
| *Helichrysum* Oil | Anti-Oxidant | *Helichrysum orientale* | 0.00 to 50.00% |
| Jojoba Oil | Cosmetic | *Simmomdsia chinensis* | 0.00 to 50.00% |
| *Kaempferia* Oil | Anti-Microbial, Fragrance | *Kaempferia galangal* | 0.00 to 50.00% |
| Lauryl Wax | Surfactant, Anti-Microbial | Complex | 0.00 to 50.00% |
| Lavender Oil | Anti-Oxidant, Anti-Inflammatory | *Lavandula augustifolia* plants | 0.00 to 50.00% |
| Lemon Oil | Fragrance, Phytochemical | *Citrus lemon* | 0.00 to 50.00% |

TABLE I-continued

| Hydrophobic Component | Function | Scientific Name/ Formula | Component % of Composition (w/w) |
|---|---|---|---|
| Linalool | Fragrance, Chemical Intermediate, Insect Repellent | $C_{10}H_{18}O$; CAS 78-70-6 | 0.00 to 50.00% |
| *Magnolia* Oil | Anti-Inflammatory, Phytochemical | *Magnolia grandiflora* | 0.00 to 50.00% |
| *Moringa* Oil | Anti-Oxidant, Anti-Inflammatory | *Moringa oleifera* | 0.00 to 50.00% |
| Myristic Acid | Fragrance, Flavor, Plastics, Paper | $C_{14}H_{28}O_2$; 1-tetradecanoic acid | 0.00 to 50.00% |
| Myrrh Oil | Anti-Microbial, Fragrance | *Commiphora myrrha* tree | 0.00 to 50.00% |
| Neroli Oil | Fragrance, Cosmeceutical | *Citrus aurantium amara* tree - Lemon tree leaves and twigs | 0.00 to 50.00% |
| Niola Oil | Anti-Inflammatory, Anti-Microbial | *Citrus aurantium-amara*; Lemons | 0.00 to 50.00% |
| Oregano Oil | Anti-Oxidant, Anti-Inflammatory, Anti-Microbial | *Origanum vulgare* | 0.00 to 50.00% |
| Oleanolic Acid | Anti-Tumor, Anti-Viral, Anti-Inflammatory | $C_{30}H_{48}O_3$ | 0.00 to 50.00% |
| Orris Oil | Anti-Inflammatory, Anti-Microbial | *Iris germatica* | 0.00 to 50.00% |
| Paprika Oleoresin | Fragrance, Color | Capsanthin; $C_{40}H_{53}O_3$ | 0.00 to 50.00% |
| Patchouli Oil | Fragrance, Anti-Insect | *Pogostemon cabalin* plant | 0.00 to 50.00% |
| Peppermint Oil | Flavor, Anti-Septic, Anti-Insect | *Mentha piperota* | 0.00 to 50.00% |
| *Perilla* Seed Oil | Omega-3-Fatty Acid, Industrial | Kkaennip-deulgireum | 0.00 to 50.00% |
| Petitgrain Oil | Fragrance | *Citrus autantium amara* | 0.00 to 50.00% |
| Phellandrene | Fragrance | Cyclohexadiene $C_{10}H_{16}$ | 0.00 to 50.00% |
| Pine Oil | Disinfectant | *Pinus sylvestris* tree | 0.00 to 50.00% |
| *Ravensara* Oil | Anti-Microbial | *Ravensara aromatica* | 0.00 to 50.00% |
| Resinoid Oil | Fragrance | Benzoin: $C_{14}H_{12}O_2$ | 0.00 to 50.00% |
| Rose Hip Seed Oil | Pytonutrients, Essential Fatty Acids | *Rosa moschata* and/or *Rosa rubiginosa* | 0.00 to 50.00% |
| Rosemary Oil | Fragrance, Phytonutrients | *Salvia rosmarinus* | 0.00 to 50.00% |
| Sabinene | Flavor, Plant Stimulant | $C_{10}H_6$ | 0.00 to 50.00% |
| Soy Wax | Coating, Thickener | Hydrogenated Soy Oil | 0.00 to 50.00% |
| Spearmint Oil | Flavor | *Mentha viridis* | 0.00 to 50.00% |
| Terpinene Oil | Anti-Oxidant, Fragrance | $C_{10}H_{16}$ | 0.00 to 50.00% |
| Terpineol Alcohol | Anti-Microbial, Anti-Inflammatory, Anti-Oxidant | $C_{10}H_{18}O$ | 0.00 to 50.00% |
| Thyme Oil | Anti-Inflammatory | *Thymus vulgaris* | 0.00 to 50.00% |
| Thyme Red Oil | Diffusion Mists | *Thymus citriodorus* | 0.00 to 50.00% |
| Thyme White Oil | Anti-Microbial | *Thymus citriodorus* | 0.00 to 50.00% |
| Thymoquinone | Anti-Oxidant, Anti-Inflammatory | From Black Seed Oil | 0.00 to 50.00% |
| Thymohydroquinone Methyl Ether | Anti-Oxidant, Anti-Inflammatory | 2,5-Dimethoxy-p-cymene | 0.00 to 50.00% |
| Tri(Polyglyceryl-3/Lauryl) Hydrogenated Trilinoleate | Emulsifier | Cithrol PGTL | 0.00 to 10.00% |
| Turmeric Oil (Curcumin) | Anti-Oxidant, Anti-Inflammatory | *Curcuma longa* | 0.00 to 50.00% |
| Ursolic Acid | Anti-Mutagenic, Anti-Inflammatory | $C_{30}H_{48}O_3$ | 0.00 to 50.00% |

TABLE II

| Hydrophilic Component | Function | Scientific Name/ Formula | Component % of Composition (w/w) |
|---|---|---|---|
| Benzoic Acid | Anti-Microbial, Anti-Oxidant, Moisturizer | $C_7H_6O_2$ CAS 115-95-7 | 0.00 to 50.00% |
| Betaine | Rx for homocystinuria | Trimethyl glycine | 0.00 to 50.00% |

TABLE II-continued

| Hydrophilic Component | Function | Scientific Name/ Formula | Component % of Composition (w/w) |
|---|---|---|---|
| Berberine | Anti-Oxidant, Anti-Lipemic Drug, Anti-Fungal Drug | $C_{20}H_{18}NO_4^+$ CAS 2086-83-1 | 0.00 to 50.00% |
| Alpha-Cadinol | Anti-Fungal, Hepato-Protective | $C_{15}H_{16}O$ CAS 41-34-5 | 0.00 to 50.00% |
| Caramel powder | Anti-Oxidant | Confectionary Product of Sugars | 0.00 to 50.00% |
| Capric (Decanoic) Acid | Anti-Fungal, Anti-Convulsant | coconut oil and palm kernel oil | 0.00 to 50.00% |
| Dexapanthenol | Emollient | $C_9H_{19}NO_4$ CAS 81-13-0 | 0.00 to 50.00% |
| Glutamic Acid | Nutraceutical, Neurotransmitter | L- Glutamic Acid | 0.00 to 50.00% |
| 1,2-Hexanediol | Cosmetic Use - Eye, Face, Lipstick | $C_6H_{14}O_2$ | 0.00 to 50.00% |
| Hyaluronic Acid | Skin Wound Repair, Orthopedic Joint Injections | $(C_{14}H_{21}NO_4)_n$ | 0.00 to 50.00% |
| Isopropyl myristate | Emollient, Solvent | $C_{17}H_{34}O_2$ | 0.00 to 50.00% |
| Linalyl Acetate | Oil | $C_{12}H_{20}O_2$ CAS 115-95-7 | 0.00 to 50.00% |
| Lidocaine | Local Anesthetic | $C_{14}H_{22}N_2O$ CAS 137-58-6 | 0.00 to 50.00% |
| Magnesium Sulfate | Epsom Salt, Bronchial Dilator, Anti-Inflammatory | $MgSO_4$ | 0.00 to 50.00% |
| 1,2-Octanediol (Caprylyl glycol) | Head Lice Treatment, Anti-Microbial | $C_8H_{18}O_2$ | 0.00 to 50.00% |
| Octanoic (Caprylic) Acid | Anti-Microbial, Ghrelin-Induced Stimuli | coconut oil and palm kernel oil | 0.00 to 50.00% |
| A Phycobiliprotein | Phycobiliprotein Absorption @ 621 nm | Phycocyanin | 0.00 to 50.00% |
| Propylene Glycol | Pharmaceutical Solvent, Polymer Production, Cosmetic Solvent | $CH_3CHCH_2OH$ | 0.00 to 50.00% |
| Purple Carrot Juice | Anthocyanin Color, Anti-Oxidant | *Dancus carota sativus* | 0.00 to 50.00% |
| Protocatechuic Acid (PCA; DihydroxyBenzoic Acid) | Anti-Oxidant, Anti-Inflammatory; Humectant in skin and hair products | DL-Pyrrolidone-carboxylic acid; polyglutamic acid; pidolic acid; CAS 98-79-3 | 0.00 to 50.00% |
| Red Beet Juice | Betanin pigment | *Beta vulgaris* | 0.00 to 50.00% |
| Serine | Amino Acid | $C_3H_3NO_3$ | 0.00 to 50.00% |
| Sodium Hyaluronate (Na salt of Hyaluronic Acid) | Tissue Lubricant | $C_{28}H_{44}N_2NaO_{23}$; commercially available in Etamucine, Luronit, Biolon, Amvisc | 0.00 to 50.00% |
| Sodium Hydroxide | pH adjuster, basic | NaOH | 0.00 to 50.00% |
| Sodium Lactate | Humectant, Moisturizer | $NaC_3H_5O_3$ | 0.00 to 50.00% |
| Sodium Protocatechuic Acid (Sodium PCA; Na Salt of Protocatechuic Acid) | Anti-Oxidant, Anti-Inflammatory; Humectant | Sodium L-Pyrrolidonecarboxylate | 0.00 to 50.00% |
| Sulisobenzone | UV B and UV A protective sunscreen | $C_{14}H_{12}O_6S$; Benzophenone-4; 5-Benzoyl-4-hydroxy-2-methoxybenzenesulfonic acid | 0.00 to 50.00% |
| Threonine | Amino Acid | L-Threonine | 0.00 to 50.00% |

Components/Ingredients Used in the Large-Scale Process and Composition of Example A Aloe Vera/*Aloe Barbadensis* Miller Preparations An "aloe vera preparation" of the present invention is prepared or otherwise derived from leaves of the aloe vera plant, otherwise known as *Aloe barbadensis* mil. In an embodiment, an aloe vera preparation is a hydrophilic component of a composition of the present invention. In an embodiment, an aloe vera preparation is and/or includes gel taken from the inner portion of aloe vera leaves (also known as "aloe vera inner leaf gel"), for instance as described above. Aloe vera inner leaf gel is a gel that contains proteins, lipids, amino acids, vitamins, enzymes, inorganic compounds, organic compounds, and carbohydrates. The gel may be in its natural form, taken directly from the aloe vera leaf, or for instance in a processed form, for instance as a 10× or 200× concentrated dried powder. In an embodiment, an aloe vera preparation of this invention may include part of or all of whole aloe vera leaves, for instance in the form of aloe vera leaf juice or an aloe vera leaf extract. An aloe vera preparation that is or includes leaf juice or is or includes leaf extract may also be in a concentrated form, for instance in a 10× or 200× dried powder. In an embodiment, an aloe vera preparation of the present invention does not include the aloin or yellow or brown latex portion of the aloe leaf, and/or does not include the dark green outer covering of the leaf In an embodiment, the aloe vera inner leaf gel is in powder form, 200× concentrated. For instance, the 200× powder may be a spray-dried, light-cream-to-beige colored powder, having characteristics such as pH(1:199 w/w) 3.5-5.0, specific gravity(1:199 w/w) 0.997-1.004, 8% maximum moisture, 100% particle size through 80 mesh, certifications such as is made from pure aloe i.e. does not include fillers and/or adulterants, and/or has no pathogens present (<10 cfu/g total plate count, <10 cfu/g yeast and mold). In an embodiment, the 200× aloe vera inner leaf gel powder is spray-dried to 200× the concentration of aloe vera inner leaf gel, is light cream to beige powder, pH 4.5, specific gravity (1:199 w/w) 1.001, about 4-5% moisture (water), 100% particle size through 80 mesh, is pure aloe i.e. does not include fillers and/or adulterants, and has no pathogens present (<10 cfu/g total plate count, <10 cfu/g yeast and mold). In a preferred embodiment, the aloe vera preparation is Terra-Pure™ Certified Spray Dried Aloe Vera Inner Leaf Powder Regular, 200× (Terry Laboratories, Melbourne Fla., USA). In an embodiment, an aloe vera preparation including a 200× aloe vera preparation comprises or consists of inner leaf juice, made by removing the rind of the leaf prior to processing and then rinsing away aloe latex. The remaining, gelatinous inner-leaf material is then ground/crushed into aloe vera inner leaf juice.

In an embodiment, aloe vera according to the present invention includes other parts of the aloe vera plant. For instance, the aloe vera preparation may be a powder made from *Aloe barbadensis* leaf juice (e.g. CAS 94349-62-9). In an embodiment, leaf juice is extracted from fresh aloe leaves with a juice extractor, decolorized and filtered, separated via organic membrane. The membrane-separated concentrate juice is then freeze dried to be converted into the 200:1 Aloe Vera freeze dried gel powder. In an embodiment, an aloe vera preparation according to the present invention is Aloe Vera freeze dried gel powder 200:1 (Selco, Wald-Michelbach, Germany). In an embodiment, 200:1 aloe powder includes about 0.5% soluble solid of Aloe Vera gel. 200 kg of 1:1 Aloe Vera gel juice is frozen and dried into 1 kg of Aloe Vera freeze dried gel powder that becomes Aloe vera 200:1.

In an embodiment, aloe vera according to the present invention is a 200× powder produced through the water extraction of *Aloe barbadensis* leaf to prepare leaf juice powder. In an embodiment, aloe leaves are harvested, washed and fileted, aloin removed from filets, then the leaves ground, excess pulp removed, treated with heat, filtered, and spray dried. Aloe vera according to the present invention, in unconcentrated or concentrated (e.g. 200×) form, is a hydrophilic component/ingredient of this invention. While 200× concentrated powders are a preferred embodiment according to the present invention, other concentrations may also be included in the present invention.

In an embodiment, aloe vera preparations of the present invention, for instance provided by Terry Laboratories as described above, include aloe polysaccharides consisting of linear (unbranched) chains of b-1-4-linked glucose and mannose molecules (often called glucomannans, and because more mannose than glucose is present, polymannans). These linear chains range from a few molecules to several thousand molecules. By convention, the lower limit is usually taken as a molecular weight of about 1,000 Daltons for the material to qualify as a polysaccharide. In an embodiment, aloe vera preparations for instance as provided by Terry Laboratories are microbiologically clean, color stable, processed as quickly as possible following harvest, and processed at the lower temperature possible. Also, in an embodiment the aloe vera preparation including for instance 10× or 200× aloe vera preparations retains polysaccharide molecular weight distribution comparable to unprocessed aloe vera and reduces polysaccharide degradation such that not less than 50% of polysaccharides are greater than 1 million Daltons. In an embodiment, an aloe vera preparation includes acemannan (beta-1-4-acetylated glucomannans).

In an embodiment, in keeping with for instance Table 2 above, a composition according to the present invention may include 0.1-50% aloe vera gel. In a preferred embodiment, a composition according to the present invention includes about 5% to about 30% w/w of an aloe vera preparation; about 10% to about 20% w/w; about 13% to about 18% w/w; about 14 to about 16% w/w; or about 15% w/w, as shown in Tables 5-13 above and in Table III below. In an embodiment, the aloe vera preparation may be in a natural, 1×, single-strength equivalent form, or in a concentrated 10×, 200×, or other concentrated form, as discussed above and shown in the Examples.

Alpha-Pinene

In an embodiment, alpha-pinene may be included in a composition of the present invention. In an embodiment, alpha-pinene is provided as a colorless liquid with a pine, turpentine-like odor. In an embodiment, alpha-pinene is from a natural source. In an embodiment, alpha-pinene is from a synthetic source. In an embodiment, alpha-pinene has a specific gravity (25° C.) of 0.8550-0.8600, a refractive index (20° C.) of 1.4640-1.4680, optical rotation 20.00-30.00, and/or is provided with no *salmonella* (AOAC, negative), lead, aflatoxin, arsenic, or mercury detected. The alpha-pinene may weigh about 7 pounds per gallon. In an embodiment, alpha-pinene is 95-100% pure, preferably 99-100% pure. In an embodiment, pure alpha-pinene is obtained from Flavorchem Orchidia Fragrances, Downers Grove, Ill., USA.

As indicated for instance in Table 1 above, alpha-pinene is a hydrophobic component of this invention. As also disclosed for instance in Table 2 above, a composition according to the present invention may include 0.1-50% alpha-pinene. In a preferred embodiment, a composition according to the present invention includes about 0.5% to about 20% w/w alpha-pinene; about 1% to about 10% w/w alpha-pinene; about 2% to about 7% w/w alpha-pinene; or about 3 to about 4% w/w alpha-pinene, for instance as shown in Tables 5-13 above and in Table III below.

Shea Butter Preparations

In an embodiment, a "shea butter preparation" is included in a composition of the present invention. A shea butter preparation, such as shea butter, and/or oil extracted from shea butter ("shea butter oil"), is prepared from or otherwise derived from any Shea tree, including but not limited to a Shea tree from Ghana. In an embodiment, shea butter or shea butter oil is Butyrospermum parkii butter (CAS 194043-92-0; EC 293-515-7); Butyrospermum parkii oil (CAS 91080-23-8, EC 293-515-7), and/or vegetable oil (CAS 68956-68-3, EC 273-313-5). Other shea butters and shea butter oils may be used in shea butter preparations of this invention, including those having different CAS or EC, or other identifying numbers.

In an embodiment, a Shea butter oil preparation includes chemicals having the general structure

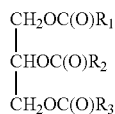

where $R_1$, $R_2$, $R_3$ are each individually $C_{15}$-$C_{17}$ saturated or $C_{17}$ unsaturated alkyl chains.

In an embodiment, Shea butter oil is prepared by a series of processes including mechanical extraction, solvent extraction, refinement, deodorization, and solvent fractionation. In an embodiment, Shea tree nuts undergo mechanical pressing and solvent extraction with hexane to prepare crude oil, which is then subjected to degumming with acidified water (phosphoric or citric acid) (degumming removes phospholipids, metals, and proteins), neutralization with alkaline water (sodium hydroxide) (neutralization removes free fatty acids, metals, and proteins), and bleaching with bleaching earth (clay) and citric acid (bleaching removes pigments, metals, and proteins) to prepare a bleached oil. Then, the bleached oil is mixed with solvent and cooled (separating solid and liquid constituents), filtered, solvent (hexane and/or acetone) recovered; and then deodorized with steam (removes flavors, free fatty acids, oxidation products and residual solvent). In an embodiment, Shea butter oil according to the present invention is liquid at room temperature, has a red color, a density (25° C.) of 0.9-0.94 g/cm³, a fatty acid composition (w/w) for instance as follows: 5% C16:0, 28% C18:0, 56% C18:1, 9% C18:2, 0.3% C18:3, 1% C20:0, 1% C22:0, available as Lipex SheaLiquid™ (AAK Sweden AB, Karlshamn, Sweden, SE-374-82).

In an embodiment, as disclosed in part for instance in Table 2 above, a composition according to the present invention may include about 0.1%-50% of a shea butter preparation, such as shea butter or shea butter oil. In a preferred embodiment, a composition according to the present invention includes about 1% to about 30% w/w of a shea butter preparation wherein the preparation is shea butter; about 8% to about 20% w/w shea butter; about 12% to about 18% w/w shea butter; about 14 to about 16% w/w shea butter; or about 15% w/w shea butter, for instance as shown in Tables 5-13 above. In an embodiment, a composition according to the present invention includes about 1% to about 20% w/w of a shea butter preparation wherein the preparation is shea butter oil; about 2% to about 15% w/w of a shea butter oil preparation; about 3% to about 8%; or about 4 to about 6% w/w of a shea butter oil preparation, for instance as shown in Table III below.

In an embodiment, the below components/ingredients are individually less than 10% of a composition of this invention (w/w); less than 5% of a composition of this invention (w/w); less than 3%, less than 2%, less than 1%, or less than 0.5% w/w of a composition of this invention (w/w).

Tri(Polyglyceryl-3/Lauryl Hydrogenated Trilinoleate)

In an embodiment, Tri(Polyglyceryl-3/Lauryl) Hydrogenated Trilinoleate may be used in a composition of this invention. In an embodiment, Tri(Polyglyceryl-3/Lauryl) Hydrogenated Trilinoleate according to the present invention is available in 100% pure form, as a brown, clear to hazy viscous liquid, with acid value 0-1 mg KOH/g and hydroxyl value 100-115 mg KOH/g as Cithrol PGTL (Croda Europe Ltd, East Yorkshire, DN14 9AA).

In an embodiment, a composition according to the present invention may include 0-10% w/w of Tri(Polyglyceryl-3/Lauryl Hydrogenated Trilinoleate), preferably about 0.5% to about 5% w/w, more preferably about 1% to about 2% w/w.

Tetrahexyldecyl Ascorbate

In an embodiment, tetrahexyldecyl ascorbate may be included in a composition of this invention. In an embodiment, tetrahexyldecyl ascorbate according to the present invention is in liquid form at room temperature, colorless to pale yellow, soluble in oil (hydrophobic). In an embodiment, its specific gravity (20° C.) is 0.930-0.943, its refractive index (25° C.) is 1.459-1.465, and/or assay results show tetrahexyldecyl ascorbate used according to the present invention is at least 95% pure. In an embodiment, tetrahexyldecyl ascorbate is at least 95% (w/w) pure, at least 96%, at least 97%, at least 98%, at least 99%, or is 100% (w/w) pure. Tetrahexyldecyl ascorbate may include substances categorized as CAS 183476-82-6 and/or CAS 1445760-15-5; and/or as EINECS 430-110-8. In an embodiment, tetrahexyldecyl ascorbate according to this invention includes no more than 20 ppm heavy metals and no more than 2 ppm arsenic. In an embodiment, loss of tetrahexyldecyl ascorbate on drying is no more than 0.5% (w/w).

In an embodiment, tetrahexyldecyl ascorbate according to the present invention is provided as BV-OSC (Barnet Products, Englewood Cliffs, N.J., USA).

Caryophyllene

In an embodiment, caryophyllene oil may be included in a composition of this invention. In an embodiment, caryophyllene is a hydrophobic component of the present invention, and is at least 85% pure (w/w). In an embodiment, caryophyllene oil is at least 90% pure, at least 95% pure, 98%-100% pure; and/or 100% pure. In an embodiment, caryophyllene oil has a specific gravity (25° C.) of 0.8990-0.9080, a refractive index (20° C.) of 1.4900-1.5040, and is free of mold Carvacrol In an embodiment, carvacrol may be included in a composition of this invention. In an embodiment, carvacrol, also known as cymophenol, is a monoterpenoid phenol and an ingredient in the oil of wild bergamot, *Origanum vulgare*, and oil of thyme. In an embodiment, at room temperature carvacrol is a corrosive liquid, acidic. In an embodiment, carvacrol is at least 90% (w/w) pure by assay, at least 95% pure, at least 97% pure, at least 98% pure, at least 99-100% pure. In an embodiment, carvacrol according to the present invention is available from Flavorchem Orchidia Fragrances, Downers Grove, Ill., USA.

Copaiba Oil

In an embodiment, Copaiba oil may be included in a composition of this invention. In an embodiment, Copaiba oil according to the present invention is the substance accorded CAS 8013-97-6, EINECS 232-288-0; INCI name *Copaifera Officinalis* (Balsam Copaiba) Resin, and/or sold as a 100% natural oil, Caribpure™ Copaiba Oil, CaribOrg™ Copaiba Oil (Caribbean Natural Products Inc., Fairfield, N.J., USA). In another embodiment, the present invention includes Copaiba oil (100% natural oil/balsam extracted from *Copaifera Officinalis*), CAS 8001-61-4. DL-alpha-Tocopheryl Acetate (also known as 3,4-Dihydro-2,5,7,8-tetramethyl-2-(4,8,12-trimethyltridecyl)-2H-1-benzopyran-6-yl acetate)

In an embodiment, DL-alpha-Tocopheryl Acetate may be included in a composition of this invention. In an embodiment, DL-alpha-Tocopheryl Acetate is a colorless-to-yellow viscous liquid oil, melting point about −27.5° C., boiling point 184° C. (0.01 hPa), 267° C. (3.2 hPa), >300° C. (1,013 hPa) with decomposition, flash point about 243-266° C. (per DIN 51758), hydrophobic/practically insoluble in water but easily soluble in acetone, chloroform, diethylether, alcohol, molecular weight 472.73 g/mol. In an embodiment, DL-alpha-Tocopheryl Acetate of this invention is 96-100% (w/w) CAS 7695-91-2, molecular formula $C_{31}H_{52}O_3$. In an embodiment, DL-alpha-Tocopheryl Acetate of this invention is from DSM Nutritional Products (Parsippany, N.J., USA). DL-alpha-Tocopherol (also known as 3,4-Dihydro-2,5,7,8-tetramethyl-2-(4,8,12-trimethyltridecyl)-2H-1-benzopyran-6-ol); 2,5,7,8-tetramethyl-2-(4,8,12-trimethyltridecyl)-6-chromanol; DL-alpha-tocopherol; tocopherol (INCI); vitamin E In an embodiment, DL-alpha-tocopherol may be included in a composition of this invention. In an embodiment, DL-alpha-tocopherol is the substance identified as CAS 10191-41-0, EINECS 233-466-0, $C_{29}H_{50}O_2$, molecular mass 430.72 g/mol. In an embodiment, 0.91 mg of DL-alpha-tocopherol is equivalent to 1.0 IU of vitamin E. In an embodiment, DL-alpha-tocopherol of this invention is a clear, viscous oil, colorless to yellowish brown, optical rotation −0.01° to +0.01°, refractive index (589 nm, 20° C.) 1.503-1.507, absorbance in ethanol (292 nm (max)) 71.0-76.0, acidity max. 1.0 mL 0.10N NaOH, sulphated ash (residue on ignition) max 0.1%, heavy metals max. 10 ppm (lead max 2 ppm, arsenic max 1 ppm, mercury max. 1 ppm, cadmium max. 0.5 ppm, residual solvents—toluene max 80 ppm, and/or related impurities max 2.5%, all for instance per Ph. Eur. By assay (Ph. Eur.), DL-alpha-tocopherol is in an embodiment 97.0-102.0%. Also, DL-alpha-tocopherol is insoluble in water, soluble in ethanol, miscible with chloroform, acetone, ether, vegetable oils; and/or sensitive to air and light. In an embodiment, oils and fats used for dilutions are low in peroxides, as rancid oils and fats may destroy the activity of DL-alpha-tocopherol. In an embodiment, DL-alpha-tocopherol is prepared synthetically by condensation of trimethylhydroquinone and isophytol. The crude product is purified by distillation in vacuo. As described above, Vitamin E may be helpful for instance as an anti-oxidant and in skin conditioning/wound healing. In an embodiment, DSM Nutritional Products Ltd. (Basel, Switzerland).

Ferulic Acid

In an embodiment, ferulic acid may be included in a composition of this invention. In an embodiment, ferulic acid is a synthetic, slightly yellow powder, >99% pure by HPLC assay, with less than 0.5% loss on drying at 105° C. for 1 hour, and/or having a melting point of 170° C.-175° C. In an embodiment, ferulic acid of this invention is at least 90% (w/w) pure, at least 95% (w/w) pure, at least 97% (w/w) pure, at least 99% (w/w) pure, and/or is 100% pure. In an embodiment, the ferulic acid of the present invention is about 99.7% (w/w) pure. The CAS number for ferulic acid is 1135-24-6. In an embodiment, ferulic acid of this invention is from GfN Herstellung von Naturextrakten GmbH, Wald-Michelbach, Germany.

Oleic Acid and Linoleic Acid

In an embodiment, oleic acid (CAS 112-80-1, EINECS 204-007-1) and linoleic acid (CAS 60-33-3, EINECS 200-470-9)) may be included in a composition of the present invention individually or as a blend, such as GLB Custom Oleic Acid & Linoleic Acid Blend SF (Green Line Botanicals, Hazlet, N.J., USA). The blend is a colorless to golden yellow liquid, dispersible in oil, with maximum 0.1% moisture and impurities. Under a cold test, 0° C./5.5 hours (Cc 11-53), the blend is clear.

Oils/Indian Oil Blend

In an embodiment, a composition of the present invention includes one or more of the following functional oils: Black Cumin Seed Oil, Baobab Oil, *Camellia* Oil, Manila Oil, Sea Buckthorn Oil, Tamanu Oil, Apricot Kernel Oil, Argan Oil. In an embodiment, a composition of the present invention includes all of the above oils. As an example, the following Indian Oil Blend (Rakesh Sandal Industries, Kanpur, India) includes the following oils (all from Rakesh Sandal Industries, Kanpur, India) and may be used in this invention:

Black Cumin Seed Oil (58% w/w of the Indian Oil Blend): Cold pressed oil from black cumin seeds (*Nigella sativa*), brownish color with a disagreeable, unpleasant odor. Acid value 8.3, refractive index 1.4728, specific gravity 0.9186, soluble in oil and insoluble in water, stable under normal conditions but oxidizing materials should be avoided.

Baobab Oil (3% w/w of the Indian Oil Blend): Cold pressed oil from *Adansonia digitata* seeds, yellow color, with a bland, fatty oil odor. Acid value 32.78, refractive index 1.4703, specific gravity 0.9172, soluble in oil and insoluble in water, stable under normal conditions but oxidizing materials should be avoided.

*Camellia* Oil (12% w/w of the Indian Oil Blend): Cold pressed oil from *Camellia sinensis* seed, yellow color, with a bland and fatty oil odor. Acid value 0.18, refractive index 1.4736, specific gravity 0.9181, soluble in oil and insoluble in water, stable under normal conditions but oxidizing materials should be avoided.

Manila Oil (3% w/w of the Indian Oil Blend): Cold pressed from seeds, yellow color, bland, fatty, nutty aroma. Acid value 0.77, refractive index 1.4691, relative density 0.9132, soluble in oil and insoluble in water, stable under normal conditions but oxidizing materials should be avoided.

Sea Buckthorn Oil (6% w/w of the Indian Oil Blend): Cold pressed from berries and seeds, with a yellow-brown to a red brown oil liquid and having a strong musky smell, characteristic neutral odor. Acid value 2.1, refractive index 1.4758, specific gravity 0.9229, soluble in oil and insoluble in water, stable under normal conditions but oxidizing materials should be avoided.

Tamanu Oil (6% w/w of the Indian Oil Blend): Cold pressed from seeds/nuts of *Calophyllum inophyllum*, with a dark yellow oil and heavy fatty, odoriferous odor. Optical rotation +1.40, refractive index 1.4983, specific gravity 1.0371, soluble in oil and insoluble in water, stable under normal conditions but oxidizing materials should be avoided.

Apricot Kernel Oil (6% w/w of the Indian Oil Blend): Cold pressed oil from apricot kernels, light yellow to golden yellow liquid, with a bland, fatty, nutty, deep odor. Acid value 1.34, refractive index 1.4728, specific gravity 0.9205, soluble in oil and insoluble in water, stable under normal conditions but oxidizing materials should be avoided.

Argan Nut Oil (6% w/w of the Indian Oil Blend): Cold-pressed oil from argan nuts, light yellow color with a nutty, oily, spicy odor. Acid value 0.1, refractive index 1.4704, specific gravity 0.9148, soluble in oil and insoluble in water, stable under normal conditions but oxidizing materials should be avoided.

Taken together, the Indian Oil Blend is characterized by a dark yellow color, pleasant odor, acid value 1 to 10, refractive index 1.4510 to 1.4980, specific gravity 0.8830 to 0.9360, soluble in oil and insoluble in water, stable under normal conditions (oxidizing materials to be avoided).

Soluble Collagen

In an embodiment, soluble collagen may be included in a composition of the present invention. In an embodiment, soluble collagen such as ichtyocollagen of this invention comprises native fish collagen. In an embodiment, Ichtyocollagen™ may be used as a soluble collagen component of this invention. In an embodiment, ichtyocollagen has film-forming and moisturizing, skin conditioning properties. In an embodiment, ichtyocollagen is in liquid form at 25° C., colorless to pale yellow, with appearance clarity of clear to slightly opalescent. In an embodiment, ichtyocollagen includes 0.4-0.7% protein (by BCA), pH 3.5-4.5, specific gravity (20° C.) 1.000-1.020, refractive index (25° C.) 1.34-1.36, hydroxyproline content 0.06-0.09%, and/or maximum 100CFU/G total aerobic microbial count and maximum 10 CFU/G total combined yeast/mold count. In an embodiment, ichtyocollagen comprises soluble collagen (INCI), CAS 9007-34-5, EINECS 232-697-4; as well as propylene glycol (approx. 10%), phenoxyethanol (1.5%), potassium sorbate (0.05%), trisodium EDTA (0.1%). In an embodiment, ichtyocollagen includes about 88% of natural origin content. Ichtyocollagen™ PH (Croda/Sederma Inc., Edison, N.J., USA)

Magnesium Sulfate

In an embodiment, magnesium sulfate may be a component of the present invention. In an embodiment, Magnesium Sulfate is from Spectrum Chemical Manufacturing Corp (New Brunswick, N.J., USA), is anhydrous, and assays at 99-100.5% (w/w) magnesium sulfate. In an embodiment, the pH of magnesium sulfate in solution (1 in 20) is 5.0-9.2, loss on drying is at most 2%, chloride content is at most 0.014%, iron content is at most 20 ug/g.

Caprylic/Capric Triglycerides

In an embodiment, caprylic and capric triglycerides ("caprylic, capric" or "caprylic/capric", or "cocoglycerides" (INCI Name, US/EU/CN)) may be included in a composition of the present invention. In an embodiment, caprylic/capric triglycerides according to the present invention provide a low viscosity oil at room temperature. In an embodiment, Myritol® 331 (BASF Corporation, Florham Park, N.J., USA) the low viscosity oil is clear and slightly yellowish, with a faint inherent odor. The acid value of Myritol® 331 is max. 2.00 mg KOH/g (DGF C-V 2), the saponification value ranges within 265-295 mg KOH/g (DGF C-V 3), density (20° C.) 0.930-0.940 g/cm$^3$ (DIN 51757), and refraction index (20° C.) 1.4500-1.4600 (DGF C-IV 5). In addition, additional product descriptive data (proven statistically but not determined regularly) for Myritol® 331 is iodine value (Hanus) max. 8.0 g I/100 g (DGF C-V 11A); Hydroxyl value 40.0-50.0 mg KOH/g (DGF C-V 17A,B); Cloud point max 5° C. (ISO 3015); Viscosity (20° C.; Hoeppler) 43.0-48.0 mPas (DGF C-IV 7).

Niacinamide

In an embodiment, niacinamide may be included in a composition of the present invention. In an embodiment, Niacinamide is a white crystalline powder, particle size 90% w/w greater than or equal to 50 um and 10% w/w smaller than 50 um, pH 6.0-7.5 in aqueous solution, and/or pKa about 3.35. Niacinamide is freely soluble in water (e.g. 691 g/L (20° C.)) and in alcohol, soluble in glycerol. In an embodiment, niacinamide is CAS 98-92-0, EC 202-713-4, IENECS 202-713-4. In an embodiment, the niacinamide is at least 90% pure, at least 95% pure, at least 98% pure, at least 99% pure, and/or at least 100% pure. In an embodiment, niacinamide in a composition of the present invention includes the above properties and assays as 99-101% niacinamide w/w (99-100% pure) (DSM Nutritional Products, Parsippany, N.J., USA).

Methyl Sulfonyl Methane (MSM; INCI: Dimethyl Sulfone)

In an embodiment, MSM may be included in a composition of the present invention. In an embodiment, MSM is a white crystalline powder, 90-100% pure (w/w; preferably 99-100% pure MSM), 80 mesh. (Orient Stars, Long Beach, Calif., USA).

Roman Chamomile Oil

In an embodiment, Roman Chamomile Oil may be included in a composition of the present invention. In an embodiment, Roman Chamomile Oil may be used in a composition of this invention. The oil may be from the flower of the *Anthemis nobilis* flower, a colorless to yellow liquid, and 100% oil, unadulterated by other substances. In an embodiment, Roman Chamomile Oil of this invention is the substance accorded CAS 8015-92-7. In an embodiment, Roman Chamomile Oil that may be used in this invention is 100% oil from the *Anthemis nobilis* flower as provided by GlobalIngredientSolutions.com (Tustin, Calif., USA).

Retinyl Palmitate

In an embodiment, Retinyl Palmitate may be used in a composition of this invention. In an embodiment, the Retinyl Palmitate is provided as a yellowish viscous oil and in combination with Tocopherol. The oil is crystalline when cooled. In such embodiment, as provided by BASF Care Creations (BASF Corporations, Florham Park, N.J., USA) Retinyl Palmitate content is 1.70-1.87 Mio IU/g (where 1 IU=0.550 mcg retinyl palmitate, potentially equivalent to 93.5-103%), and tocopherol content is 1.7%. Further, the Peroxide value of the combination of Retinyl Palmitate and tocopherol is, at most, 10 meq/kg; the acid value is at most 2.0 mg KOH/g; the amount of retinol is at most 1.0%; related substances absorbance ratio A 300/A 326 nm is at most 0.6; related substances absorbance ratio A 350/A 326 nm is at most 0.54; related substances absorbance ratio A 370/A 326 nm is at most 0.14. In this embodiment, the Retinyl Palmitate oil described above meets "Vitamin A" and "Vitamin A Concentrate (Oily Form), synthetic" specifications of the Ph. Eur., and "Vitamin A" of USP.

Others

In an embodiment, 1,2-Hexanediol (CAS 6920-22-5, EC 230-029-6) and/or Caprylyl Glycol (1,2-Octanediol; CAS 1117-86-8, EC 214-254-7) may be included in a composition of the present invention. In an embodiment, they are provided in a composition as SymDiol® 68 (Symrise, Elk Grove Village, Ill., USA), a colorless clear liquid with a mild characteristic odor, having a refractive index (n25/D) of 1438-1448. In an embodiment, 1,2-Hexanediol and Caprylyl Glycol are each present in amounts of greater than 25% w/w and less than or equal to 50% w/w of the overall composition (about 25-50%). In an embodiment, the total amount of the two substances combined comprises about 98% of the Symdiol® 68 combination, such that 1,2-Hexanediol and Caprylyl Glycol are each present in amounts of about 49-50% w/w of the SymDiol.

In an embodiment, included in a composition of the present invention, the following are presented for instance all together in one aqueous solution (PRODEW 600 (Ajinomoto, Raleigh, N.C., USA)): Trimethylglycine (26.87%) ("Betaine" CAS 107-43-7, EINECS 203-490-6), Sodium L-pyrrolidonecarboxylate (9.75%) ("Sodium PCA", CAS 28874-51-3, EINECS 249-277-1), Sodium Lactate (5.00%) (CAS 72-17-3, EINECS 200-722-0), DL-Pyrrolidonecarboxylic Acid (3.78%) ("PCA", CAS 149-87-1 EINECS 205-748-3), L-Serine (1.12%) ("Serine", CAS 56-45-1, EINECS 200-274-3), L-Alanine (1.06%) ("Alanine", CAS 56-41-7, EINECS 200-273-8), Glycine (1.00%) (CAS 56-40-6, EINECS 200-272-2), L-Glutamic acid (0.43%) ("Glutamic Acid", CAS 56-86-0, EINECS 200-293-7), L-Lysine Hydrochloride (0.34%) ("Lysine HCL", CAS 657-27-2, EINECS 211-519-9), L-Threonine (0.32%) ("Threonine", CAS 72-19-5, EINECS 200-774-1), L-Arginine (0.29%) ("Arginine", CAS 74-79-3, EINECS 200-811-1), L-Proline (0.04%) ("Proline", CAS 147-85-3, EINECS 205-702-2), and Water (balance; approx. 50%) (CAS 7732-18-5, EINECS 231-791-2) are combined into a colorless to pale yellow liquid, in an approximately 50% aqueous solution (solid content about 47-53%), pH 4.7-5.4.

The present invention may be further understood in connection with the following Examples and embodiments. The following non-limiting Examples and embodiments described throughout this application are provided to illustrate the invention.

Example A

Large Scale Composition for Treatment of Dupuytren's Disease and Contracture, and Process of Making the Composition The composition prepared in Table 5 according to the process of Example 22, above, reduces Dupuytren's symptoms. The process of Example 22 may prepare a water-in-oil emulsion, as described, or an oil-in-water emulsion, by controlling mixing and temperature properly. In that process, solid components could be selected that melted at 35° C.-40° C. to maintain stability of the product when cooled and liquid during mixing, and also to melt on the skin as it was applied.

The Applicant engaged in research as described below and developed another process for preparing compositions of the present invention. In contrast to the process described in Example 22 above, the alternative process avoids the need for heating to high temperatures, 60° C.-80° C. Also, the process allows for the preparation of large batches of compositions of the present invention.

The composition prepared according to this Example A contains the following ingredients:

TABLE III

| COMPONENT | HYDROPHILIC/ HYDROPHOBIC | % COMPOSITION (W/W) |
| --- | --- | --- |
| Water | HYDROPHILIC | 61.83016 |
| Aloe barbadensis Leaf Extract (200X) | HYDROPHILIC | 14.83404 |
| Butyrospermum Parkii Butter | HYDROPHOBIC | 5.28000 |
| Alpha Pinene | HYDROPHOBIC | 3.24000 |
| Black Cumin Seed Oil | HYDROPHOBIC | 2.94640 |
| Tri(Polyglyceryl-3/Lauryl) Hydrogenated Trilinoleate | HYDROPHOBIC | 1.20000 |
| Methyl SulfonylMethane (MSM) | HYDROPHILIC | 1.00000 |
| Sodium Hydroxide | HYDROPHILIC | 1.00000 |
| Betaine | HYDROPHILIC | 0.827596 |
| Carvacrol | HYDROPHOBIC | 0.80000 |
| Magnesium Sulfate | HYDROPHILIC | 0.70000 |
| Camellia Oil | HYDROPHOBIC | 0.60960 |
| Caryophyllene | HYDROPHOBIC | 0.56000 |
| Caprylyl Glycol | HYDROPHILIC | 0.48000 |
| 1,2-Hexanediol | HYDROPHILIC | 0.32000 |
| Apricot Oil | HYDROPHOBIC | 0.30480 |
| Argan Oil | HYDROPHOBIC | 0.30480 |
| Sea Buckthorn Oil | HYDROPHOBIC | 0.30480 |
| Tamanu Oil | HYDROPHOBIC | 0.30480 |

TABLE III-continued

| COMPONENT | HYDROPHILIC/ HYDROPHOBIC | % COMPOSITION (W/W) |
| --- | --- | --- |
| Sodium PCA | HYDROPHILIC | 0.30030 |
| Caprylic/Capric Triglyceride | HYDROPHOBIC | 0.30000 |
| Copaiba Oil | HYDROPHOBIC | 0.30000 |
| Roman Chamomile Oil | HYDROPHOBIC | 0.30000 |
| Linoleic Acid | HYDROPHOBIC | 0.28000 |
| Oleic Acid | HYDROPHOBIC | 0.28000 |
| Propylene Glycol | HYDROPHILIC | 0.22400 |
| Ferulic Acid | HYDROPHILIC | 0.19940 |
| Sodium Lactate | HYDROPHILIC | 0.15400 |
| Baobab Oil | HYDROPHOBIC | 0.15240 |
| Marula Oil | HYDROPHOBIC | 0.15240 |
| Niacinamide PC | HYDROPHILIC | 0.14000 |
| PCA | HYDROPHILIC | 0.116424 |
| Serine | HYDROPHILIC | 0.034496 |
| Alanine | HYDROPHILIC | 0.032648 |
| Glycine | HYDROPHILIC | 0.03080 |
| Tetrahexyldecyl Ascorbate | HYDROPHOBIC | 0.03000 |
| Tocopheryl Acetate | HYDROPHOBIC | 0.03000 |
| Retinyl Palmitate | HYDROPHOBIC | 0.02949 |
| Soluble Collagen | HYDROPHILIC | 0.02240 |
| Glutamic Acid | HYDROPHILIC | 0.013244 |
| Lysine HCL | HYDROPHILIC | 0.010472 |
| Threonine | HYDROPHILIC | 0.009856 |
| Arginine | HYDROPHILIC | 0.008932 |
| Proline | HYDROPHILIC | 0.001232 |
| Tocopherol | HYDROPHOBIC | 0.00051 |
| TOTAL | | 100% |

The formulation of a large number of components such as in the present invention is generally difficult to achieve. Without appropriate formulation, the hydrophilic and hydrophobic components will separate from each other, reducing delivery and effectiveness of the components to the target, and rendering the composition difficult to apply and undesirable for topical application.

The formula included Ingredient's trade/brand names with percentages of each ingredient as in the following.

TABLE IV

| Original composition | |
| --- | --- |
| Ingredients | % by Wt. |
| Water | QS - 100 |
| Aloe Vera 200x (powder) | 15.42 |
| Ferulic Acid (Powder) | 0.20 |
| MSM (Powder) | 1.00 |
| Glycerin | 0.50 |
| Niacinamide (Crystalline) | 0.84 |
| Magnesium Sulfate (powder) | 0.70 |
| Ichtycollagen | 2.24 |
| Prodew 600 (Blend) | 3.08 |
| Vitacon ACES | 0.42 |
| GLB (Blend) | 0.56 |
| Liquid Shea TR | 5.28 |
| Indian Oil (Blend) | 5.05 |
| Custom Sense A1 (Blend) | 1.68 |
| Alpha Pinene | 3.36 |
| Caryophyllene | 0.56 |
| Cavracrol | 0.56 |

This composition contains both oil soluble and water soluble ingredients. The physical form of these ingredients is either liquid or solid (crystalline/powder/flakes). In addition some of these ingredients are blends that will make the ingredient list appear much longer than in Table IV. See below Table VII.

When a formulation contains water soluble and oil soluble ingredients the common practice is to make an emulsion. The emulsion can exist in various forms such as cream, lotion, milk, and thin liquid. The emulsions are sensitive to changes in temperature and time. If not formulated properly an emulsion will separate over time due to hot/cold temperature fluctuations and/or even with passage of time The development of the large-scale composition requires a few considerations such as:
- Careful selection of ingredients, keeping in mind the compatibility of the ingredients;
- Proper selection of emulsifiers that bind the oil and water together; and
- Process of manufacturing that can significantly affect the stability of the end product.

In this case the active or functional ingredients and their quantities were preset, based on the composition for treating Dupuytren's discussed in Table 5 and Examples 1-4 above.

Development

O/W Emulsion

Generally, emulsions fall in two groups: oil in water (O/W) and water in oil (W/O). Majority of the creams and lotions on the market are O/W emulsions. As part of the tests, a number of emulsifiers, co emulsifiers, and thickeners were used to develop O/W emulsion. However, the stability in the O/W tests was not as reliable, which may be attributable to the fact that this composition contains high amount of electrolytes. Electrolytes are ingredients that provide ions (electrically charged entities) in solution.

W/O Emulsion

Next step was to move to water in oil (W/O)[17] emulsion system which, without being bound by theory, may have a slightly better electrolyte tolerance than oil in water (O/W) emulsion. In water in oil emulsions the outer phase of the emulsion is oil. For this reason these emulsions behave more like an oil. The texture and feel of application of W/O emulsions is different than O/W emulsions. Table V lists the emulsifiers and thickener evaluated in this phase.

TABLE V

Emulsifiers and thickeners evaluated in W/O system

| Trade Name | INCI | Emulsifier/Thickener |
|---|---|---|
| Easynov[1] | Octyldodecanol(and) octyldodecyl xyloside(and) PEG-30 dipolyhydroxystearate | Emulsifier |
| Sepinov EMT-10[5] | Hydroxyethyl Acrylate/Sodium, Acryloyldimethyl Taurate Copolymer | Thickener |
| Sepiplus 400[12] | Polyacrylate 13/Polyisobutene/Polysorbate 20 | Thickener/Emulsifier |
| Sepimax Zen[4] | Polyacrylate Crosspolymer-6 | Thickener/Emulsifier |
| Cithrol PGTL[3] | Tri(Polyglyceryl-3/Lauryl) Hydrogenated Trilinoleate | Emulsifier |
| Emulium Illustro[2] | Polyglyceryl-6 Polyhydroxystearate, Polyglyceryl-6 Polyricinoleate | Emulsifier |
| Solagum | *Acacia Senegal* Gum (and) Xanthan Gum | Thickener |

These emulsifiers although support W/O emulsion, are different in chemical structure and properties. The water in oil emulsion is conventionally made by adding the aqueous phase into the oil phase while mixing at a moderate to high speed, and then homogenizing.

The work was started with Easynov. Easynov has unique property that allows the emulsion to be made both ways 1. By adding the oil phase into the gelled/thickened water phase with only slow mixing Different gelling agents (Sepiplus 400, Sepinov EMT-10 and Sepimax Zen) were evaluated. The emulsion made by adding oil phase into water phase turned out to be unstable.

2. By adding the water phase into the oil phase (conventional).

The emulsion made by adding water phase into oil phase while mixing at a moderate to high speed was found to be stable for 4 weeks at 40° C. After 4 weeks slight oil was observed floating on the surface that disappears after shaking.

The next emulsifier Emulium Illustro, a polyglyceryl based emulsifier, is naturally derived. The emulsion made with conventional process separated overnight at 40° C.

Cithrol PGTL was the next emulsifier, another polyglyceryl based emulsifier. The process involved adding of water phase into the oil phase with moderate to high speed mixing followed by homogenizing and then normal mixing.

TABLE VI

Combinations and levels of emulsifiers & thickeners in W/O system

| Trade Name | 1 | 2 | 3 | 4 | 5 | 6 | 7 | 8 | 9 |
|---|---|---|---|---|---|---|---|---|---|
| Easynov[1] | 3.00 | 3.00 | 3.00 | 3.00 | 3.00 | 3.00 | | | |
| Sepinov EMT-10 | 2.00 | 3.00 | | | | | | | |
| Sepiplus 400[12] | | | 3.00 | | | | | | |
| Sepimax Zen[4] | | | | 2.5 | 1.00 | | | | |
| Emulium Illustro[2] | | | | | | | 2.00 | | |
| Cithrol PGTL[3] | | | | | | | | 1.20 | 1.20 | 1.20 |
| Sepimax Zen | | | | | | | | 0.50 | 0.10 |
| Cold Process | Mod | Mod | Mod | Mod | Mod | Conv | Conv | Conv | Conv | Conv |
| Stability | Sep | Sep | Sep | Sep | Sep | 5 wk | Sep | 5 wk | Sep | Sep |

Observations

Two processes were tested in the making of W/O emulsion (the conventional process) and the modified process. The modified process was applicable only to one emulsifier Easynov.

Conventional Process: Water and oil phases were prepared separately. Water phase contained water and all water soluble ingredients including powders and electrolytes. The oil phase contained oils, waxes and other oil soluble ingredients such as esters. After all the water phase is added to the oil phase the product is homogenized and mixed for a few minutes.

Modified Process: This process is specific to one emulsifier Easynov[1]. The water and oil phases were prepared separately. This process has water phase to be thick like gel consistency. The oil phase is then added to the top of the water phase before the mixing starts. The bulk is then mixed very slowly until all the oil phase on top blends in.
1. The emulsions made with the modified process using Easynov appeared unstable.
2. The conventional process was also evaluated using Easynov. The emulsion made with the conventional process using Easynov emulsifier was stable at 40 C for 4 weeks, indicating that a process change can make a difference in the stability and other properties of the end product. In long term slight oil floating was observed on top. Upon shaking the bottle this oil goes back into emulsion. The product did not remain stable when frozen and thawed later. Once separated as a result of freezing and thawing ("F/T") the product did not go back into emulsion by shaking. Easynov is PEG-based emulsifier.
3. The conventional W/O[17] emulsion made with Emulium Illustro separated in one day at 40° C. This separated emulsion did not go back together with shaking. Emulium illustro is a Polyglyceryl 6 or Polyglycerol 6 based emulsifier.
4. Cithrol PGTL based conventional W/O emulsion was stable for 5 weeks at 40 C. The long term stability at 40° C. exhibited the similar slight oil floating on the surface as in case of Easynov. After shaking the product becomes uniform again. This product did not remain stable when frozen and thawed. Once separated in F/T test it did not go back to uniform emulsion by shaking.

To improve F/T stability following stabilizers were tried
1. Solagum—at 1% level
2. Sepimax Zen—at 1%, 0.5%, 0.25% and 0.1%

Sepimax Zen appeared to improve the F/T stability, but at the expense of normal or accelerated stability. It means that the F/T stability is improved but the stability at 40° C. is adversely affected, and it does not seem to go back after shaking. It seems like Sepimax Zen kicks out of the system.

DISCUSSION

In creating a large-scale, stable formula for topical application, without heating natural ingredients, in quantities known to treat or alleviate certain skin or tissue conditions, for instance Dupuytren's disorder.

Stability translates into shelf life. Shelf life indicates how long a product can stay on the shelf under normal/ambient conditions without deteriorating its utility. Stability testing therefore consists of the following parts.
1. Accelerated stability at 40° C. for 3 months.
2. Stability at ambient conditions (20° C.-25° C.) for 2 years
3. Preservative efficacy testing (PET) before the start and at the end of accelerated stability.
4. Three F/T cycles (8 hours of freezing and 8 hours of thawing each cycle)

In determining shelf life, accelerated stability gives an indication of 2 years of shelf life within 3 months of testing. The PET testing tells that the product will be safe throughout the shelf life. Usually the product is sold and used well before 2 years. PET also indicates that under normal use conditions product will not grow microbes (bacteria/yeast/mold).

Emulsifiers commonly contains water and oil, with one end being water loving (hydrophilic) and the other end oil loving (lipophilic).

Each emulsifier has a balance of hydrophilic and lipophilic parts which is called hydrophilic/lipophilic balance (HLB[16]). One emulsifier can be more hydrophilic than lipophilic and the other can be less hydrophilic then lipophilic. Also the hydrophilic and lipophilic may be equal in some emulsifiers. The two emulsifiers can have the same HLB but may differ in structure. One of the two with same HLB may work for a given composition and the other may not depending on the chemical structure indicating that the structure function is more important than just the HLB[16]. Sometimes one or more additional emulsifier is added to assist the primary emulsifier. This is considered a co-emulsifier. In an embodiment, the HLB to the given composition may be finetuned, which may results in the improved stability and other properties of the emulsion.

There are many emulsifiers that work only based on the structure function and the physical behavior in the emulsion for example synthetic acrylic acid based polymers, copolymers and cross polymers. Other example may be polyethylene glycol (PEG) based, PPG based, polysorbate based, and polysilicone based emulsifiers which may or may not exhibit the HLB because of their specific structure configuration.

For O/W emulsions the emulsifier has to be more hydrophilic than lipophilic. For W/O the emulsifier has to be less hydrophilic and more lipophilic.

Emulium illustro is a blend of two ingredients which are Polyglyceryl-6 Polyhydroxystearate and Polyglyceryl-6 Polyricinoleate. Both have 6 polyglyceryl groups attached to a C18 carbon chain. The carbon chain provides a lipophilic character to the compound. Polyglyceryl group on the other hand provides a hydrophilic character because of the hydroxyl (OH) groups. Higher the number of OH groups higher the hydrophilic character. In this case C18 carbon chains each with 6 polyglyceryl groups.

Cithrol PGTL is Tri (Polyglyceryl-3/Lauryl) Hydrogenated Trilinoleate. In this case the lipophilic part is hydrogenated linoleate which is C18 chain. The other part is not only polyglyceryl 3, it has a lauryl chain (C12) attached to it. It means that polyglyceryl 3 is attached to two carbon chains C12 and C18. This shows that compared to Emulium illustro, Cithrol PGTL has more lipophilic character and differs in chemical structure too.

As set forth above two emulsifiers may behave differently even if they have same HLB but different structure. In this case two emulsifiers worked equally well with different chemistries Easynov and Cithrol PGTL.

Examples of other emulsifiers that may also work in this type of system either alone or in combination include—

Polyglyceryl-3 Sorbityl Linseedate (Sinerga); Polyglyceryl-2 Oleate (and) Polyhydroxystearic Add (and) Polyglyceryl-2 Stearate (Innovacos); Polyglyceryl-3 Triolivate (Acme Hardesty); Polyclyceryl-3 Polyricinoleate (IOI Oleo); Polyglyceryl-2 Dipolyhydroxystearate (BASF); Polyclyceryl-2 Sesquiisostearate (Clariant); Polyglyceryl-3 Diisostearate (Gattefosse, BASF); Polyglyceryl-6 Polyricinoleate (and) Polyglycery-3 Diisostearate (and) Disteardimonium Hectorite (Elementis); Olive Oil Polyglyceryl-6 Esters (and) Polyglyceryl-6 Pentaoleate (Coast Southwest); Polyglycery-6 Polyricilinoleate (and) Polyglyceryl-10 Dioleate (Grant); Cetyl PEG/PPG-10/1 Dimethicone (Evonik)[15]; Methylglucose Sesquioleate (Lubrizol).

CONCLUSION

Based upon repeated trials and tests, an example of stable formula is provided in the following Table VII.

TABLE VII

Exemplary quantitative formula with INCI names

| Large Scale Dupuytren's INCI NAME | wt % | Possible range % | Preferred % | More Preferred % |
|---|---|---|---|---|
| Water | 61.4636 | 50-70% | 55-65% | 60-62% |
| *Aloe barbandesis* Leaf Juice | 15.4200 | 3%-30% | 5%-25% | 8%-16% |
| *Butyrospermum Parkis* (Shea) Butter | 5.2800 | 0.5%-25% | 2%-15% | 5%-10% |
| Alpha Pinene | 3.2400 | 0.01%-20% | 1%-12% | 2.5%-7.5% |
| Black Cumin Seed oil | 2.9970 | 0.5-1.0% | 1-7% | 2.5-3.5% |
| Tri(Polyglyceryl-3/Lauryl) Hydrogenated Trilinoleate | 1.2000 | 0.05%-15% | 0.5%-10% | 0.8%-5% |
| Dimethyl Sulfone | 1.0000 | 0.001%-10% | 0.04%-6% | 0.5%-3% |
| Betaine | 0.8276 | 0.001%-10% | 0.04%-6% | 0.5%-3% |
| Cavracrol | 0.8000 | 0.01%-10% | 0.1%-5% | 0.5%-3% |
| Magnesium Sulfate | 0.7000 | 0.01%-10% | 0.1%-5% | 0.5%-3% |
| *Camellia* Oil | 0.5894 | 0.01%-10% | 0.1%-5% | 0.5%-3% |
| Caprylic/Capric Triglycerides | 0.5600 | 0.01%-10% | 0.1%-5% | 0.5%-3% |
| *Chamomilla Recutita* (*Matricaria*) Flower Oil | 0.5600 | 0.01%-10% | 0.1%-5% | 0.5%-3% |
| *Copaifera Officinalis* (Balsam Copaiba) Resin | 0.5600 | 0.01%-10% | 0.1%-5% | 0.5%-3% |
| Caryophyllene | 0.5600 | 0.01%-12% | 0.2%-6% | 0.5%-3% |
| 1,2-Hexanediol | 0.4000 | 0.01%-12% | 0.2%-6% | 0.5%-3% |
| Caprylyl Glycol | 0.4000 | 0.01%-12% | 0.2%-6% | 0.5%-3% |
| Sodium PCA | 0.3003 | 0.01%-12% | 0.2%-6% | 0.5%-3% |
| Apricot Oil | 0.2987 | 0.01%-12% | 0.2%-6% | 0.5%-3% |
| Argan Oil | 0.2987 | 0.01%-12% | 0.2%-6% | 0.5%-3% |
| Sea Buckthorn oil | 0.2987 | 0.01%-12% | 0.2%-6% | 0.5%-3% |
| Tamanu Oil | 0.2987 | 0.01%-12% | 0.2%-6% | 0.5%-3% |
| Oleic Acid | 0.2800 | 0.01%-12% | 0.2%-6% | 0.5%-3% |
| Linoleic Acid | 0.2800 | 0.01%-12% | 0.2%-6% | 0.5%-3% |
| Propylene Glycol | 0.2240 | 0.01%-12% | 0.2%-6% | 0.5%-3% |
| Ferulic Acid | 0.2000 | 0.01%-12% | 0.2%-6% | 0.5%-3% |
| Sodium Lactate | 0.1540 | 0.01%-12% | 0.2%-6% | 0.5%-3% |
| Baobab Oil | 0.1494 | 0.01%-12% | 0.2%-6% | 0.5%-3% |
| Marula Oil | 0.1494 | 0.01%-12% | 0.2%-6% | 0.5%-3% |
| Niacinamide | 0.1400 | 0.01%-12% | 0.2%-6% | 0.5%-3% |
| PCA | 0.1164 | 0.01%-12% | 0.2%-6% | 0.5%-3% |
| Serine | 0.0345 | 0.01%-12% | 0.2%-6% | 0.5%-3% |
| Alanine | 0.0326 | 0.01%-12% | 0.2%-6% | 0.5%-3% |
| Glycine | 0.0308 | 0.01%-12% | 0.2%-6% | 0.5%-3% |
| Tocopheryl Acetate | 0.0300 | 0.01%-12% | 0.2%-6% | 0.5%-3% |
| Tetrehexyldecyl Ascorbate | 0.0300 | 0.01%-12% | 0.2%-6% | 0.5%-3% |
| Retinyl Palmitate | 0.0294 | 0.01%-12% | 0.2%-6% | 0.5%-3% |
| Soluble Collagen | 0.0224 | 0.01%-12% | 0.2%-6% | 0.5%-3% |
| Glutamic Acid | 0.0132 | 0.01%-12% | 0.2%-6% | 0.5%-3% |
| Lysine HCL | 0.0105 | 0.01%-12% | 0.2%-6% | 0.5%-3% |
| Threonine | 0.0100 | 0.01%-12% | 0.2%-6% | 0.5%-3% |
| Arginine | 0.0089 | 0.01%-12% | 0.2%-6% | 0.5%-3% |
| Proline | 0.0012 | 0.01%-12% | 0.2%-6% | 0.5%-3% |
| Tocopherol | 0.0006 | 0.01%-12% | 0.2%-6% | 0.5%-3% |
| | 100.0000 | | | |

Without being bound by theory, other embodiments of this invention may be formulated into a conventional oil-in-water emulsion.

The above large-scale composition is useful in treating or alleviating Dupuytren's contracture according to the present invention. For instance, in an embodiment 15-30 ml of the composition of Table III prepared according to the process described herein was applied to the hands of an adult male suffering from Dupuytren's Disease and Contracture. The topical application, twice daily, reduced symptoms including contracture symptoms and prevented progression of the disease for a period of several months, as of the date of filing this application.

REFERENCES 1. https://www.seppic.com/easynov
2. https://www.ulprospector.com/en/na/PersonalCare/Detail/832/1309961/Emulium-Illustro
3. https://www.ulprospector.com/en/asia/PersonalCare/Detail/1411/988636/Cithrol-PGTL 4. https://www.ulprospector.com/en/na/PersonalCare/Detail/1432/121189/SEPIMAX-ZEN
5. https://www.ulprospector.com/en/na/PersonalCare/Detail/1432/57885/SEPINOV-EMT-10
6. https://www.ulprospector.com/en/na/PersonalCare/Detail/6823/637213/Emulfeel-SGP-CHI
7. https://cosmetics.specialchem.com/product/i-nikkol-nikkol-lecinol-s-10
8. https://www.ulprospector.com/en/na/PersonalCare/Detail/75/204260/Cosmedia-SP
9. https://www.utprospector.com/en/eu/PersonalCare/Detail/804/72263/Eummulgin-SG
10. https://www.ulprospector.com/en/na/PersonalCare/Detail/1432/46812/MONTANOV-68-MB
11. https://www.ulprospector.com/en/na/PersonalCare/Detail/1432/54516/MONTANOV-202
12. https://www ulprospector.com/en/na/PersonalCare/Detail/1432/46884/SEPIPLUS-400
13. https://www.ulprospector.com/en/na/PersonalCare/Detail/1432/238138/SEPINOV-WEO
14. https://www.ulprospector.com/en/na/PersonalCare/Detail/581/211534/DRY-FLO-TS-Starch
15. https://personal-care.evonik.com/product/personal-care/en/products-solutions/products/pages/product-details.aspx?productId=38993&category=3591
16. https://caliscc.org/images/presentations/Mentor_2015_HLB.pdf
17. https://pdfs.semanticscholar.org/47a1/ef550bfbd52aaf-351da88b11d92d03fac7c1.pdf?.ga=2.1576015 22.974714001.1589746793-1140813295.1589746793

A large-scale composition according to the present invention is prepared by a large-scale process, which may be as small as 100-300 mL, or as large as 3,000 L (100,000 units×30 mL each). In an embodiment, a large-scale process according to this invention is about 40 kiloliters per batch to more than 100,000 kiloliters per batch.

A large-scale process according to the present invention is directed to combining hydrophobic and hydrophilic components with high dosage of active ingredients to prepare a water-in-oil emulsion, comprising the steps of:

(a) placing water in a first vessel and stirring the water, adding aloe powder and mixing until dissolved, then adding other hydrophilic ingredients and mixing well, adjusting pH to about 6-8, to prepare a hydrophilic mixture; and mixing hydrophobic components in a second vessel to prepare a hydrophobic mixture;

(b) adding the hydrophilic mixture to the hydrophobic mixture with rapid mixing; and then (c) homogenizing the mixture, to prepare the water-in-oil emulsion.

In an embodiment, a manufacturing procedure for the large scale process to prepare a large-scale composition of this invention is as follows:

Step (a):

Water (hydrophilic) phase: In a side mixing tank equipped with a lightening mixer, add water (57.93 g) and Aloe Vera Gel 200× (15.42 g). Mix 15-20 minutes until all Aloe powder dissolves and a yellow colored solution is formed. Continue mixing and add rest of the water phase ingredients from one by one (Ferulic Acid (0.2 g), MSM (1.00 g), Niacinamide (0.14 g), Magnesium Sulfate (0.70 g), Ichtycollagen (2.2 g), Prodew 600 (3.08 g), Symdiol 68 (0.80 g). Using sodium hydroxide 10% solution adjust pH of water phase to 6.7-7. Mix thoroughly until uniform and homogenous.

Oil (hydrophobic) Phase: In the main mixing tank equipped with central turbine, side sweeps and a homogenizer, add all the oil phase ingredients (Tocopheryl Acetate (0.03 g), BVOSC (0.03 g), Retinyl Palmitate (0.03 g), Liquid Shea TR (5.28 g), Indian Oil Blend (5.08 g), Custom Sens AI (1.68 g), GLB Oleic Acid, Linoleic Acid (0.56 g), Alpha Pinene (3.24 g), Caryophyllene (0.56 g), Carvacrol (0.80 g), Cithrol PGTL (1.20 g)) one by one with continued mixing at a slow speed that barely creates a vortex. After all the oil phase ingredients have been added mix for additional 10-15 minutes until a uniform oil blend is formed. Increase the oil phase mixing speed to create a vortex (speed to be determined depending upon the equipment at the manufacturing site).

Step (b):

Start adding water phase in small portions at a time. The portions can be determined from the batch size. Mix for 2-3 minutes after each addition. After few portions of water phase have been added the mixing speed can be increased depending upon the viscosity or thickness of the emulsion. Rapid mixing may be used at this step.

Step (c):

After all the water phase is added to the oil phase, homogenize the emulsion thoroughly for 10-20 minutes until the whole batch is turned over. The product will gain viscosity at this time. If an in line homogenizer is present the whole batch can be transferred from one tank to another. This ensures that the whole batch is homogenized. After homogenizing, mix with propeller mixer for a few minutes to make uniform. Top and bottom samples may be pulled for quality control purposes, to analyze the water-in-oil emulsion prepared by this process.

The appearance of the composition starts changing at the time of emulsification. When the water phase is added to the oil phase. The above exemplary process is not intended as limiting. Other embodiments may be envisioned. Variations such as a change in emulsifiers from the listing included above, and a change of mixology depending upon available equipment, are and included embodiments of this invention. For instance instead of a lightening mixer, a side sweep mixer can be used, coupled with different ways of homogenizing like using colloidal mill in place of a homogenizer. Also, in an embodiment of this invention, a smaller emulsion particle size may aid stability of the emulsion.

A large-scale process preparing a water-in-oil emulsion according to this invention does not require heat. In an embodiment, no external heat source is needed. In an embodiment, the hydrophilic phase may be heated for instance by a heat source to 40° C.-45° C. to speed up the process, and the hydrophobic phase may be heated to help the hydrophobic phase become uniform.

In an embodiment, a water-in-oil emulsion for instance as prepared by the above process is filled into a pump bottle that may hold about 1 or about 2 L of emulsion. In an embodiment, the pump bottle may be used to prevent or reduce ambient air from accessing the stored emulsion. In an embodiment, the pump bottle dispenses 15 ml of the emulsion. In an embodiment, the emulsion prepared by this invention is an elegant, light-brown, easy to apply cream or lotion. In an embodiment, to treat Dupuytren's disease on both hands of a subject, 1-2 15 ml doses of emulsion are applied between both hands, twice a day. In an embodiment, the pump bottle will hold an approximate one-month supply of emulsion for a subject. In an embodiment, Dupuytren's symptoms will decrease over time, for instance as discussed in the Examples above.

Example B

Further embodiments of compositions of the present invention are set out below. As discussed above, in an embodiment of the present claims included are an aloe vera preparation, a shea butter preparation, alpha-pinene, and water. Hydrophobic and hydrophilic components are included in a composition of the present invention. In an embodiment, hydrophobic and hydrophilic components are included in approximately the same total amounts in a composition of this invention (for instance each totaling about 40%-60% w/w of the composition, not including water). In an embodiment, compositions of the present invention include about 25-70% water (e.g. distilled water). In an embodiment, all compositions prepared on a large scale according to the present invention are water-in-oil emulsions and include an emulsifier, as discussed for instance in Example A above. In an embodiment, a composition of the present invention is an oil-in-water emulsion. Additional hydrophobic components include black cumin seed oil, baobab oil, *camellia* oil, manila oil, sea buckthorn oil, tamanu oil, apricot kernel oil, and/or argan oil. Additional hydrophilic components include soluble collagen, amino acids, niacinamide, oleic acid, and/or protocatechuic acid.

In an embodiment a composition according to the present invention may include the following:

TABLE VIII

| Component | Hydrophilic/Hydrophobic | % of composition (w/w) |
| --- | --- | --- |
| *Aloe Vera* preparation | Hydrophilic | About 10%-20% |
| Shea butter preparation | Hydrophobic | About 1%-20% |
| Alpha-pinene | Hydrophobic | About 1%-10% |
| Functional Oil | Hydrophobic | About 0%-10% |
| Alcohol | Hydrophobic/Hydrophilic | About 0%-10% |
| Anti-Inflammatory | Hydrophilic/Hydrophobic | About 0%-10% |
| Water (e.g. distilled) | Hydrophilic | About 20-70% |
| Anti-Oxidant | Hydrophobic/Hydrophilic | About 0%-10% |
| Anti-Microbial | Hydrophobic/Hydrophilic | About 0%-10% |
| Flavors | Hydrophobic/Hydrophilic | About 0%-10% |
| Fragrances | Hydrophobic/Hydrophilic | About 0%-10% |
| Fatty Acid | Hydrophobic/Hydrophilic | About 0%-10% |
| Analgesic | Hydrophobic/Hydrophilic | About 0%-10% |
| Amino Acid | Hydrophobic/Hydrophilic | About 0%-10% |
| Carbohydrate | Hydrophobic/Hydrophilic | About 0%-10% |
| Vitamin | Hydrophobic/Hydrophilic | About 0%-10% |
| Solvent | Hydrophobic/Hydrophilic | About 0%-10% |
| Moisturizer | Hydrophobic/Hydrophilic | About 0%-10% |
| Other categories | Hydrophobic/Hydrophilic | About 0%-10% |

The above percentage ranges in Table VIII may be replaced by other percentages or percentage ranges (w/w) disclosed throughout this application. A composition of the present invention comprises an aloe vera preparation, a shea butter preparation, alpha-pinene, and water. In addition, a composition of this invention comprises a combination of other components identified throughout this application—hydrophilic components, hydrophobic components, and emulsifiers (which may be categorized as hydrophilic or hydrophobic). In an embodiment, a composition of this invention further comprises black cumin seed oil, alone or in combination with other functional oils. In an embodiment, a composition of this invention further comprises glycerol as a hydrophobic component. In an embodiment, a composition of this invention further comprises soluble collagen, MSM, and/or lecithin as a hydrophilic component. In an embodiment, a composition of this invention further comprises an alcohol, including for instance benzyl alcohol, cetyl alcohol, and/or panthenol. In an embodiment, a composition of this invention further comprises an anti-inflammatory such as linoleic acid or oleic acid (hydrophilic), or chamomile oil or copaiba oil (hydrophobic). In an embodiment, a composition of this invention further comprises an anti-oxidant, including for instance protocatechuic acid (hydrophilic). In an embodiment, a composition of this invention further comprises an antimicrobial such as carvacrol (hydrophobic). In an embodiment, a composition of this invention further comprises benzoin as a thickener. In an embodiment, a composition of this invention further comprises lauryl wax (35° C.-45° C. melting point), or cetyl esters wax (43° C.-47° C. melting point).

In an embodiment, the sum of hydrophilic and hydrophobic components of a composition of the present invention, not including water, may be approximately equal. For instance, in an embodiment, a composition of this invention may include about 15-30% hydrophilic components w/w, about 15-30% hydrophobic components w/w, and about 50-70% water. In another embodiment, a composition of this invention may include for instance about 25-45% hydrophilic components w/w, about 25-45% hydrophobic components w/w, and about 20%-50% w/w water.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. Use of the term "about" may be deemed as optional, in an embodiment of this invention. The preceding ranges are intended to be made clear by context, and no further limitation is implied. All method steps described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification the present invention has been described in relation to certain embodiments thereof, and many details have been put forth for the purposes of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof, and, accordingly, reference should be made to the appended claims, rather than to the foregoing specification, as indicating the scope of the invention.

We claim:

1. A method of treating a subject having Dupuytren's Disease and/or Dupuytren's Contracture, comprising the step of applying an effective amount of a topical composition comprising α-pinene, an aloe vera preparation and a shea butter preparation wherein the topical composition further comprises the emulsifier tri(polyglyceryl-3/lauryl) hydrogenated trilinoleate, to an area of the subject affected by Dupuytren's Disease and/or Dupuytren's Contracture, to reduce the subject's symptoms of the disease.

2. The method of claim 1, wherein the topical composition further comprises one or more additional components selected from the group consisting of functional oils, soluble collagens, alcohols, anti-inflammatories, anti-oxidants, anti-microbials, florals, thickeners, waxes, fragrances, fatty acids, analgesics, amino acids, carbohydrates, vitamins, solvents, gels, and moisturizers.

3. The method of claim 2, wherein the topical composition further comprises an additional emulsifier.

4. The method of claim 1, wherein the topical composition further comprises soluble collagen.

5. The method of claim 2, wherein the topical composition further comprises one or more functional oils selected from the group consisting of Black Cumin Seed Oil, Baobab Oil, Apricot Kemal Oil, Argan Nut Oil, Camellia Oil, Manila Oil, Sea Buckthom Oil, Tamanu Oil, Calendula Oil, caprylic/capric triglyceride, caryophyllene, Elemi Oil, Kanuka Oil, Litsea Cube be Oil, Palmarosa Oil, Palo Santo, Rose Hip Seed Oil, and Sachi Inchi Oil.

6. The method of claim 1, wherein the topical composition further comprises Black Cumin Seed Oil.

7. The method of claim 5, wherein the topical composition further comprises caryophyllene, caprylic/capric triglyceride, and one or more anti-inflammatories wherein said anti-inflammatory or anti-inflammatories are selected from the group consisting of chamomile oil, copaiba oil, oleic acid, and linoleic acid.

8. The method of claim 2, wherein the topical composition further comprises one or more anti-oxidants selected from the group consisting of tocopherol, tocopheryl acetate, retinyl palmitate, and tetrahexyldecyl ascorbate; and a fatty acid, wherein said fatty acid is ferulic acid.

9. The method of claim 2, wherein the topical composition further comprises one or more amino acids and one or more anti-microbials selected from the group consisting of carvacrol and niacinamide.

10. The method of claim 2, wherein the topical composition further comprises methyl sulfonyl methane, magnesium sulfate, and propylene glycol.

11. The method of claim 2, wherein the topical composition further comprises betaine, sodium PCA, sodium lactate, PCA, 1,2-hexane dial, and caprylyl glycol.

12. The method of claim 3, wherein the additional emulsifiers is one or more emulsifier selected from the group consisting of Tri-(polyglyceryl-3/Lauryl) Hydrogenated Trilinoleate; Polyglyceryl-3 Sorbityl Linseedate; Polyglyceryl-2 Oleate (and) Polyhydroxystearic Acid (and) Polyglyceryl-2 Stearate; Polyglyceryl-3 Triolivate; Polyglyceryl-3 Polyricilinoleate; Polyglyceryl-2 Dipolyhydroxystearate; Polyglyceryl-2 Sesquiisostearate; Polyglyceryl-3 Diisostearate; Polyclyceryl-6 Polyricilinoleate (and) Polyglycery-3 Diisostearate (and) Disteardimonium Hectorite; Olive Oil Polyglyceryl-6 Esters (and) Polyglyceryl-6 Pentaoleate;

Polyglycery-6 Polyricilinoleate (and) Polyglyceryl-10 Dioleate; Cetyl PEG/PPG-10/1 Dimethicone; Methylglucose Sesquioleate; and Octyldodecanol (and) octyldodecyl xyloside (and) PEG-30 dipolyhydroxystearate.

13. The method of claim 3, wherein the topical composition is an oil-in-water emulsion.

14. The method of claim 2, wherein the topical composition is a lotion, solution, balm, cream, or spray.

* * * * *